(12) United States Patent
Kerr et al.

(10) Patent No.: US 11,952,328 B2
(45) Date of Patent: Apr. 9, 2024

(54) SELECTIVE SHIP INHIBITORS FOR TREATING DISEASE

(71) Applicants: THE RESEARCH FOUNDATION FOR THE STATE UNIVERSITY OF NEW YORK, Syracuse, NY (US); SYRACUSE UNIVERSITY, Syracuse, NY (US)

(72) Inventors: William G. Kerr, Syracuse, NY (US); John D. Chisholm, Fayetteville, NY (US)

(73) Assignee: THE RESEARCH FOUNDATION FOR THE STATE UNIVERSITY OF NEW YORK, Syracuse, NY (US)

( * ) Notice: Subject to any disclaimer, the term of this patent is extended or adjusted under 35 U.S.C. 154(b) by 0 days.

(21) Appl. No.: 16/656,284

(22) Filed: Oct. 17, 2019

(65) Prior Publication Data
US 2020/0277256 A1 Sep. 3, 2020

Related U.S. Application Data

(60) Provisional application No. 62/746,793, filed on Oct. 17, 2018.

(51) Int. Cl.
| | | |
|---|---|---|
| C07C 309/47 | (2006.01) | |
| A61P 35/00 | (2006.01) | |
| C07D 241/04 | (2006.01) | |
| C07D 243/08 | (2006.01) | |
| C07D 275/06 | (2006.01) | |
| C07D 471/10 | (2006.01) | |
| C07D 487/10 | (2006.01) | |

(52) U.S. Cl.
CPC ............ *C07C 309/47* (2013.01); *A61P 35/00* (2018.01); *C07D 241/04* (2013.01); *C07D 243/08* (2013.01); *C07D 275/06* (2013.01); *C07D 471/10* (2013.01); *C07D 487/10* (2013.01)

(58) Field of Classification Search
CPC .................................................. A61K 31/135
See application file for complete search history.

(56) References Cited

U.S. PATENT DOCUMENTS

| | | |
|---|---|---|
| 2009/0023724 A1 | 1/2009 | Mortensen et al. |
| 2012/0190649 A1 | 7/2012 | Thomas et al. |
| 2015/0183741 A1 | 7/2015 | Guckian et al. |
| 2017/0189380 A1 | 7/2017 | Kerr et al. |

OTHER PUBLICATIONS

Kubinyi (3D QSAR in Drug Design: Ligand-Protein Interactions and Molecular Similarity, vol. 2-3, Springer, 1998; see p. 243).*
Wermuth, The Practice of Medicinal Chemsitry, 2d ed. (2003), 768 pages, p. 142.*
Dorwald, F. Zaragoza. Side Reactions in Organic Synthesis: A Guide to Successful Synthesis Design, Weinheim: WILEY-VCH Verlag GmbH & Co. KGaA, 2005, Preface.*
Arase, H. et al., "Fas-mediated cytotoxicity by freshly isolated natural killer cells", J Exp Med. (1995); 181: 1235-1238.
Brooks, R. et al., "Coordinate expansion of murine hematopoietic and mesenchymal stem cell compartments by SHIPi", Stem Cells. (2015); 33: 848-858.
Brooks, R. et al., "SHIP1 inhibition increases immunoregulatory capacity and triggers apoptosis of hematopoietic cancer cells", J. Immunol. (2010); 184: 3582-3589).
Collazo et al., "SHIP limits immunoregulatory capacity in the T-cell compartment", Blood, (2009); 113:2934-2944.
Collazo et al., "Lineage extrinsic and intrinsic control of immunoregulatory cell numbers by SHIP", Eur J Immunol. (2012); 42:1785-1795.
Chen, Z. et al., "Signalling thresholds and negative B-cell selection in acute lymphoblastic leukaemia", Nature. (2015).
Damen, et al., "The 145-kDa protein induced to associate with Shc by multiple cytokines is an inositol tetraphosphate and phosphatidylinositol 3,4,5-triphosphate 5-phosphatase", PNAS, (1996); 93: 1689-1693.
Dong, S. et al., "T cell receptor for antigen induces linker for activation of T cell-dependent activation of a negative signaling complex involving Dok-2, SHIP-1 and Grb-2", J Exp Med., 203(11): 2509-2518, Oct. 30, 2006.
Fernandes, S. et al., "SHIPi enhances autologous and allogeneic hematopoietic stem cell transplantation", E Bio Medicine, vol. 2, pp. 205-213, Feb. 2015.
Fernandez, et al., A subset of natural killer cells achieves self-tolerance without expressing inhibitory receptors specific for self-MHC molecules, Blood, (2005); 105: 4416-4423.
Freeburn, R. W. et al., "Evidence that SHIP-1 contributes to phosphatidylinositol 3,4,5-trisphosphate metabolism in T lymphocytes and can regulate novel phosphoinositide 3-kinase effectors", J Immunol., vol. 169, pp. 5441-5450, 2002.
Fuhler, G. M. et al., "Therapeutic potential of SH2 domain-containing inositol-5'-phosphatase 1 (SHIP1) and SHIP2 inhibition in cancer", Mol Med., vol. 18, pp. 65-75, 2012.
Ghansah, et al., "Expansion of myeloid suppressor cells in SHIP-deficient mice represses allogeneic T cell responses", J Immunol. 2004; 173:7324-7330.

(Continued)

*Primary Examiner* — Valerie Rodriguez-Garcia
(74) *Attorney, Agent, or Firm* — Peter Fallon; Lance D. Reich

(57) ABSTRACT

The present disclosure provides compositions that inhibit the SH2-containing inositol 5'phosphatase (SHIP) as well as methods using such composition for use in treating or ameliorating the effects of a medical condition in a subject. For examples, compositions including the general formula

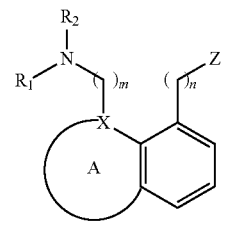

as disclosed herein are suitable for use herein.

3 Claims, 17 Drawing Sheets

(56) References Cited

OTHER PUBLICATIONS

Gumbleton, M. et al., "SHIP1 intrinsically regulates NK cell signaling and education, resulting in tolerance of an MHC class I-mismatched bone marrow graft in mice", J Immunol, vol. 194, pp. 2847-2854, 2015.

Hayakawa et al., "CD27 dissects mature NK cells into two subsets with distinct responsiveness and migratory capacity", J Immunol., vol. 176, pp. 1517-1524, 2006.

Haynes, N. M. et al., "CD11c+ dendritic cells and B cells contribute to the tumoricidal activity of anti-DR5 antibody therapy in established tumors", J Immunol., vol. 185, pp. 532-541, 2010.

Hazen, et al., "SHIP is required for a functional hematopoietic stem cell niche", Blood. (2009); 113:2924-2933.

Hodge, J. W. et al., "Vaccine therapy of established tumors in the absence of autoimmunity", Clin Cancer Res., vol. 9, Issue 3, pp. 837-1849, May 2003.

Hoekstra, E. et al., "Lipid phosphatase SHIP2 functions as oncogene in colorectal cancer by regulating PKB activation", Oncotarget, vol. 7, No. 45, pp. 73525-73540, Sep. 2016.

International Search Report and Written Opinion in related PCT Application No. PCT/US/19/56795, dated Jan. 30, 2020 (10 pages).

Irwin, J. J. et al., "ZINC—A Free Database of Commercially Available Compounds for Virtual Screening", J. Chem. Inf. Model., vol. 45, No. 1, pp. 177-182, 2005.

Irwin, J. J. et al., "Automated Docking Screens: A Feasibility Study", J. Med. Chem., vol. 52, No. 18, pp. 5712-5720, 2009.

Irwin, J. J et al., "ZINC: A Free Tool to Discover Chemistry for Biology", J. Chem. Inf. Model. vol. 52, pp. 1757-1768, 2012.

Iyer, et al., "Role of SHIP1 in bone biology", Ann N Y Acad Sci. (2013); 1280:11-14.

Murphy, W. J. et al., "Rejection of bone marrow allografts by mice with severe combined immune deficiency (SCID). Evidence that natural killer cells can mediate the specificity of marrow graft rejection", Immunity. (1996); 4:67-76.

Nagasaki, E. et al., Combined treatment with dendritic cells and 5-fluorouracil elicits augmented NK cell-mediated antitumor activity through the tumor necrosis factor-alpha pathway. J Immunother. (2010); 33: 467-474.

Paraiso, et al., "Induced SHIP deficiency expands myeloid regulatory cells and abrogates graft-versus-host disease", J Immunol. 2007; 178:2893-2900.

Park, M. Y. et al., "Impaired T-cell survival promotes mucosal inflammatory disease in SHIP1-deficient mice", Mucosal Immunol., vol. 7, No. 6, pp. 1429-1439, Nov. 2014.

Pubchem. CID 4116252, Sep. 13, 2005, pp. 1-12, https://pubchem.ncbi.nlm.nih.gov/compound/4116252.

Sakuishi, K. et al., "Targeting Tim-3 and PD-1 pathways to reverse T cell exhaustion and restore anti-tumor immunity", J Exp Med. vol. 207, No. 10, pp. 2187-2194, Sep. 2010.

Salagianni, M. et al., "NK cell adoptive transfer combined with Ontak-mediated regulatory T cell elimination induces effective adaptive antitumor immune responses", J. Immunol., vol. 186, pp. 3327-3335, 2011.

Scharenberg, et al., "Phosphatidylinositol-3,4,5-trisphosphate (PtdIns-3,4,5-P3)/Tec kinase-dependent calcium signaling pathway: a target for SHIP-mediated inhibitory signals", EMBO J, (1998); 17: 1961-1972).

Suwa, A. et al., "Discovery and functional characterization of a novel small molecule inhibitor of the intracellular phosphatase, SHIP2", Br J Pharmacol., vol. 158, pp. 879-887, 2009.

Tarasenko, T. et al., "T cell-specific deletion of the inositol phosphatase SHIP reveals its role in regulating Th1/Th2 and cytotoxic responses", Proc Natl Acad Sci., vol. 104, No. 27, pp. 11382-11387, Jul. 3, 2007.

Tu, et al., "Embryonic and hematopoietic stem cells express a novel SH2-containing inositol 5'-phosphatase isoform that partners with the Grb2 adapter protein", Blood. (2001); 98:2028-2038.

Viernes, et al., "Discovery and development of small molecule SHIP phosphatase modulators", Med Res Rev, (2014); 34(4): 795-824.

Wahle, et al., "Inappropriate recruitment and activity by the Src Homology Region 2 Domain-Containing Phosphatase 1 (SHP1) is responsible for receptor dominance in the SHIP-deficient NK cell", J Immunol, (2007);179:8009-8015.

Wang, J. W. et al., Influence of SHIP on the NK repertoire and allogeneic bone marrow transplantation. Science. (2002); 295: 2094-2097).

Waterman, P. M. et al., "The inositol 5-phosphatase SHIP-1 and adaptors Dok-1 and 2 play central roles in CD4-mediated inhibitory signaling", Immunol Lett., vol. 143, No. 1, pp. 122-130, Mar. 30, 2012.

Zamai, L. et al., Natural killer (NK) cell-mediated cytotoxicity: differential use of TRAIL and Fas ligand by immature and mature primary human NK cells, J Exp Med., vol. 188, No. 12, pp. 2375-2380, Dec. 21, 1998.

\* cited by examiner

AS1949490

K118

K149

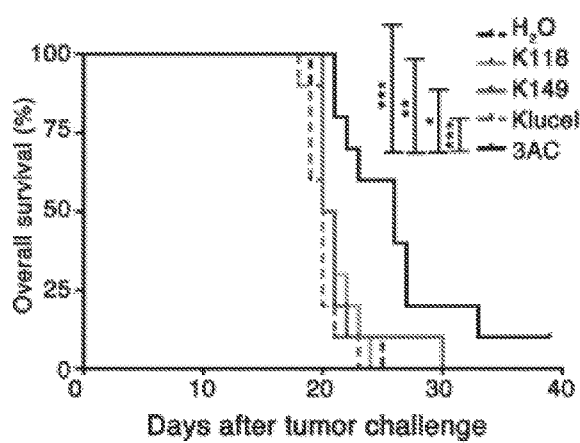
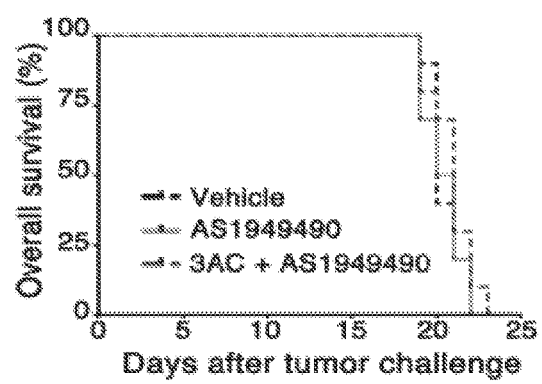
Fig. 6H
Fig. 6I

SELECTIVE SHIP INHIBITORS FOR TREATING DISEASE

CROSS-REFERENCE TO RELATED APPLICATIONS

This application claims priority to U.S. Provisional Application Ser. No. 62/746,793 filed Oct. 17, 2018, which is incorporated herein by reference in its entirety.

STATEMENT REGARDING FEDERALLY SPONSORED RESEARCH

This invention was made with government support under grant numbers R01HL085580 and R01HL072523 awarded by the National Institutes of Health. The government has certain rights in the invention.

BACKGROUND

Host defense against malignancy is mediated in part by T and natural killer (NK) cell mediated killing of malignantly transformed cells (Shankaran, V. et al., IFNgamma and lymphocytes prevent primary tumour development and shape tumour immunogenicity, Nature, (2001); 410: 1107-1111; O'Sullivan, T. et al., Cancer immunoediting by the innate immune system in the absence of adaptive immunity, J Exp Med, (2012); 209: 1869-1882; Vivier, E. et al., Innate or adaptive immunity? The example of natural killer cells, Science, 331: 44-49). However, compensatory mechanisms termed T cell exhaustion and NK cell disarming induce a state of hyporesponsiveness among chronically activated T and NK cells to prevent autoimmune disease due to misdirected targeting of healthy-self cells (Hoglund, P. et al., Current perspectives of natural killer cell education by MHC class I molecules, Nat Rev Immunol, (2010); 10: 724-734; Kim, S. et al., Licensing of natural killer cells by host major histocompatibility complex class I molecules. Nature. (2005); 436: 709-713; Fernandez, N. C. et al., A subset of natural killer cells achieves self-tolerance without expressing inhibitory receptors specific for self-MHC molecules, Blood, (2005); 105: 4416-4423; Wherry, E. J. et al., Molecular and cellular insights into T cell exhaustion, Nat Rev Immunol, (2015); 15: 486-499). Increased survival among cancer patients treated with immune checkpoint inhibitors has revealed the potential for T cells to mediate immune control of malignancy (Sharma, P. et al., The future of immune checkpoint therapy, Science, (2015); 348: 56-61).

The SH2-domain-containing inositol 5'-phosphatase, SHIP1, catalyzes the hydrolysis of the PI3K product, PI(3,4,5)P3, to form PI(3,4)P2 (Damen, J. E. et al., The 145-kDa protein induced to associate with Shc by multiple cytokines is an inositol tetraphosphate and phosphatidylinositol 3,4,5-triphosphate 5-phosphatase, PNAS, (1996); 93: 1689-1693; Scharenberg, A. M. et al., Phosphatidylinositol-3,4,5-trisphosphate (PtdIns-3,4,5-P3)/Tec kinase-dependent calcium signaling pathway: a target for SHIP-mediated inhibitory signals, EMBO J, (1998); 17: 1961-1972). Although SHIP1 can limit signaling from NK and T cell activating receptors, chronic activation of SHIP1 renders NK and T cells hyporesponsive to maintain self-tolerance. There remains a need in the art for an inhibitor of SHIP1 that increases NK and T cell responsiveness and prevents the induction of hyporesponsiveness caused by unopposed activation of SHIP1.

GvHD is an autoimmune reaction by the body to a transplanted organ or tissue, such as bone marrow used to treat cancers and genetic disorders. GvHD is the leading cause of treatment related mortality in bone marrow transplant recipients and is mediated by donor T cells that attack host tissue. GvHD is often treated with glucocorticoids, but this can increase the risk of infections and cancer relapse in the case of bone marrow transplant. Moreover, GvHD can become refractory to glucocorticoid treatment. There remains a need in the art for compounds and treatments that can treat GvHD following organ transplantation.

In addition, neutropenia, thrombocytopenia and anemia are decreases in blood cell production that are problematic side effects of cancer chemotherapy, as well as the result of accidental radiation poisoning. Treatments to increase blood cell production currently rely on the recombinant endogenous growth factors Erythropoietin (EPO) and G-CSF (NEUPOGEN), which are protein-based and therefore must be injected, as they are decomposed by the stomach when given orally. These growth factors only promote red blood cell (RBC) and granulocyte production without having a significant impact on platelet numbers. There remains a need in the art for compounds and treatments that can result in an increase in blood cell numbers to offset the side effects of chemotherapy and radiation poisoning.

BRIEF DESCRIPTION OF THE DRAWINGS

FIG. 1B shows the structure of BiPh(2,3',4,5',6)P$_5$ interacting with key SHIP2 residues. FIG. 1C shows the modified structure of FIG. 1A without the inhibitor and the amino acid sequence of SHIP1.

FIG. 2C shows the docking pose of K223 with the model of the SHIP1 active site. This predicts that the sulfonic acid is acting as a phosphate mimic, binding in active site where the 5'-phosphate of PIP3 binds.

FIG. 3D shows a box and whisker plot of the frequency of CD69 among splenic CD8+ T cells from two-day SHIP inhibitor- or vehicle-treated mice. FIG. 3E shows a box and whisker plot of the expression of CD69 among splenic CD8+ T cells from two-day SHIP inhibitor- or vehicle-treated mice. FIG. 3C (unstim: n=4, p=0.0962, Unpaired t test with Welch's correction. NK1.1: n=4, p=0.0038, Two-tailed student's T test. NKG2D: n=4, p=0.0450, Two-tailed student's T test. NKp46: n=4, p=0.0144, Two-tailed student's T test. PMA: p=0.2945, Two-tailed student's T test). FIG. 3D (n=8, p=0.0153, Unpaired T test with Welch's correction). FIG. 3E (n=8, p=0.0009, Two-tailed student's T test) FIG. 3F (n=9, p=0.0083, Two-tailed student's T test).

FIG. 4A (p=0.0433; Mann-Whitney U test). FIG. 4B (p=0.0007; Mann-Whitney U test). FIG. 4C (p=0.0153; Unpaired t test with Welch's correction). FIG. 4D (p=0.9188. Mann-Whitney U test).

FIG. 5A shows the absolute number of splenic NK cells following two days of SHIP inhibitor or vehicle treatment (p=0.0119; two-tailed Student's t-test). FIG. 5B shows the peritoneal NK cells recovered by peritoneal lavage of SHIP inhibitor or vehicle treated tumor challenged ($5 \times 10^5$ RMA-Rael cells) C57BL/6 hosts (p=0.0003; two-tailed Student's t-test). FIG. 5C shows the frequency of mature splenic NK cells CD27-CD11b$^+$) amongst total NK cells from SHIP inhibitor and vehicle treated, nave or tumor challenged C57BL/6 hosts (Naive p=0.0013; two-tailed Student's t-test; Tumor p=0.0002; two-tailed Student's t-test). FIG. 5D and FIG. 5E show the representative histograms and box-and-whisker plots of FasL expression by NK cells from C56BL/6 (p=0.0002; Unpaired t test with Welch's correction) or RAG1−/− (p<0.0001; Mann-Whitney U test) tumor challenged, SHIP inhibitor or vehicle treated hosts. FIG. 5F shows the T cells recovered by peritoneal lavage of SHIP inhibitor and vehicle treated tumor challenged hosts (p<0.0001; Mann-Whitney U test). FIG. 5G shows the splenic NK and T cell FasL expression from SHIP inhibitor or vehicle treated C57BL/6 mice. (NK cells p=0.0192; Unpaired t test with Welch's correction. T cells p=0.0659; Mann-Whitney U test). Additionally, FIGS. 5A-5G show the analysis by flow cytometry on day 3 after hosts receive SHIP inhibitor or vehicle for two consecutive days. NK cells are defined as NK1.1+CD3ε−. The graphs are representative of at least two independent experiments with at least four SHIP inhibitor and vehicle treated mice. FIG. 5H shows a line graph of RMA-Rael viability following in vitro treatment with SHIP inhibitor for 24 h at indicated doses. Viability is expressed as frequency at a given concentration expressed as a percentage of solvent only treated cells. The kill curve summarizes pooled data from three independent experiments using six replicate wells/concentration with mean ±SEM indicated (n=18 per group. One-way ANOVA with Dunnett's multiple comparisons. 0 pM vs. 20 pM Adjusted p value =0.0001. 0 pM vs. 15 pM Adjusted p value =0.0001. 0 pM vs. 10 pM Adjusted p value =0.0001. 0 pM vs. 7.5 pM Adjusted p value =0.0001. 0 pM vs. 5 pM Adjusted p value =0.0001). FIG. 5I shows induction of apoptosis (AnnexinV) and Caspase 8 in RMA cells after culture with SHIP inhibitor for 12 hours; (pooled data from two independent experiments with each experiment done in triplicate, p=0.0007, Unpaired t test with Welch's correction).

FIGS. 6A-6I show the survival of tumor bearing mice treated with a SHIP inhibitor. FIG. 6A shows Kaplan-Meier curves for overall survival in SHIP inhibitor-treated C57BL/6 (black), NSG (blue) or TcRa$^{-/-}$ (yellow) or vehicle-treated C57BL/6 (dashed black) or NSG (dashed blue) tumor challenged ($5 \times 10^5$ RMA-Rael) hosts. Hosts were treated on the day of tumor challenge and the following day as in FIG. 1. The 2-day treatment course was repeated each week for the duration of survival. FIG. 6B shows the Kaplan-Meier curves for overall survival in SHIP inhibitor-treated NK cell depleted C57BL/6 (DNK; yellow) and SHIP inhibitor-treated NK cell intact C57BL/6 (iso; black) hosts. Mice received either NK cell depleting, anti-NK1.1 antibody (PK136), or isotype control antibody prior to tumor challenge ($5 \times 10^5$ RMA-Rael). The hosts received SHIP inhibitor two consecutive days each week until death. FIG. 6C shows the Kaplan-Meier curves for overall survival in tumor challenged ($10^5$ RMA-Rael) C57BL/6 hosts that received sustained, six consecutive days each week, SHIP inhibitor (black) or vehicle (dashed blue). FIG. 6D shows Kaplan-Meier curves for overall survival in tumor challenged ($5 \times 10^5$ RMA-Rael) CD4CreSHIP$^{flox/flox}$, SHIP$^{+/flox}$ and SHIPflox/flox hosts that were treated with 3AC or vehicle as indicated. The hosts were treated on the day of tumor challenge and the following day as in FIG. 1. The 2-day treatment course was repeated each week for the duration of survival. FIG. 6E shows the chemical structure of AS9149490, FIG. 6F shows the chemical structure of K118, and FIG. 6G shows the chemical structure of K149. FIG. 6H shows Kaplan-Meier curves for overall survival in tumor challenged ($1 \times 10^5$ RMA-Rael) C57BL/6 hosts treated with 3AC (SHIP1 selective inhibitor; black), Klucel (3AC's vehicle; dashed blue), K118 (pan-SHIP1/2 inhibitor; yellow), K149 (pan-SHIP1/2 inhibitor; purple), or water (K118 and K149 vehicle; dashed black). FIG. 6I shows Kaplan-Meier curves for overall survival in tumor challenged ($1 \times 10^5$ RMA-Rael) C57BL/6 hosts treated with AS1949490 (SHIP2 selective inhibitor; yellow), 3AC in combination with AS1949490 (blue dotted line), or vehicle (black dotted line).

FIG. 7A and FIG. 7B show CT26 (FIG. 7A) and MC-38 (FIG. 7B) viability following in vitro treatment with 3AC for 24 h at indicated doses. Relative viability is expressed as frequency compared to solvent only treated cells. Kill curve summarizes pooled data from three independent experiments using six replicate wells/concentration with mean±SEM indicated. BALB/C mice were challenged with subcutaneous injection of CT26 colon carcinoma cells in the right flank. Mice were treated with either 2 consecutive days of 3AC or vehicle control each week as in FIG. 4A. Tumor size at 14, 21, 9 and 28 days (FIG. 7C), and tumor weight on day 28 determined after dissection of tumor (FIG. 7E). FIG. 7G shows representative samples of H&E stained tissue sections. C57BL/6 mice were challenged with subcutaneous injection of MC-38 colon carcinoma cells in the right flank. Mice were treated with either 2 consecutive days of SHIP inhibitor or vehicle control each week as in FIG. 4A. Tumor size at 14, 21 and 25 days (FIG. 7D), and tumor weight (FIG. 7F) on day 25 were determined after dissection of tumor. FIG. 7H shows Representative samples of H&E stained tissue sections. FIG. 7A (n=18 per group. One-way ANOVA with Dunnett's multiple comparisons. 0 μM vs. 20 μM Adjusted p value=0.0463. All other concentrations of SHIP inhibitor compared with solvent only N.S.). FIG. 7B (n=18 per group. One-way ANOVA with Dunnett's multiple comparisons. All concentrations of SHIP inhibitor compared with solvent only N.S.). FIGS. 7C-7F graphs represent data from one of two independent experiments. FIG. 7C (n=10. Day 14 p<0.0001, Unpaired t test with Welch's correction. Day 21 p<0.0001, two-tailed student's t-test. Day 28 p<0.0001, two-tailed Student's t-test). FIG. 7E (n=10. P<0.0001, two-tailed Student's t-test) FIG. 7D (n=10. Day 14 p=0.0005, two-tailed student's t-test. Day 21 p=0.0009, two-tailed Student's t-test. Day 25 p=0.0009, two-tailed student's t-test). FIG. 7F (n=10. P=0.0067, two-tailed student's t-test).

SUMMARY

Figure 1A:
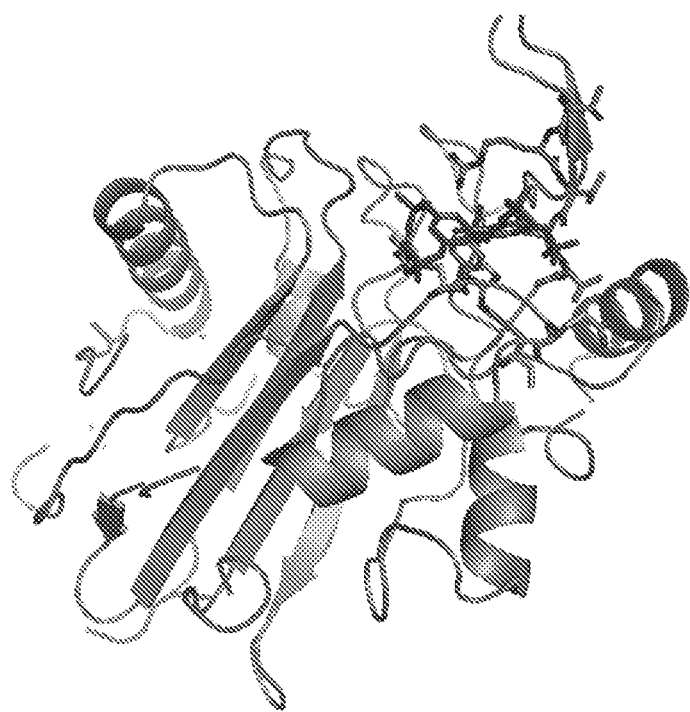
FIGS. 1A-1C show the X-Ray crystal structure of the active site of SHIP2 and the results of docking studies using the structure or SHIP2. The X-ray crystal structure of the SHIP2 active site bound to BiPh(2,3',4,5',6)Psis shown in FIG. 1A. The 5' phosphate of BiPh(2,3',4,5',6)P$_5$ mimics the 5' phosphatase of PI(3,4,5)P$_3$. This phosphate shows hydrogen bonds to R682, Y661 and R611. The hydrogen-bonding network forces the phosphate into a conformation where hydrolysis is facilitated.

Provided herein are compounds useful for the treatment of hematopoietic malignancy or anemia in a subject in need thereof. Also provided herein are compounds useful for the activation of NK cells and T cells to activate or increase a host defense against a malignancy in a subject.

Thus, in an aspect, provided herein is a compound of Formula I:

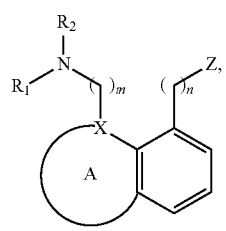

(I)

or a pharmaceutically acceptable salt or solvate thereof, wherein

A is $C_2$-$C_{12}$ aryl, $C_2$-$C_{12}$ heteroaryl, $C_1$-$C_{12}$ heteroalkyl, or absent;

X is C or $C(R_3)$;

$R_1$ is $C_1$-$C_6$alkyl-$N(R_4)(R_5)$, wherein the alkyl is optionally substituted with 1, 2, or 3 groups, each independently selected from $C_1$-$C_{12}$ alkyl or $C_0$-$C_{12}$ alkyl($C_6$-$C_{12}$ aryl);

$R_2$ is H or $C_1$-$C_6$alkyl;

$R_3$ is H or $C_6$-$C_{12}$ aryl;

$R_4$ is H or $C_1$-$C_6$alkyl;

$R_5$ is H or $C_1$-$C_6$alkyl, wherein $R_2$ and $R_5$ are taken together from the nitrogen atoms to which they are bound to form a heterocycle or spiro-heterocycle;

Z is —$S(O)_2OR_6$, —$S(O)_2N(R_7)(R_8)$, —$P(O)_2OR_9$, —$P(S)(OR_{10})_2$, or —$S(O)_2R_{11}$;

$R_6$ is $C_1$-$C_{12}$alkyl, $C_{12}$alkenyl, —$C(O)C_1$-$C_{12}$alkyl, —$C(O)OC_1$-$C_{12}$alkyl, —$C(O)N(C_1$-$C_{12}$alkyl$)_2$ or $C_6$-$C_{12}$ aryl, wherein alkyl, alkenyl, and aryl are optionally substituted with 1, 2, or 3 groups, each independently selected from halo, —OH, $C_1$-$C_6$alkyl, $C_1$-$C_6$-haloalkyl, —O-$C_1$-$C_6$alkyl, —$NO_2$, —$N(H)(R_{12})$, and —CN;

$R_7$ is H, $C_1$-$C_6$alkyl, or $C_1$-$C_6$alkenyl, wherein alkyl and alkenyl are optionally substituted with 1, 2, or 3 groups, each independently selected from halo, —OH, $C_1$-$C_6$alkyl, $C_1$-$C_6$-haloalkyl, —O—$C_1$-$C_6$alkyl, —$NO_2$, —$N(H)(R_{12})$, and —CN;

$R_8$ is H, $C_1$-$C_6$alkyl, or $C_1$-$C_6$alkenyl, wherein alkyl and alkenyl are optionally substituted with 1, 2, or 3 groups, each independently selected from halo, —OH, $C_1$-$C_6$alkyl, $C_1$-$C_6$-haloalkyl, —O—$C_1$-$C_6$alkyl, —$NO_2$, —$N(H)(R_{12})$, and —CN;

$R_9$ is H, $C_1$-$C_{12}$alkyl, or $C_1$-$C_{12}$alkenyl, —$C(O)C_1$-$C_{12}$alkyl, —$C(O)OC_1C_{12}$alkyl, —$C(O)N(C_1$-$C_{12}$alkyl$)_2$ or $C_6$-$C_{12}$ aryl, alkenyl, and aryl are optionally substituted with 1, 2, or 3 groups, each independently selected from halo, —OH, $C_1$-$C_6$alkyl, $C_1$-$C_6$-haloalkyl, —O—$C_1$-$C_6$alkyl, —$NO_2$, —$N(H)(R_{12})$, and —CN;

$R_{10}$ is H, $C_1$-$C_{12}$alkyl, or $C_1$-$C_{12}$alkenyl, —$C(O)C_1$-$C_{12}$alkyl, —$C(O)OC_1C_{12}$alkyl, —$C(O)N(C_1$-$C_{12}$alkyl$)_2$ or $C_6$-$C_{12}$ aryl, alkenyl, and aryl are optionally substituted with 1, 2, or 3 groups, each independently selected from halo, —OH, $C_1$-$C_6$alkyl, $C_1$-$C_6$-haloalkyl, —O—$C_1$-$C_6$alkyl, —$NO_2$, —$N(H)(R_{12})$, and —CN;

$R_{11}$ is $C_1$-$C_{12}$alkyl, or $C_1$-$C_{12}$alkenyl, —$C(O)C_1$-$C_{12}$alkyl, —$C(O)OC_1C_{12}$alkyl, —$C(O)N(C_1$-$C_{12}$alkyl$)_2$ or $C_6$-$C_{12}$ aryl, wherein alkyl, alkenyl, and aryl are optionally substituted with 1, 2, or 3 groups, each independently selected from halo, —OH, $C_1$-$C_6$alkyl, $C_1$-$C_6$-haloalkyl, —O—$C_1$-$C_6$alkyl, —$NO_2$, —$N(H)(R_{12})$, and —CN; wherein $R_{11}$ is optionally taken together with $R_1$ to form a covalent bond;

$R_{12}$ is a protecting group;

n is 0 or 1; and m is 0 or 1.

In an embodiment, the compound of Formula I has the structure of Formula II:

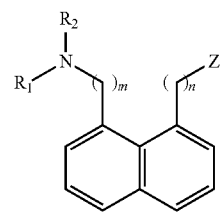

(II)

or a pharmaceutically acceptable salt or solvate thereof, wherein $R_1$ is $C_1$-$C_6$alkyl-$N(R_4)(R_5)$, wherein the alkyl is optionally substituted with 1, 2, or 3 groups, each independently selected from $C_1$-$C_{12}$ alkyl or $C_0$-$C_{12}$ alkyl($C_6$-$C_{12}$ aryl);

$R_2$ is H or $C_1$-$C_6$alkyl;

$R_4$ is H or $C_1$-$C_6$alkyl;

$R_5$ is H or $C_1$-$C_6$alkyl, wherein $R_2$ and $R_5$ are taken together from the nitrogen atoms to which they are bound to form a heterocycle or spiro-heterocycle;

Z is —$S(O)_2OR_6$, —$S(O)_2N(R_7)(R_8)$, —$P(O)_2OR_9$, —$P(S)(OR_{10})_2$, or —$S(O)_2R_{11}$;

$R_6$ is $C_1$-$C_{12}$alkyl, $C_1$-$C_{12}$alkenyl, —$C(O)C_1$-$C_{12}$alkyl, —$C(O)OC_1$-$C_{12}$alkyl, —$C(O)N(C_1$-$C_{12}$alkyl$)_2$ or $C_1$-$C_{12}$aryl, wherein alkyl, alkenyl, and aryl are optionally substituted with 1, 2, or 3 groups, each independently selected from halo, —OH, $C_1$-$C_6$-alkyl, $C_1$-$C_6$-haloalkyl, —O-$C_1$-$C_6$alkyl, —$NO_2$, —$N(H)(R_{12})$, and —CN;

$R_7$ is H, $C_1$-$C_6$alkyl, or $C_1$-$C_6$alkenyl, wherein alkyl and alkenyl are optionally substituted with 1, 2, or 3 groups, each independently selected from halo, —OH, $C_1$-$C_6$alkyl, $C_1$-$C_6$-haloalkyl, —O—$C_1$-$C_6$alkyl, —$NO_2$, —N(H)($R_{12}$), and —CN;

$R_8$ is H, $C_1$-$C_6$alkyl, or $C_1$-$C_6$alkenyl, wherein alkyl and alkenyl are optionally substituted with 1, 2, or 3 groups, each independently selected from halo, —OH, $C_1$-$C_6$alkyl, $C_1$-$C_6$-haloalkyl, —O—$C_1$-$C_6$alkyl, —$NO_2$, —N(H)($R_{12}$), and —CN;

$R_9$ is H, $C_1$-$C_{12}$alkyl, or $C_1$-$C_{12}$alkenyl, —C(O)$C_1$-$C_{12}$alkyl, —C(O)O$C_1C_{12}$alkyl, —C(O)N($C_1$-$C_{12}$alkyl)$_2$ or $C_6$-$C_{12}$ aryl, alkenyl, and aryl are optionally substituted with 1, 2, or 3 groups, each independently selected from halo, —OH, $C_1$-$C_6$alkyl, $C_1$-$C_6$-haloalkyl, —O—$C_1$-$C_6$alkyl, —$NO_2$, —N(H)($R_{12}$), and —CN;

$R_{10}$ is H, $C_1$-$C_{12}$alkyl, or $C_1$-$C_{12}$alkenyl, —C(O)$C_1$-$C_{12}$alkyl, —C(O)O$C_1C_{12}$alkyl, —C(O)N($C_1$-$C_{12}$alkyl)$_2$ or $C_6$-$C_{12}$ aryl, alkenyl, and aryl are optionally substituted with 1, 2, or 3 groups, each independently selected from halo, —OH, $C_1$-$C_6$alkyl, $C_1$-$C_6$-haloalkyl, —O—$C_1$-$C_6$alkyl, —$NO_2$, —N(H)($R_{12}$), and —CN;

$R_{11}$ is $C_1$-$C_{12}$alkyl, or $C_1$-$C_{12}$alkenyl, —C(O)$C_1$-$C_{12}$alkyl, —C(O)O$C_1C_{12}$alkyl, —C(O)N($C_1$-$C_{12}$alkyl)$_2$ or $C_6$-$C_{12}$ aryl, wherein alkyl, alkenyl, and aryl are optionally substituted with 1, 2, or 3 groups, each independently selected from halo, —OH, $C_1$-$C_6$alkyl, $C_1$-$C_6$-haloalkyl, —O—$C_1$-$C_6$alkyl, —$NO_2$, —N(H)($R_{12}$), and —CN; wherein $R_{11}$ is optionally taken together with $R_1$ to form a covalent bond;

$R_{12}$ is a protecting group;

n is 0 or 1; and m is 0 or 1.

In another aspect, provided herein is a compound of Formula III:

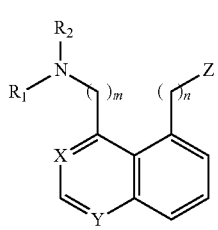

(III)

or a pharmaceutically acceptable salt or solvate thereof, wherein

X is N or C(H);

Y is N or C(H);

$R_1$ is $C_1$-$C_6$alkyl-N($R_4$)($R_5$), wherein the alkyl is optionally substituted with 1, 2, or 3 groups, each independently selected from $C_1$-$C_{12}$ alkyl or $C_0$-$C_{12}$ alkyl($C_6$-$C_{12}$ aryl);

$R_2$ is H or $C_1$-$C_6$alkyl;

$R_4$ is H or $C_1$-$C_6$alkyl;

$R_5$ is H or $C_1$-$C_6$alkyl, wherein $R_2$ and $R_5$ are taken together from the nitrogen atoms to which they are bound to form a heterocycle or spiro-heterocycle;

Z is —S(O)$_2$O$R_6$, —S(O)$_2$N($R_7$)($R_8$), —P(O)$_2$O$R_9$,—P(S)(O$R_{10}$)$_2$, or —S(O)$_2R_{11}$;

$R_6$ is $C_1$-$C_{12}$alkyl, $C_1$-$C_{12}$alkenyl, —C(O)$C_1$-$C_{12}$alkyl, —C(O)O$C_1$-$C_{12}$alkyl, —C(O)N($C_1$-$C_{12}$alkyl)$_2$ or $C_1$-$C_{12}$aryl, wherein alkyl, alkenyl, and aryl are optionally substituted with 1, 2, or 3 groups, each independently selected from halo, —OH, $C_1$-$C_6$-alkyl, $C_1$-$C_6$-haloalkyl, —O-$C_1$-$C_6$alkyl, —$NO_2$, —N(H)($R_{12}$), and —CN;

$R_7$ is H, $C_1$-$C_6$alkyl, or $C_1$-$C_6$alkenyl, wherein alkyl and alkenyl are optionally substituted with 1, 2, or 3 groups, each independently selected from halo, —OH, $C_1$-$C_6$alkyl, $C_1$-$C_6$-haloalkyl, —O—$C_1$-$C_6$alkyl, —$NO_2$, —N(H)($R_{12}$), and —CN;

$R_8$ is H, $C_1$-$C_6$alkyl, or $C_1$-$C_6$alkenyl, wherein alkyl and alkenyl are optionally substituted with 1, 2, or 3 groups, each independently selected from halo, —OH, $C_1$-$C_6$alkyl, $C_1$-$C_6$-haloalkyl, —O—$C_1$-$C_6$alkyl, —$NO_2$, —N(H)($R_{12}$), and —CN;

$R_9$ is H, $C_1$-$C_{12}$alkyl, or $C_1$-$C_{12}$alkenyl, —C(O)$C_1$-$C_{12}$alkyl, —C(O)O$C_1C_{12}$alkyl, —C(O)N($C_1$-$C_{12}$alkyl)$_2$ or $C_6$-$C_{12}$ aryl, alkenyl, and aryl are optionally substituted with 1, 2, or 3 groups, each independently selected from halo, —OH, $C_1$-$C_6$alkyl, $C_1$-$C_6$-haloalkyl, —O—$C_1$-$C_6$alkyl, —$NO_2$, —N(H)($R_{12}$), and —CN;

$R_{10}$ is H, $C_1$-$C_{12}$alkyl, or $C_1$-$C_{12}$alkenyl, —C(O)$C_1$-$C_{12}$alkyl, —C(O)O$C_1C_{12}$alkyl, —C(O)N($C_1$-$C_{12}$alkyl)$_2$ or $C_6$-$C_{12}$ aryl, alkenyl, and aryl are optionally substituted with 1, 2, or 3 groups, each independently selected from halo, —OH, $C_1$-$C_6$alkyl, $C_1$-$C_6$-haloalkyl, —O—$C_1$-$C_6$alkyl, —$NO_2$, —N(H)($R_{12}$), and —CN;

$R_{11}$ is $C_1$-$C_{12}$alkyl, or $C_1$-$C_{12}$alkenyl, —C(O)$C_1$-$C_{12}$alkyl, —C(O)O$C_1C_{12}$alkyl, —C(O)N($C_1$-$C_{12}$alkyl)$_2$ or $C_6$-$C_{12}$ aryl, wherein alkyl, alkenyl, and aryl are optionally substituted with 1, 2, or 3 groups, each independently selected from halo, —OH, $C_1$-$C_6$alkyl, $C_1$-$C_6$-haloalkyl, —O—$C_1$-$C_6$alkyl, —$NO_2$, —N(H)($R_{12}$), and —CN; wherein $R_{11}$ is optionally taken together with $R_1$ to form a covalent bond;

$R_{12}$ is a protecting group;

n is 0 or 1; and m is 0 or 1.

In yet another aspect, provided herein is a compound of Formula IV:

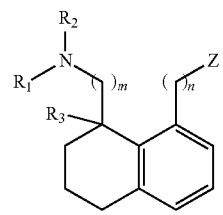

(IV)

or a pharmaceutically acceptable salt or solvate thereof, wherein $R_1$ is $C_1$-$C_6$alkyl-N($R_4$)($R_5$), wherein the alkyl is optionally substituted with 1, 2, or 3 groups, each independently selected from $C_1$-$C_{12}$ alkyl or $C_0$-$C_{12}$ alkyl($C_6$-$C_{12}$ aryl);

$R_2$ is H or $C_1$-$C_6$alkyl;

$R_3$ is H or $C_6$-$C_{12}$ aryl;

$R_4$ is H or $C_1$-$C_6$alkyl;

$R_5$ is H or $C_1$-$C_6$alkyl, wherein $R_2$ and $R_5$ are taken together from the nitrogen atoms to which they are bound to form a heterocycle or spiro-heterocycle;

Z is —S(O)$_2$O$R_6$, —S(O)$_2$N($R_7$)($R_8$), —P(O)$_2$O$R_9$, —P(S)(O$R_{10}$)$_2$, or —S(O)$_2R_{11}$;

$R_6$ is $C_1$-$C_{12}$alkyl, $C_{12}$alkenyl, —C(O)$C_1$-$C_{12}$alkyl, —C(O)O$C_1$-$C_{12}$alkyl, —C(O)N($C_1$-$C_{12}$alkyl)$_2$ or $C_6$-$C_{12}$ aryl, wherein alkyl, alkenyl, and aryl are optionally substituted with 1, 2, or 3 groups, each independently selected from halo, —OH, $C_1$-$C_6$-alkyl, $C_1$-$C_6$-haloalkyl, —O-$C_1$-$C_6$alkyl, —$NO_2$, —N(H)($R_{12}$), and —CN;

$R_7$ is H, $C_1$-$C_6$alkyl, or $C_1$-$C_6$alkenyl, wherein alkyl and alkenyl are optionally substituted with 1, 2, or 3 groups, each independently selected from halo, —OH, $C_1$-$C_6$alkyl, $C_1$-$C_6$-haloalkyl, —O—$C_1$-$C_6$alkyl, —$NO_2$, —N(H)($R_{12}$), and —CN;

$R_8$ is H, $C_1$-$C_6$alkyl, or $C_1$-$C_6$alkenyl, wherein alkyl and alkenyl are optionally substituted with 1, 2, or 3 groups, each independently selected from halo, —OH, $C_1$-$C_6$alkyl, $C_1$-$C_6$-haloalkyl, —O—$C_1$-$C_6$alkyl, —$NO_2$, —N(H)($R_{12}$), and —CN;

$R_9$ is H, $C_1$-$C_{12}$alkyl, or $C_1$-$C_{12}$alkenyl, —C(O)$C_1$-$C_{12}$alkyl, —C(O)O$C_1C_{12}$alkyl, —C(O)N($C_1$-$C_{12}$alkyl)$_2$ or $C_6$-$C_{12}$ aryl, alkenyl, and aryl are optionally substituted with 1, 2, or 3 groups, each independently selected from halo, —OH, $C_1$-$C_6$alkyl, $C_1$-$C_6$-haloalkyl, —O—$C_1$-$C_6$alkyl, —$NO_2$, —N(H)($R_{12}$), and —CN;

$R_{10}$ is H, $C_1$-$C_{12}$alkyl, or $C_1$-$C_{12}$alkenyl, —C(O)$C_1$-$C_{12}$alkyl, —C(O)O$C_1C_{12}$alkyl, —C(O)N($C_1$-$C_{12}$alkyl)$_2$ or $C_6$-$C_{12}$ aryl, alkenyl, and aryl are optionally substituted with 1, 2, or 3 groups, each independently selected from halo, —OH, $C_1$-$C_6$alkyl, $C_1$-$C_6$-haloalkyl, —O—$C_1$-$C_6$alkyl, —$NO_2$, —N(H)($R_{12}$), and —CN;

$R_{11}$ is $C_1$-$C_{12}$alkyl, or $C_1$-$C_{12}$alkenyl, —C(O)$C_1$-$C_{12}$alkyl, —C(O)O$C_1C_{12}$alkyl, —C(O)N($C_1$-$C_{12}$alkyl)$_2$ or $C_6$-$C_{12}$ aryl, wherein alkyl, alkenyl, and aryl are optionally substituted with 1, 2, or 3 groups, each independently selected from halo, —OH, $C_1$-$C_6$alkyl, $C_1$-$C_6$-haloalkyl, —O—$C_1$-$C_6$alkyl, —$NO_2$, —N(H)($R_{12}$), and —CN; wherein $R_{11}$ is optionally taken together with $R_1$ to form a covalent bond;

$R_{12}$ is a protecting group;

n is 0 or 1; and m is 0 or 1.

In a further aspect, provided herein is a compound of Formula V:

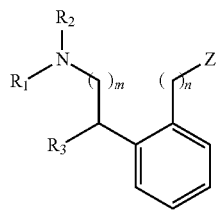

(V)

or a pharmaceutically acceptable salt or solvate thereof, wherein:

$R_1$ is $C_1$-$C_6$alkyl-N($R_4$)($R_5$), wherein the alkyl is optionally substituted with 1, 2, or 3 groups, each independently selected from $C_1$-$C_{12}$ alkyl or $C_0$-$C_{12}$ alkyl($C_6$-$C_{12}$ aryl);

$R_2$ is H or $C_1$-$C_6$alkyl;

$R_3$ is H or $C_6$-$C_{12}$ aryl;

$R_4$ is H or $C_1$-$C_6$alkyl;

$R_5$ is H or $C_1$-$C_6$alkyl, wherein $R_2$ and $R_5$ are taken together from the nitrogen atoms to which they are bound to form a heterocycle or spiro-heterocycle;

Z is —S(O)$_2$O$R_6$, —S(O)$_2$N($R_7$)($R_8$), —P(O)$_2$O$R_9$, —P(S)(O$R_{10}$)$_2$, or —S(O)$_2R_{11}$;

$R_6$ is $C_1$-$C_{12}$alkyl, $C_{12}$alkenyl, —C(O)$C_1$-$C_{12}$alkyl, —C(O)O$C_1$-$C_{12}$alkyl, —C(O)N($C_1$-$C_{12}$alkyl)$_2$ or $C_6$-$C_{12}$ aryl, wherein alkyl, alkenyl, and aryl are optionally substituted with 1, 2, or 3 groups, each independently selected from halo, —OH, $C_1$-$C_6$alkyl, $C_1$-$C_6$-haloalkyl, —O-$C_1$-$C_6$alkyl, —$NO_2$, —N(H)($R_{12}$), and —CN;

$R_7$ is H, $C_1$-$C_6$alkyl, or $C_1$-$C_6$alkenyl, wherein alkyl and alkenyl are optionally substituted with 1, 2, or 3 groups, each independently selected from halo, —OH, $C_1$-$C_6$alkyl, $C_1$-$C_6$-haloalkyl, —O—$C_1$-$C_6$alkyl, —$NO_2$, —N(H)($R_{12}$), and —CN;

$R_8$ is H, $C_1$-$C_6$alkyl, or $C_1$-$C_6$alkenyl, wherein alkyl and alkenyl are optionally substituted with 1, 2, or 3 groups, each independently selected from halo, —OH, $C_1$-$C_6$alkyl, $C_1$-$C_6$-haloalkyl, —O—$C_1$-$C_6$alkyl, —$NO_2$, —N(H)($R_{12}$), and —CN;

$R_9$ is H, $C_1$-$C_{12}$alkyl, or $C_1$-$C_{12}$alkenyl, —C(O)$C_1$-$C_{12}$alkyl, —C(O)O$C_1C_{12}$alkyl, —C(O)N($C_1$-$C_{12}$alkyl)$_2$ or $C_6$-$C_{12}$ aryl, alkenyl, and aryl are optionally substituted with 1, 2, or 3 groups, each independently selected from halo, —OH, $C_1$-$C_6$alkyl, $C_1$-$C_6$-haloalkyl, —O—$C_1$-$C_6$alkyl, —$NO_2$, —N(H)($R_{12}$), and —CN;

$R_{10}$ is H, $C_1$-$C_{12}$alkyl, or $C_1$-$C_{12}$alkenyl, —C(O)$C_1$-$C_{12}$alkyl, —C(O)O$C_1C_{12}$alkyl, —C(O)N($C_1$-$C_{12}$alkyl)$_2$ or $C_6$-$C_{12}$ aryl, alkenyl, and aryl are optionally substituted with 1, 2, or 3 groups, each independently selected from halo, —OH, $C_1$-$C_6$alkyl, $C_1$-$C_6$-haloalkyl, —O—$C_1$-$C_6$alkyl, —$NO_2$, —N(H)($R_{12}$), and —CN;

$R_{11}$ is $C_1$-$C_{12}$alkyl, or $C_1$-$C_{12}$alkenyl, —C(O)$C_1$-$C_{12}$alkyl, —C(O)O$C_1C_{12}$alkyl, —C(O)N($C_1$-$C_{12}$alkyl)$_2$ or $C_6$-$C_{12}$ aryl, wherein alkyl, alkenyl, and aryl are optionally substituted with 1, 2, or 3 groups, each independently selected from halo, —OH, $C_1$-$C_6$alkyl, $C_1$-$C_6$-haloalkyl, —O—$C_1$-$C_6$alkyl, —$NO_2$, —N(H)($R_{12}$), and —CN; wherein $R_{11}$ is optionally taken together with $R_1$ to form a covalent bond;

$R_{12}$ is a protecting group;

n is 0 or 1; and m is 0 or 1.

In another aspect, provided herein is a pharmaceutical composition comprising a compound of Formula I, II, III, IV, or V, or a pharmaceutically acceptable salt or solvate thereof.

In another aspect, provided herein is a pharmaceutical composition comprising a SHIP1 inhibitor and a pharmaceutically acceptable carrier.

In another aspect, provided herein is a method for inhibiting a SH2-containing inositol 5'-phosphatase (SHIP) in a subject, the method comprising administering a safe and effective amount of a compound of Formula I, II, III, IV, V, 8-((2-aminoethyl)amino)naphthalene-1-sulfonic acid, or a pharmaceutically acceptable salt or solvate thereof.

In another aspect, provided herein is a method for inhibiting activity associated with SH2-containing inositol 5'-phosphatase (SHIP) in a mammalian cell, the method comprising administering a safe and effective amount of a compound of Formula I, II, III, IV, V, 8-((2-aminoethyl)amino)naphthalene-1-sulfonic acid, or a pharmaceutically acceptable salt or solvate thereof.

In another aspect, provided herein is a method for treating a hematopoietic malignancy in a subject, the method comprising administering a safe and effective amount of a compound of Formula I, II, III, IV, V, 8-((2-aminoethyl)amino)naphthalene-1-sulfonic acid, or a pharmaceutically acceptable salt or solvate thereof.

In another aspect, provided herein is a method for increasing hematopoiesis, the method comprising administering a safe and effective amount of a compound according to any one of Formula I, II, III, IV, V, 8-((2-aminoethyl)amino) naphthalene-1-sulfonic acid, or a pharmaceutically acceptable salt or solvate thereof.

In another aspect, provided herein is a method for treating anemia, the method comprising administering a safe and effective amount of a compound according to any one of Formula I, II, III, IV, V, 8-((2-aminoethyl)amino)naphthalene-1-sulfonic acid, or a pharmaceutically acceptable salt or solvate thereof.

In another aspect, provided herein is a method for activating natural killer (NK) cells ex vivo, the method comprising administering a compound according to any one of Formula I, II, III, IV, V, 8-((2-aminoethyl)amino)naphthalene-1-sulfonic acid, or a pharmaceutically acceptable salt or solvate thereof.

In another aspect, provided herein is a method for activating natural killer (NK) cells and T cells in a subject suffering from an illness or condition for which NK cells and/or T cells provide a host defense, the method comprising administering a safe and effective amount of a compound according to any one of Formula I, II, III, IV, V, 8-((2-aminoethyl)amino)naphthalene-1-sulfonic acid, or a pharmaceutically acceptable salt or solvate thereof.

In another aspect, provided herein is a method for treating an epithelial malignancy in a subject by promoting an anti-tumor NK cell and/or T cell response, the method comprising administering a safe and effective amount of a compound according to any one of Formula I, II, III, IV, V, 8-((2-aminoethyl)amino)naphthalene-1-sulfonic acid, or a pharmaceutically acceptable salt or solvate thereof.

In another aspect, provided herein is a method for administering a compound of Formula I, II, III, IV, V, 8-((2-aminoethyl)amino)naphthalene-1-sulfonic acid, or a pharmaceutically acceptable salt or solvate thereof, to the subject using a pulsatile dose regimen.

In some embodiments, the pulsatile dose regimen comprises at least two dosing cycles, each dosing cycle followed by a rest period of between three and seven days, with each dosing cycle comprising a first dose administration. In some embodiments, the pulsatile dose regimen comprises at least two dosing cycles, each dosing cycle followed by a rest period of between three and seven days, each dosing cycle comprising: a first dose administration followed by a first-time interval of one day; and a second dose administration. In some embodiments, the pulsatile dose regimen comprises at least two dosing cycles, each dosing cycle followed by a rest period of between three and seven days, each dosing cycle comprising: two dose administrations, each dose administration followed by a time interval of one day; and a third dose administration. In some embodiments, the pulsatile dose regimen comprises at least two dosing cycles, each dosing cycle followed by a rest period of between three and seven days, each dosing cycle comprising: three dose administrations, each dose administration followed by a time interval of one day; and a fourth dose administration.

In some embodiments, the pulsatile dose regimen comprises at least two dosing cycles, each dosing cycle followed by a rest period of between three and seven days, each dosing cycle comprising: two dose administrations, each dose administration followed by a time interval of between six and twelve hours. In some embodiments, the pulsatile dose regimen comprises at least two dosing cycles, each dosing cycle followed by a rest period of between three and seven days, each dosing cycle comprising: four dose administrations, each dose administration followed by a time interval of between six and twelve hours. In some embodiments, the pulsatile dose regimen comprises at least two dosing cycles, each dosing cycle followed by a rest period of between three and seven days, each dosing cycle comprising: six dose administrations, each dose administration followed by a time interval of between six and twelve hours. In some embodiments, the pulsatile dose regimen comprises at least two dosing cycles, each dosing cycle followed by a rest period of between three and seven days, each dosing cycle comprising: eight dose administrations, each dose administration followed by a time interval of between six and twelve hours.

In some embodiments, the pulsatile dose regimen comprises at least two dosing cycles, each dosing cycle followed by a rest period of between three and seven days, each dosing cycle comprising: three dose administrations, each dose administration followed by a time interval of between three and six hours. In some embodiments, the pulsatile dose regimen comprises at least two dosing cycles, each dosing cycle followed by a rest period of between three and seven days, each dosing cycle comprising: six dose administrations, each dose administration followed by a time interval of between three and six hours. In some embodiments, the pulsatile dose regimen comprises at least two dosing cycles, each dosing cycle followed by a rest period of between three and seven days, each dosing cycle comprising: nine dose administrations, each dose administration followed by a time interval of between three and six hours. In some embodiments, the pulsatile dose regimen comprises at least two dosing cycles, each dosing cycle followed by a rest period of between three and seven days, each dosing cycle comprising: twelve dose administrations, each dose administration followed by a time interval of between three and six hours.

DETAILED DESCRIPTION

Chronic stimulation of T and NK cells results in hyporesponsiveness in an effort to maintain self-tolerance (Shifrin, N. et al., NK cell self-tolerance, responsiveness and missing self-recognition, Semin Immunol, (2014); 26: 138-144). This, in part, allows for progression and metastatic spread of malignancy as tolerant cytotoxic lymphocytes are unable to eradicate the disease (Iannello, A. et al., Immunosurveillance of senescent cancer cells by natural killer cell, Curr Opin Immunol, (2014); 3: e27616; Iannello, A. et al, Immunosurveillance and immunotherapy of tumors by innate immune cells, Curr Opin Immunol, (2016); 38: 52-58). Multiple strategies to activate the host immune system against malignancy are currently used in clinical practice or under investigation in clinical trials. For example, Ibrutinib is a small molecule inhibitor of ITK that is both capable of directly inducing apoptosis of tumor cells and was recently shown to induce polarization towards a Th1 response acting as a chemoimmunotherapeutic (Dubovsky, J. A. et al.; Ibrutinib is an irreversible molecular inhibitor of ITK driving a Th1-selective pressure in T lymphocytes, Blood, (2013); 122: 2539-2549). Unfortunately, most other immunotherapeutics are either cellular or protein based therapies that are either difficult to administer (require injection or infusion), expensive, or both.

It has been previously shown that sustained loss of SHIP1 signaling results in T cell dysfunction as well as NK cell hyporesponsiveness despite increased activation of signaling pathways that promote effector function. Disclosed herein are compounds and methods that demonstrate that transient and pulsatile inhibition of SHIP1 not only results in increased NK cell numbers and maturation, but also increased NK cell responsiveness, consistent with the disarming hypothesis of NK cell education (Fernandez, N. C. et al., A subset of natural killer cells achieves self-tolerance without expressing inhibitory receptors specific for self-MHC molecules, Blood, (2005); 105: 4416-4423). Additionally, the compounds and methods disclosed herein demonstrate that in vivo SHIP inhibitor treatment promotes increased activation and TcR responsiveness by CD8 T cells. The increased responsiveness of cytotoxic lymphocytes promoted by SHIP inhibitor includes increased cytokine production, T cell responsiveness and NK and T cell mediated clearance of tumor cells resulting in significantly increased survival of tumor bearing hosts or reduced tumor growth. These data demonstrate that SHIP inhibitor is not only able to directly induce apoptosis of malignant cells, but can also activate an immune response that, in some cases, culminates in long-term immunological memory towards the tumor. Thus, small molecule SHIP1 inhibition (SHIP inhibitor) acts as a novel and potent chemo-immunotherapeutic capable of both directly killing tumor cells while simultaneously promoting increased efficacy of NK and T cell tumor responses.

Provided herein are compounds, e.g., the compounds of formulas I, II, III, IV, or V, 8-((2-aminoethyl)amino)naphthalene-1-sulfonic acid, or pharmaceutically acceptable salts or solvates thereof, that are useful in the treatment hematopoietic malignancies, non-hematologic malignancies (e.g. epithelial malignancies), and anemia in a subject in need thereof. Additionally, provided herein are compounds, e.g., the compounds of formulas I, II, III, IV, or V, 8-((2-aminoethyl)amino)naphthalene-1-sulfonic acid, or pharmaceutically acceptable salts or solvates thereof, that are useful for activating natural killer cells and T cells in a subject in need thereof.

Without being bound to any particular mechanism of action, these compounds are believed to selectively inhibit SHIP1 activity, thereby resulting in direct cytotoxicity against cancers and/or activating NK cell and/or T cell activity against cancers. This is consistent with the different tissue expression and biological effects of SHIP2, which has been shown to be a negative regulator of the insulin-signaling pathway (Viemes et al., Discovery and development of small molecule SHIP phosphatase modulators, Med Res Rev, (2014); 34(4): 795-824). SHIP2 selective inhibitors should not be used for the treatments described herein.

In one embodiment, the compounds described herein are suitable for monotherapy and are effective selectively inhibiting SHIP1. In another embodiment, the compounds described herein are suitable for use in a combination therapy.

DEFINITIONS

Listed below are definitions of various terms used to describe this invention. These definitions apply to the terms as they are used throughout this specification and claims, unless otherwise limited in specific instances, either individually or as part of a larger group.

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry, and peptide chemistry are those well-known and commonly employed in the art.

As used herein, the articles "a" and "an" refer to one or to more than one (i.e. to at least one) of the grammatical object of the article. By way of example, "an element" means one element or more than one element. Furthermore, use of the term "including" as well as other forms, such as "include", "includes," and "included," is not limiting.

As used herein, the term "about" will be understood by persons of ordinary skill in the art and will vary to some extent on the context in which it is used. As used herein when referring to a measurable value such as an amount, a temporal duration, and the like, the term "about" is meant to encompass variations of ±10%, including ±5%, ±1%, and ±0.1% from the specified value, as such variations are appropriate to perform the disclosed methods.

As used herein, the term "treatment" or "treating" is defined as the application or administration of a therapeutic agent, i.e., a SHIP1 inhibitor (alone or in combination with another pharmaceutical agent), to a patient, or application or administration of a therapeutic agent.

A "therapeutically effective amount" is that amount that will generate the desired therapeutic outcome (i.e., achieve therapeutic efficacy). For example, a therapeutically effective dose of a compound of the present disclosure is an amount that is sufficient to palliate, ameliorate, stabilize, reverse, prevent, slow or delay the progression of the disease state (e.g., cancer). A therapeutically effective amount can be an amount administered in a dosage protocol that includes days or weeks of administration. In certain embodiments, a therapeutically effective dose of a compound is able to improve at least one sign or symptom of a disease state. As used herein, the terms "effective amount," and "pharmaceutically effective amount," have the same meaning as "therapeutically effective amount".

As used herein, the term "patient," "individual" or "subject" refers to a human or a non-human mammal. Non-human mammals include, for example, livestock and pets, such as ovine, bovine, porcine, canine, feline and murine mammals. Non-human mammals also include non-human primates, rats, rabbits and camelids. In certain embodiments, the patient, subject, or individual is human.

As used herein, the term "mammalian cell" refers to a subset of eukaryotic cells useful in the invention as host cells, and includes human cells, and animal cells such as those from dogs, cats, cattle, horses, rabbits, rats, non-human primates, camelids, mice, goats, pigs, etc. The cells used can be genetically unaltered or can be genetically altered, for example, by transformation with appropriate expression vectors, marker genes, and the like. Mammalian cells suitable for the method of the invention are any mammalian cell capable of expressing the genes of interest, or any mammalian cells that can express a cDNA library, cRNA library, genomic DNA library or any protein or polypeptide useful in the method of the invention. Mammalian cells also include cells from cell lines such as those immortalized cell lines available from the American Type Culture Collection (ATCC). Such cell lines include, for example, rat pheochromocytoma cells (PC12 cells), embryonal carcinoma cells (P19 cells), Chinese hamster ovary (CHO) cells, HeLa cells, baby hamster kidney (BHK) cells, monkey kidney cells (COS), human hepatocellular carcinoma cells (e.g., Hep G2), human embryonic kidney cells, mouse sertoli cells, canine kidney cells, buffalo rat liver cells, human lung cells, human liver cells, mouse mammary tumor cells, as well as others. Also included are hematopoetic stem cells, neuronal stem cells such as neuronal sphere cells, and pluripotent or embryonic stem cells (ES cells).

As used herein, the term "activated T cell" refers to T cells that have been stimulated to increase cytokine production, cell proliferation, cytotoxic activity and/or cell differentiation. T cell activation may be induced by other cells (e.g. NK cells) that secrete cytokines, or by other molecules such as compounds disclosed herein.

As used herein, the term "activated NK cell" refers to natural killer (NK) cells that have been stimulated to increase cytokine production (e.g. IFN-γ), increased cytotoxic activity by the NK cells, and/or NK cell proliferation. NK cell activation may be induced by other cells that secrete cytokines, or by other molecules such as compounds disclosed herein.

As used herein, the phrases "selective inhibition" or "selectively inhibit" refer to a molecule's ability to inhibit the activity or expression of a particular enzyme or enzyme isoform while being unable to inhibit the enzymatic activity or expression of another enzyme or enzyme isoform by more than 5%. For example, a molecule that selectively inhibits SHIP1 could inhibit the enzymatic activity of SHIP1 (e.g. reduce the activity of SHIP1 by 45%) but would only be able to inhibit the enzymatic activity of isoform SHIP2 by 5% or less).

As used herein, the term "pharmaceutically acceptable" refers to a material, such as a carrier or diluent, which does not abrogate the biological activity or properties of the compound, and is relatively non-toxic, i.e., the material may be administered to an individual without causing undesirable biological effects or interacting in a deleterious manner with any of the components of the composition in which it is contained.

As used herein, the term "pharmaceutically acceptable salt" refers to derivatives of the SHIP1 inhibitors wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, p. 1418 and Journal of Pharmaceutical Science, 66, 2 (1977), each of which is incorporated herein by reference in its entirety.

As used herein, the term "solvate" refers to complexes of the compounds disclosed herein or salts thereof with solvent molecules, e.g. organic solvent molecules and/or water.

As used herein, the term "protecting group" by itself or a part of another substitution, unless otherwise stated, includes, but is not limited to the protecting groups for amines delineated in Wuts and Greene, Protective Groups in Organic Synthesis, 4th ed., John Wiley & Sons: New Jersey, pages 696-887 (and, in particular, pages 872-887) (2007), which is incorporated herein by reference in its entirety. Examples of a protecting group include, but are not limited to, benzyloxycarbonyl (Cbz), 2,2,2-trichloroethoxycarbonyl (Troc), 2-(trimethylsilyl)ethoxycarbonyl (Teoc), 2-(4-trifluoromethylphenylsulfonypethoxycarbonyl (Tsc), t-butoxycarbonyl (BOC), 1-adamantyloxycarbonyl (Adoc), 2-adamantylcarbonyl (2-Adoc), 2,4-dimethylpent-3-yloxycarbonyl (Doc), cyclohexyloxycarbonyl (Hoc), 1,1-dimethyl-2,2,2-trichloroethoxycarbonyl (TcBOC), vinyl, 2-chloroethyl, 2-phenylsulfonylethyl, phenylsulfonylethyl, allyl, benzyl, 2-nitrobenzyl, 4-nitrobenzyl, diphenyl-4-pyridylmethyl, N',N'-dimethylhydrazinyl, methoxymethyl, t-butoxymethyl (Bum), benzyloxymethyl (BOM), or 2-tetrahydropyranyl (THP).

As used herein, the term "alkyl," by itself or as part of another substituent means, unless otherwise stated, a straight or branched chain hydrocarbon having the number of carbon atoms designated (i.e., $C_0$-$C_6$-alkyl means null or an alkyl having one to six carbon atoms) and includes straight and branched chains. Examples include methyl, ethyl, propyl, isopropyl, butyl, isobutyl, tert-butyl, pentyl, neopentyl, and hexyl. Other examples of $C_1$-$C_6$-alkyl include ethyl, methyl, isopropyl, isobutyl, n-pentyl, and n-hexyl.

As used herein, the term "heteroalkyl" by itself or in combination with another term means, unless otherwise stated, a stable straight or branched chain alkyl group consisting of the stated number of carbon atoms and one or two heteroatoms selected from the group consisting of O, N, and S, and wherein the nitrogen and sulfur atoms may be optionally oxidized and the nitrogen heteroatom may be optionally quaternized. The heteroatom(s) may be placed at any position of the heteroalkyl group, including between the rest of the heteroalkyl group and the fragment to which it is attached, as well as attached to the most distal carbon atom in the heteroalkyl group. Examples include: —O—$CH_2$—$CH_2$—$CH_3$, —$CH_2$—$CH_2$—$CH_2$—OH, —$CH_2$—$CH_2CH_2$—NH—$CH_3$, —$CH_2$—S—$CH_2$—$CH_3$, and —$CH_2CH_2$—S(=O)—$CH_3$. Up to two heteroatoms may be consecutive, such as, for example, —$CH_2$—NH—$OCH_3$, or —$CH_2$—$CH_2$—S—S—$CH_3$. Preferred heteroalkyl groups have 1-12 carbons.

As used herein, the term "alkenyl," denotes a monovalent group derived from a hydrocarbon moiety containing at least two carbon atoms and at least one carbon-carbon double bond. The double bond may or may not be the point of attachment to another group. Alkenyl groups (e.g., $C_2$-$C_8$-alkenyl) include, but are not limited to, for example, ethenyl, propenyl, prop-1-en-2-yl, butenyl, 1-methyl-2-buten-1-yl, heptenyl, octenyl and the like.

As used herein, the term "halo" or "halogen" alone or as part of another substituent means, unless otherwise stated, a fluorine, chlorine, bromine, or iodine atom, preferably, fluorine, chlorine, or bromine, more preferably, fluorine or chlorine.

As used herein, the term "haloalkyl" refers to alkl radicals wherein any one or more of the alkyl carbon atoms is substituted with halo as defined above. Haloalkyl embraces monohaloalkyl, dihaloalkyl, and polyhaloalkyl radicals. The term "haloalkyl" includes, but is not limited to, fluoromethyl, difluoromethyl, trifluoromethyl, chloromethyl, dichloromethyl, trichloromethyl, and pentafluoroethyl.

As used herein, the term "cycloalkyl" refers to a mono cyclic or polycyclic non-aromatic radical, wherein each of the atoms forming the ring (i.e., skeletal atoms) is a carbon atom. In one embodiment, the cycloalkyl group is saturated or partially unsaturated. In another embodiment, the cycloalkyl group is fused with an aromatic ring. Cycloalkyl groups include groups having 3 to 10 ring atoms ($C_3$-$C_{10}$-cycloalkyl), groups having 3 to 8 ring atoms ($C_3$-$C_8$-cycloalkyl), groups having 3 to 7 ring atoms ($C_3$-$C_7$-cycloalkyl), and groups having 3 to 6 ring atoms ($C_3$-$C_6$-cycloalkyl). Monocyclic cycloalkyls include, but are not limited to, cyclopropyl, cyclobutyl, cyclopentyl, cyclohexyl, cycloheptyl, and cyclooctyl. Dicyclic cycloalkyls include, but are not limited to, tetrahydronaphthyl, indanyl, and tetrahydropentalene. Polycyclic cycloalkyls include adamantine and norbornane. The term cycloalkyl includes unsaturated nonaromatic cyclic groups, which contain at least one carbon carbon double bond or one carbon carbon triple bond.

As used herein, the term "heterocycloalkyl" or "heterocyclyl" refers to a heteroalicyclic group containing one to four ring heteroatoms each selected from O, S, and N. In one embodiment, each heterocyclyl group has from 3 to 10 atoms in its ring system, with the proviso that the ring of said group does not contain two adjacent O or S atoms. Heterocyclyl substituents may be alternatively defined by the number of carbon atoms, e.g., $C_2$-$C_8$-heterocyclyl indicates the number of carbon atoms contained in the heterocyclic group without including the number of heteroatoms. For example, a $C_2$-$C_8$-heterocyclyl will include an additional one to four heteroatoms. Preferbably, the heterocyclyl group has less than three heteroatoms. More preferably, the heterocyclyl group has one to two heteroatoms. In another embodiment, the heterocycloalkyl group is fused with an aromatic ring. In one embodiment, the nitrogen and sulfur heteroatoms may be optionally oxidized, and the nitrogen atom may be optionally quaternized. The heterocyclic system may be attached, unless otherwise stated, at any heteroatom or carbon atom that affords a stable structure.

An example of a 3-membered heterocyclyl group includes, and is not limited to, aziridine. Examples of 4-membered heterocycloalkyl groups include, and are not limited to, azetidine and a beta lactam. Examples of 5-membered heterocyclyl groups include, and are not limited to, pyrrolidine, oxazolidine and thiazolidinedione. Examples of 6-membered heterocycloalkyl groups include, and are not limited to, piperidine, morpholine, and piperazine.

Other non-limiting examples of heterocyclyl groups include monocyclic groups such as aziridine, oxirane, thiirane, azetidine, oxetane, thietane, pyrrolidine, pyrroline, pyrazolidine, imidazoline, dioxolane, sulfolane, 2,3-dihydrofuran, 2,5-dihydrofuran, tetrahydrofuran, thiophane, piperidine, 1,2,3,6-tetrahydropyridine, 1,4-dihydropyridine, piperazine, morpholine, thiomorpholine, pyran, 2,3-dihydropyran, tetrahydropyran, 1,4-dioxane, 1,3-dioxane, homopiperazine, homopiperidine, 1,3-dioxepane, 4,7-dihydro-1,3-dioxepin, and hexamethyleneoxide.

As used herein, the term "spiro-heterocycle" refers to bicyclic structures that may be bridged or spirocyclic in nature with each individual ring within the bicycle varying from 3-8 atoms, and containing 0, 1, or 2 N, O, or S atoms. The term also specifically includes, but is not limited to, 6-oxa-3-azabicyclo[3.1.1]heptanyl, 2-azaspiro[3.3]heptanyl, 2-oxa-6-azaspiro[3.3]heptanyl, 2-oxaspiro[3.3]heptanyl, 2-oxaspiro[3.5]nonanyl, 3-oxaspiro[5.3]nonanyl, and 8-oxabicyclo[3.2.1]octanyl, and the like.

As used herein, the term "aromatic" refers to a carbocycle or heterocycle with one or more polyunsaturated rings and having aromatic character, i.e., having (4n+2) delocalized π (pi) electrons, where n is an integer.

As used herein, the term "aryl," employed alone or in combination with other terms, means, unless otherwise stated, a carbocyclic aromatic system containing one or more rings (typically one, two, or three rings), wherein such rings may be attached together in a pendent manner, such as a biphenyl, or may be fused, such as naphthalene. Examples of aryl groups include phenyl, anthracyl, and naphthyl. Preferred examples are phenyl (e.g., $C_6$-aryl) and biphenyl (e.g., $C_{12}$-aryl). In some embodiments, aryl groups have from six to sixteen carbon atoms. In some embodiments, aryl groups have from six to twelve carbon atoms (e.g., $C_6$-$C_{12}$-aryl). In some embodiments, aryl groups have six carbon atoms (e.g., $C_6$-aryl).

As used herein, the term "heteroaryl" or "heteroaromatic" refers to a heterocycle having aromatic character. Heteroaryl substituents may be defined by the number of carbon atoms, e.g., $C_1$-$C_9$-heteroaryl indicates the number of carbon atoms contained in the heteroaryl group without including the number of heteroatoms. For example, a $C_1$-$C_9$-heteroaryl will include an additional one to four heteroatoms. Preferbably, the heteroaryl group has less than three heteroatoms. More preferably, the heteroaryl group has one to two heteroatoms. A polycyclic heteroaryl may include one or more rings that are partially saturated. Non-limiting examples of heteroaryls include pyridyl, pyrazinyl, pyrimidinyl (including, e.g., 2- and 4-pyrimidinyl), pyridazinyl, thienyl, furyl, pyrrolyl (including, e.g., 2-pyrrolyl), imidazolyl, thiazolyl, oxazolyl, pyrazolyl (including, e.g., 3- and 5-pyrazolyl), isothiazolyl, 1,2,3-triazolyl, 1,2,4-triazolyl, 1,3,4-triazolyl, tetrazolyl, 1,2,3-thiadiazolyl, 1,2,3-oxadiazolyl, 1,3,4-thiadiazolyl and 1,3,4-oxadiazolyl.

Non-limiting examples of polycyclic heterocycles and heteroaryls include indolyl (including, e.g., 3-, 4-, 5-, 6- and 7-indolyl), indolinyl, quinolyl, tetrahydroquinolyl, isoquinolyl (including, e.g., 1- and 5-isoquinolyl), 1,2,3,4-tetrahydroisoquinolyl, cinnolinyl, quinoxalinyl (including, e.g., 2- and 5-quinoxalinyl), quinazolinyl, phthalazinyl, 1,8-naphthyridinyl, 1,4-benzodioxanyl, coumarin, dihydrocoumarin, 1,5-naphthyridinyl, benzofuryl (including, e.g., 3-, 4-, 5-, 6- and 7-benzofuryl), 2,3-dihydrobenzofuryl, 1,2-benzisoxazolyl, benzothienyl (including, e.g., 3-, 4-, 5-, 6-, and 7-benzothienyl), benzoxazolyl, benzothiazolyl (including, e.g., 2-benzothiazolyl and 5-benzothiazolyl), purinyl, benzimidazolyl (including, e.g., 2-benzimidazolyl), benzotriazolyl, thioxanthinyl, carbazolyl, carbolinyl, acridinyl, pyrrolizidinyl, and quinolizidinyl.

As used herein, the term "substituted" means that an atom or group of atoms has replaced hydrogen as the substituent attached to another group.

As used herein, the terminology "selected from . . . " (e.g., "$R^4$ is selected from A, B and C") is understood to be equivalent to the terminology "selected from the group consisting of . . . " (e.g., "$R^4$ is selected from the group consisting of A, B and C").

The term "inositol polyphosphate 5-phosphatase" as used herein refers to a family of phosphatases each of which removes the 5 phosphate from inositol- and phosphatidylinositol-polyphosphates.

The term "SHIP" as used herein refers to SH2-containing inositol-5-phosphatase. SHIP may have an apparent molecular weight of about 145 kDa and is expressed in at least hemopoietic cells. It contains an amino-terminal src-homology domain (SH2), a central 5'-phosphoinositol phosphatase domain, two phosphotyrosine binding consensus sequences, and a proline-rich region at the carboxyl tail.

The term "SHIP1" as used herein refers to a SHIP protein isoform encoded by the gene INPP5D (Accession No. NG_033988.1). SHIP1 has two protein isoforms, an "a" isoform of 1189 amino acids (Accession No. NP 001017915.1) and a "b" isoform of 1188 amino acids (Accession No. NP 005532.2). SHIP1 is expressed by hematopoietic-derived cells, osteoblasts, and mesenchymal cells. SHIP1 has been shown to act as a negative controller in immunoreceptor signaling, as a negative controller in hematopoietic progenitor cell proliferation and survival, and as an inducer of cellular apoptosis (Viernes et al., Discovery and development of small molecule SHIP phosphatase modulators. Med Res Rev. (2014); 34(4): 795-824).

The term "SHIP2" as used herein refers to a SHIP protein isoform of 1258 amino acids (Accession No. NP_001558.3)

encoded by the gene INPPL1 (Accession No. NG_023253.1). SHIP 2 is expressed across all cell and tissue types, with high levels of SHIP2 being expressed in the heart, skeletal muscle, and placenta. SHIP2 has been shown to be a negative regulator of the insulin-signaling pathway. (Viernes et al., Discovery and development of small molecule SHIP phosphatase modulators. Med Res Rev. (2014); 34(4): 795-824).

Compounds That Inhibit SHIP1

Provided herein are compounds having the structure of Formula I:

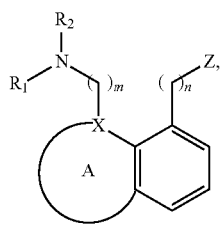
(I)

or a pharmaceutically acceptable salt or solvate thereof, wherein

A is $C_2$-$C_{12}$ aryl, $C_2$-$C_{12}$ heteroaryl, $C_1$-$C_{12}$ heteroalkyl, or absent;

X is C or $C(R_3)$;

$R_1$ is $C_1$-$C_6$alkyl-$N(R_4)(R_5)$, wherein the alkyl is optionally substituted with 1, 2, or 3 groups, each independently selected from $C_1$-$C_{12}$ alkyl or $C_0$-$C_{12}$ alkyl($C_6$-$C_{12}$ aryl);

$R_2$ is H or $C_1$-$C_6$alkyl;

$R_3$ is H or $C_6$-$C_{12}$ aryl;

$R_4$ is H or $C_1$-$C_6$alkyl;

$R_5$ is H or $C_1$-$C_6$alkyl, wherein $R_2$ and $R_5$ are taken together from the nitrogen atoms to which they are bound to form a heterocycle or spiro-heterocycle;

Z is —$S(O)_2OR_6$, —$S(O)_2N(R_7)(R_8)$, —$P(O)_2OR_9$, —$P(S)(OR_{10})_2$, or —$S(O)_2R_{11}$;

$R_6$ is $C_1$-$C_{12}$alkyl, $C_{12}$alkenyl, —$C(O)C_1$-$C_{12}$alkyl, —$C(O)OC_1$-$C_{12}$alkyl, —$C(O)N(C_1$-$C_{12}$alkyl$)_2$ or $C_6$-$C_{12}$ aryl, wherein alkyl, alkenyl, and aryl are optionally substituted with 1, 2, or 3 groups, each independently selected from halo, —OH, $C_1$-$C_6$alkyl, $C_1$-$C_6$-haloalkyl, —O-$C_1$-$C_6$alkyl, —$NO_2$, —$N(H)(R_{12})$, and —CN;

$R_7$ is H, $C_1$-$C_6$alkyl, or $C_1$-$C_6$alkenyl, wherein alkyl and alkenyl are optionally substituted with 1, 2, or 3 groups, each independently selected from halo, —OH, $C_1$-$C_6$alkyl, $C_1$-$C_6$-haloalkyl, —O—$C_1$-$C_6$alkyl, —$NO_2$, —$N(H)(R_{12})$, and —CN;

$R_8$ is H, $C_1$-$C_6$alkyl, or $C_1$-$C_6$alkenyl, wherein alkyl and alkenyl are optionally substituted with 1, 2, or 3 groups, each independently selected from halo, —OH, $C_1$-$C_6$alkyl, $C_1$-$C_6$-haloalkyl, —O—$C_1$-$C_6$alkyl, —$NO_2$, —$N(H)(R_{12})$, and —CN;

$R_9$ is H, $C_1$-$C_{12}$alkyl, or $C_1$-$C_{12}$alkenyl, —$C(O)C_1$-$C_{12}$alkyl, —$C(O)OC_1C_{12}$alkyl, —$C(O)N(C_1$-$C_{12}$alkyl$)_2$ or $C_6$-$C_{12}$ aryl, alkenyl, and aryl are optionally substituted with 1, 2, or 3 groups, each independently selected from halo, —OH, $C_1$-$C_6$alkyl, $C_1$-$C_6$-haloalkyl, —O—$C_1$-$C_6$alkyl, —$NO_2$, —$N(H)(R_{12})$, and —CN;

$R_{10}$ is H, $C_1$-$C_{12}$alkyl, or $C_1$-$C_{12}$alkenyl, —$C(O)C_1$-$C_{12}$alkyl, —$C(O)OC_1C_{12}$alkyl, —$C(O)N(C_1$-$C_{12}$alkyl$)_2$ or $C_6$-$C_{12}$ aryl, alkenyl, and aryl are optionally substituted with 1, 2, or 3 groups, each independently selected from halo, —OH, $C_1$-$C_6$alkyl, $C_1$-$C_6$-haloalkyl, —O—$C_1$-$C_6$alkyl, —$NO_2$, —$N(H)(R_{12})$, and —CN;

$R_{11}$ is $C_1$-$C_{12}$alkyl, or $C_1$-$C_{12}$alkenyl, —$C(O)C_1$-$C_{12}$alkyl, —$C(O)OC_1C_{12}$alkyl, —$C(O)N(C_1$-$C_{12}$alkyl$)_2$ or $C_6$-$C_{12}$ aryl, wherein alkyl, alkenyl, and aryl are optionally substituted with 1, 2, or 3 groups, each independently selected from halo, —OH, $C_1$-$C_6$alkyl, $C_1$-$C_6$-haloalkyl, —O—$C_1$-$C_6$alkyl, —$NO_2$, —$N(H)(R_{12})$, and —CN; wherein $R_{11}$ is optionally taken together with $R_1$ to form a covalent bond;

$R_{12}$ is a protecting group;

n is 0 or 1; and m is 0 or 1.

In an embodiment, the compound of Formula I is a compound of Formula II:

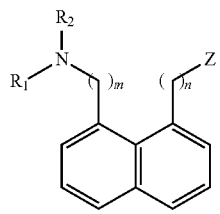
(II)

or a pharmaceutically acceptable salt or solvate thereof, wherein $R_1$ is $C_1$-$C_6$alkyl-$N(R_4)(R_5)$, wherein the alkyl is optionally substituted with 1, 2, or 3 groups, each independently selected from $C_1$-$C_{12}$ alkyl or $C_0$-$C_{12}$ alkyl($C_6$-$C_{12}$ aryl);

$R_2$ is H or $C_1$-$C_6$alkyl;

$R_4$ is H or $C_1$-$C_6$alkyl;

$R_5$ is H or $C_1$-$C_6$alkyl, wherein $R_2$ and $R_5$ are taken together from the nitrogen atoms to which they are bound to form a heterocycle or spiro-heterocycle;

Z is —$S(O)_2OR_6$, —$S(O)_2N(R_7)(R_8)$, —$P(O)_2OR_9$, —$P(S)(OR_{10})_2$, or —$S(O)_2R_{11}$;

$R_6$ is $C_1$-$C_{12}$alkyl, $C_{12}$alkenyl, —$C(O)C_1$-$C_{12}$alkyl, —$C(O)OC_1$-$C_{12}$alkyl, —$C(O)N(C_1$-$C_{12}$alkyl$)_2$ or $C_6$-$C_{12}$ aryl, wherein alkyl, alkenyl, and aryl are optionally substituted with 1, 2, or 3 groups, each independently selected from halo, —OH, $C_1$-$C_6$alkyl, $C_1$-$C_6$-haloalkyl, —O-$C_1$-$C_6$alkyl, —$NO_2$, —$N(H)(R_{12})$, and —CN;

$R_7$ is H, $C_1$-$C_6$alkyl, or $C_1$-$C_6$alkenyl, wherein alkyl and alkenyl are optionally substituted with 1, 2, or 3 groups, each independently selected from halo, —OH, $C_1$-$C_6$alkyl, $C_1$-$C_6$-haloalkyl, —O—$C_1$-$C_6$alkyl, —$NO_2$, —$N(H)(R_{12})$, and —CN;

$R_8$ is H, $C_1$-$C_6$alkyl, or $C_1$-$C_6$alkenyl, wherein alkyl and alkenyl are optionally substituted with 1, 2, or 3 groups, each independently selected from halo, —OH, $C_1$-$C_6$alkyl, $C_1$-$C_6$-haloalkyl, —O—$C_1$-$C_6$alkyl, —$NO_2$, —$N(H)(R_{12})$, and —CN;

$R_9$ is H, $C_1$-$C_{12}$alkyl, or $C_1$-$C_{12}$alkenyl, —$C(O)C_1$-$C_{12}$alkyl, —$C(O)OC_1C_{12}$alkyl, —$C(O)N(C_1$-$C_{12}$alkyl$)_2$ or $C_6$-$C_{12}$ aryl, alkenyl, and aryl are optionally substituted with 1, 2, or 3 groups, each independently selected from halo, —OH, $C_1$-$C_6$alkyl, $C_1$-$C_6$-haloalkyl, —O—$C_1$-$C_6$alkyl, —$NO_2$, —$N(H)(R_{12})$, and —CN;

$R_{10}$ is H, $C_1$-$C_{12}$alkyl, or $C_1$-$C_{12}$alkenyl, —$C(O)C_1$-$C_{12}$alkyl, —$C(O)OC_1C_{12}$alkyl, —$C(O)N(C_1$-$C_{12}$alkyl$)_2$ or $C_6$-$C_{12}$ aryl, alkenyl, and aryl are optionally substituted with 1, 2, or 3 groups, each independently selected from halo, —OH, $C_1$-$C_6$alkyl, $C_1$-$C_6$-haloalkyl, —O—$C_1$-$C_6$alkyl, —$NO_2$, —$N(H)(R_{12})$, and —CN;

$R_{11}$ is $C_1$-$C_{12}$alkyl, or $C_1$-$C_{12}$alkenyl, —C(O)$C_1$-$C_{12}$alkyl, —C(O)O$C_1C_{12}$alkyl, —C(O)N($C_1$-$C_{12}$alkyl)$_2$ or $C_6$-$C_{12}$ aryl, wherein alkyl, alkenyl, and aryl are optionally substituted with 1, 2, or 3 groups, each independently selected from halo, —OH, $C_1$-$C_6$alkyl, $C_1$-$C_6$-haloalkyl, —O—$C_1$-$C_6$alkyl, —NO$_2$, —N(H)($R_{12}$), and —CN; wherein $R_{11}$ is optionally taken together with $R_1$ to form a covalent bond;

$R_{12}$ is a protecting group;

n is 0 or 1; and m is 0 or 1.

In an embodiment, Z is —S(O)$_2$O$R_6$, —S(O)$_2$N($R_7$)($R_8$), or —P(O)$_2$O$R_9$.

In another embodiment, Z is —S(O)$_2$O$R_6$.

In yet another embodiment, Z is —S(O)$_2$O$R_6$; and $R_6$ is $C_6$-$C_{12}$alkyl or $C_6$-$C_{12}$ aryl, wherein alkyl and aryl are optionally substituted with 1, 2, or 3 groups, each independently selected from halo, —OH, $C_1$-$C_6$-alkyl, $C_1$-$C_6$-haloalkyl, —O-$C_1$-$C_6$alkyl, —NO$_2$, —N(H)($R_{12}$), and —CN.

In a further embodiment, $R_1$ is $C_1$-$C_6$alkyl-N($R_4$)($R_5$), wherein the alkyl is optionally substituted with 1, 2, or 3 groups, each independently selected from $C_1$-$C_{12}$ alkyl or $C_0$-$C_{12}$ alkyl($C_6$-$C_{12}$ aryl); $R_2$ is H; $R_4$ is H; $R_5$ is H or $C_1$-$C_6$alkyl, wherein $R_2$ and $R_5$ are taken together from the nitrogen atoms to which they are bound to form a heterocycle or spiro-heterocycle.

In still another embodiment, $R_1$ is $C_1$-$C_6$alkyl-N($R_4$)($R_5$); $R_2$ is H; $R_4$ is H; and $R_5$ is H.

In an embodiment, $R_1$ is —CH$_2$CH$_2$NH$_2$; and $R_2$ is H.

In an embodiment, Z is —S(O)$_2$O$R_6$, $R_6$ is $C_1$-$C_{12}$alkyl or $C_6$-$C_{12}$ aryl, wherein alkyl and aryl are optionally substituted with 1, 2, or 3 groups, each independently selected from halo, —OH, $C_1$-$C_6$-alkyl, $C_1$-$C_6$-haloalkyl, —O-$C_1$-$C_6$-alkyl, —NO$_2$, —N(H)($R_{12}$), and —CN; $R_1$ is $C_1$-$C_6$alkyl-N($R_4$)($R_5$), wherein the alkyl is optionally substituted with 1, 2, or 3 groups, each independently selected from $C_1$-$C_{12}$ alkyl or $C_0$-$C_{12}$ alkyl($C_6$-$C_{12}$ aryl); $R_2$ is H; $R_4$ is H; $R_5$ is H or $C_1$-$C_6$alkyl, wherein $R_2$ and $R_5$ are taken together from the nitrogen atoms to which they are bound to form a heterocycle or spiro-heterocycle; n is 0; and m is 0.

In an embodiment, Z is —S(O)$_2$O$R_6$, $R_6$ is $C_1$-$C_{12}$alkyl or $C_6$-$C_{12}$ aryl, wherein alkyl and aryl are optionally substituted with 1, 2, or 3 groups, each independently selected from halo, —OH, $C_1$-$C_6$-alkyl, $C_1$-$C_6$-haloalkyl, —O-$C_1$-$C_6$-alkyl, —NO$_2$, —N(H)($R_{12}$), and —CN; $R_1$ is $C_1$-$C_6$alkyl-N($R_4$)($R_5$), wherein the alkyl is optionally substituted with 1, 2, or 3 groups, each independently selected from $C_1$-$C_{12}$ alkyl or $C_0$-$C_{12}$ alkyl($C_6$-$C_{12}$ aryl); $R_2$ is H; $R_4$ is H; $R_5$ is H or $C_1$-$C_6$alkyl, wherein $R_2$ and $R_5$ are taken together from the nitrogen atoms to which they are bound to form a heterocycle or spiro-heterocycle; n is 0; and m is 0.

In another embodiment, Z is —S(O)$_2$O$R_6$; $R_6$ is $C_1$-$C_{12}$alkyl or $C_6$-$C_{12}$ aryl, wherein alkyl and aryl are optionally substituted with 1, 2, or 3 groups, each independently selected from halo, —OH, $C_1$-$C_6$alkyl, $C_1$-$C_6$-haloalkyl, —O—$C_1$-$C_6$alkyl, —NO$_2$, —N(H)($R_{12}$), and —CN; $R_1$ is —CH$_2$CH$_2$NH$_2$; $R_2$ is H; n is 0; and m is 0.

In yet another embodiment, n is 0; and m is 0.

Also provided herein are compounds having the structure of Formula III:

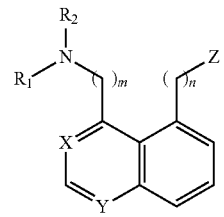

(III)

or a pharmaceutically acceptable salt or solvate thereof, wherein

X is N or C(H);

Y is N or C(H);

$R_1$ is $C_1$-$C_6$alkyl-N($R_4$)($R_5$), wherein the alkyl is optionally substituted with 1, 2, or 3 groups, each independently selected from $C_1$-$C_{12}$ alkyl or $C_0$-$C_{12}$ alkyl ($C_6$-$C_{12}$ aryl);

$R_2$ is H or $C_1$-$C_6$alkyl;

$R_4$ is H or $C_1$-$C_6$alkyl;

$R_5$ is H or $C_1$-$C_6$alkyl, wherein $R_2$ and $R_5$ are taken together from the nitrogen atoms to which they are bound to form a heterocycle or spiro-heterocycle;

Z is —S(O)$_2$O$R_6$, —S(O)$_2$N($R_7$)($R_8$), —P(O)$_2$O$R_9$, —P(S)(O$R_{10}$)$_2$, or —S(O)$_2$$R_{11}$;

$R_6$ is $C_1$-$C_{12}$alkyl, $C_{12}$alkenyl, —C(O)$C_1$-$C_{12}$alkyl, —C(O)O$C_1$-$C_{12}$alkyl, —C(O)N($C_1$-$C_{12}$alkyl)$_2$ or $C_6$-$C_{12}$ aryl, wherein alkyl, alkenyl, and aryl are optionally substituted with 1, 2, or 3 groups, each independently selected from halo, —OH, $C_1$-$C_6$alkyl, $C_1$-$C_6$-haloalkyl, —O-$C_1$-$C_6$alkyl, —NO$_2$, —N(H)($R_{12}$), and —CN;

$R_7$ is H, $C_1$-$C_6$alkyl, or $C_1$-$C_6$alkenyl, wherein alkyl and alkenyl are optionally substituted with 1, 2, or 3 groups, each independently selected from halo, —OH, $C_1$-$C_6$alkyl, $C_1$-$C_6$-haloalkyl, —O—$C_1$-$C_6$alkyl, —NO$_2$, —N(H)($R_{12}$), and —CN;

$R_8$ is H, $C_1$-$C_6$alkyl, or $C_1$-$C_6$alkenyl, wherein alkyl and alkenyl are optionally substituted with 1, 2, or 3 groups, each independently selected from halo, —OH, $C_1$-$C_6$alkyl, $C_1$-$C_6$-haloalkyl, —O—$C_1$-$C_6$alkyl, —NO$_2$, —N(H)($R_{12}$), and —CN;

$R_9$ is H, $C_1$-$C_{12}$alkyl, or $C_1$-$C_{12}$alkenyl, —C(O)$C_1$-$C_{12}$alkyl, —C(O)O$C_1C_{12}$alkyl, —C(O)N($C_1$-$C_{12}$alkyl)$_2$ or $C_6$-$C_{12}$ aryl, alkenyl, and aryl are optionally substituted with 1, 2, or 3 groups, each independently selected from halo, —OH, $C_1$-$C_6$alkyl, $C_1$-$C_6$-haloalkyl, —O—$C_1$-$C_6$alkyl, —NO$_2$, —N(H)($R_{12}$), and —CN;

$R_{10}$ is H, $C_1$-$C_{12}$alkyl, or $C_1$-$C_{12}$alkenyl, —C(O)$C_1$-$C_{12}$alkyl, —C(O)O$C_1C_{12}$alkyl, —C(O)N($C_1$-$C_{12}$alkyl)$_2$ or $C_6$-$C_{12}$ aryl, alkenyl, and aryl are optionally substituted with 1, 2, or 3 groups, each independently selected from halo, —OH, $C_1$-$C_6$alkyl, $C_1$-$C_6$-haloalkyl, —O—$C_1$-$C_6$alkyl, —NO$_2$, —N(H)($R_{12}$), and —CN;

$R_{11}$ is $C_1$-$C_{12}$alkyl, or $C_1$-$C_{12}$alkenyl, —C(O)$C_1$-$C_{12}$alkyl, —C(O)O$C_1C_{12}$alkyl, —C(O)N($C_1$-$C_{12}$alkyl)$_2$ or $C_6$-$C_{12}$ aryl, wherein alkyl, alkenyl, and aryl are optionally substituted with 1, 2, or 3 groups, each independently selected from halo, —OH, $C_1$-$C_6$alkyl, $C_1$-$C_6$-haloalkyl, —O—$C_1$-$C_6$alkyl, —NO$_2$, —N(H)($R_{12}$), and —CN; wherein $R_{11}$ is optionally taken together with $R_1$ to form a covalent bond;

$R_{12}$ is a protecting group;

n is 0 or 1; and m is 0 or 1.

In an embodiment, Z is —S(O)$_2$OR$_6$, —S(O)$_2$N(R$_7$)(R$_8$), or —P(O)$_2$OR$_9$.

In another embodiment, Z is —S(O)$_2$OR$_6$.

In yet another embodiment, Z is —S(O)$_2$OR$_6$, and H, C$_1$-C$_{12}$alkyl or C$_6$-C$_{12}$ aryl, wherein alkyl and aryl are optionally substituted with 1, 2, or 3 groups, each independently selected from halo, —OH, C$_1$-C$_6$alkyl, C$_1$-C$_6$-haloalkyl, —O-C$_1$-C$_6$alkyl, —NO$_2$, —N(H)(R$_{12}$), and —CN;

In an embodiment, R$_1$ is C$_1$-C$_6$alkyl-N(R$_4$)(R$_5$), wherein the alkyl is optionally substituted with 1, 2, or 3 groups, each independently selected from C$_1$-C$_{12}$ alkyl or C$_0$-C$_{12}$ alkyl (C$_6$-C$_{12}$ aryl); R$_2$ is H; R$_4$ is H; and R$_5$ is H or C$_1$-C$_6$alkyl, wherein R$_2$ and R$_5$ are taken together from the nitrogen atoms to which they are bound to form a heterocycle or spiro-heterocycle;

In another embodiment, R$_1$ is C$_1$-C$_6$alkyl-N(R$_4$)(R$_5$); R$_2$ is H; R$_4$ is H; and R$_5$ is H.

In yet another embodiment, R$_1$ is —CH$_2$CH$_2$NH$_2$; and R$_2$ is H.

In a further embodiment, Z is —S(O)$_2$OR$_6$, and H, C$_1$-C$_{12}$alkyl or C$_6$-C$_{12}$ aryl, wherein alkyl and aryl are optionally substituted with 1, 2, or 3 groups, each independently selected from halo, —OH, C$_1$-C$_6$alkyl, C$_1$-C$_6$-haloalkyl, —O-C$_1$-C$_6$alkyl, —NO$_2$, —N(H)(R$_{12}$), and —CN; R$_1$ is C$_1$-C$_6$alkyl-N(R$_4$)(R$_5$), wherein the alkyl is optionally substituted with 1, 2, or 3 groups, each independently selected from C$_1$-C$_{12}$ alkyl or C$_0$-C$_{12}$alkyl (C$_6$-C$_{12}$ aryl); R$_2$ is H; R$_4$ is H; and R$_5$ is H or C$_1$-C$_6$alkyl, wherein R$_2$ and R$_5$ are taken together from the nitrogen atoms to which they are bound to form a heterocycle or spiro-heterocycle; n is 0; and m is 0.

In an embodiment, Z is —S(O)$_2$OR$_6$, and H, C$_1$-C$_{12}$alkyl or C$_6$-C$_{12}$ aryl, wherein alkyl and aryl are optionally substituted with 1, 2, or 3 groups, each independently selected from halo, —OH, C$_1$-C$_6$alkyl, C$_1$-C$_6$-haloalkyl, —O-C$_1$-C$_6$alkyl, —NO$_2$, —N(H)(R$_{12}$), and —CN; R$_1$ is —CH$_2$CH$_2$NH$_2$; R$_2$ is H; n is 0; and m is 0.

In an embodiment, X is N or C(H); and Y is N.

In an embodiment, X is N; and Y is N.

In an embodiment, n is 0; and m is 0.

Also provided herein are compounds having the structure of Formula IV:

(IV)

or a pharmaceutically acceptable salt or solvate thereof, wherein

R$_1$ is C$_1$-C$_6$alkyl-N(R$_4$)(R$_5$), wherein the alkyl is optionally substituted with 1, 2, or 3 groups, each independently selected from C$_1$-C$_{12}$ alkyl or C$_0$-C$_{12}$ alkyl(C$_6$-C$_{12}$ aryl);

R$_2$ is H or C$_1$-C$_6$alkyl;

R$_3$ is H or C$_6$-C$_{12}$ aryl;

R$_4$ is H or C$_1$-C$_6$alkyl;

R$_5$ is H or C$_1$-C$_6$alkyl, wherein R$_2$ and R$_5$ are taken together from the nitrogen atoms to which they are bound to form a heterocycle or spiro-heterocycle;

Z is —S(O)$_2$OR$_6$, —S(O)$_2$N(R$_7$)(R$_8$), —P(O)$_2$OR$_9$, —P(S)(OR$_{10}$)$_2$, or —S(O)$_2$R$_{11}$;

R$_6$ is C$_1$-C$_{12}$alkyl, C$_{12}$alkenyl, —C(O)C$_1$-C$_{12}$alkyl, —C(O)OC$_1$-C$_{12}$alkyl, —C(O)N(C$_1$-C$_{12}$alkyl)$_2$ or C$_6$-C$_{12}$ aryl, wherein alkyl, alkenyl, and aryl are optionally substituted with 1, 2, or 3 groups, each independently selected from halo, —OH, C$_1$-C$_6$alkyl, C$_1$-C$_6$-haloalkyl, —O-C$_1$-C$_6$alkyl, —NO$_2$, —N(H)(R$_{12}$), and —CN;

R$_7$ is H, C$_1$-C$_6$alkyl, or C$_1$-C$_6$alkenyl, wherein alkyl and alkenyl are optionally substituted with 1, 2, or 3 groups, each independently selected from halo, —OH, C$_1$-C$_6$alkyl, C$_1$-C$_6$-haloalkyl, —O—C$_1$-C$_6$alkyl, —NO$_2$, —N(H)(R$_{12}$), and —CN;

R$_8$ is H, C$_1$-C$_6$alkyl, or C$_1$-C$_6$alkenyl, wherein alkyl and alkenyl are optionally substituted with 1, 2, or 3 groups, each independently selected from halo, —OH, C$_1$-C$_6$alkyl, C$_1$-C$_6$-haloalkyl, —O—C$_1$-C$_6$alkyl, —NO$_2$, —N(H)(R$_{12}$), and —CN;

R$_9$ is H, C$_1$-C$_{12}$alkyl, or C$_1$-C$_{12}$alkenyl, —C(O)C$_1$-C$_{12}$alkyl, —C(O)OC$_1$C$_{12}$alkyl, —C(O)N(C$_1$-C$_{12}$alkyl)$_2$ or C$_6$-C$_{12}$ aryl, alkenyl, and aryl are optionally substituted with 1, 2, or 3 groups, each independently selected from halo, —OH, C$_1$-C$_6$alkyl, C$_1$-C$_6$-haloalkyl, —O—C$_1$-C$_6$alkyl, —NO$_2$, —N(H)(R$_{12}$), and —CN;

R$_{10}$ is H, C$_1$-C$_{12}$alkyl, or C$_1$-C$_{12}$alkenyl, —C(O)C$_1$-C$_{12}$alkyl, —C(O)OC$_1$C$_{12}$alkyl, —C(O)N(C$_1$-C$_{12}$alkyl)$_2$ or C$_6$-C$_{12}$ aryl, alkenyl, and aryl are optionally substituted with 1, 2, or 3 groups, each independently selected from halo, —OH, C$_1$-C$_6$alkyl, C$_1$-C$_6$-haloalkyl, —O—C$_1$-C$_6$alkyl, —NO$_2$, —N(H)(R$_{12}$), and —CN;

R$_{11}$ is C$_1$-C$_{12}$alkyl, or C$_1$-C$_{12}$alkenyl, —C(O)C$_1$-C$_{12}$alkyl, —C(O)OC$_1$C$_{12}$alkyl, —C(O)N(C$_1$-C$_{12}$alkyl)$_2$ or C$_6$-C$_{12}$ aryl, wherein alkyl, alkenyl, and aryl are optionally substituted with 1, 2, or 3 groups, each independently selected from halo, —OH, C$_1$-C$_6$alkyl, C$_1$-C$_6$-haloalkyl, —O—C$_1$-C$_6$alkyl, —NO$_2$, —N(H)(R$_{12}$), and —CN; wherein R$_{11}$ is optionally taken together with R$_1$ to form a covalent bond;

R$_{12}$ is a protecting group;

n is 0 or 1; and m is 0 or 1.

In an embodiment, Z is —S(O)$_2$OR$_6$, —S(O)$_2$N(R$_7$)(R$_8$), or —P(O)$_2$OR$_9$.

In another embodiment, Z is —S(O)$_2$OR$_6$.

In yet another embodiment, Z is —S(O)$_2$OR$_6$, and H, C$_1$-C$_{12}$alkyl or C$_6$-C$_{12}$ aryl, wherein alkyl and aryl are optionally substituted with 1, 2, or 3 groups, each independently selected from halo, —OH, C$_1$-C$_6$alkyl, C$_1$-C$_6$-haloalkyl, —O-C$_1$-C$_6$alkyl, —NO$_2$, —N(H)(R$_{12}$), and —CN;

In an embodiment, R$_1$ is C$_1$-C$_6$alkyl-N(R$_4$)(R$_5$), wherein the alkyl is optionally substituted with 1, 2, or 3 groups, each independently selected from C$_1$-C$_{12}$ alkyl or C$_0$-C$_{12}$ alkyl (C$_6$-C$_{12}$ aryl); R$_2$ is H; R$_4$ is H; and R$_5$ is H or C$_1$-C$_6$alkyl, wherein R$_2$ and R$_5$ are taken together from the nitrogen atoms to which they are bound to form a heterocycle or spiro-heterocycle;

In another embodiment, R$_1$ is C$_1$-C$_6$alkyl-N(R$_4$)(R$_5$); R$_2$ is H; R$_4$ is H; and R$_5$ is H.

In yet another embodiment, R$_1$ is —CH$_2$CH$_2$NH$_2$; and R$_2$ is H.

In a further embodiment, Z is —S(O)$_2$OR$_6$, and H, C$_1$-C$_{12}$alkyl or C$_6$-C$_{12}$ aryl, wherein alkyl and aryl are optionally substituted with 1, 2, or 3 groups, each independently selected from halo, —OH, C$_1$-C$_6$alkyl, C$_1$-C$_6$-haloalkyl, —O-C$_1$-C$_6$alkyl, —NO$_2$, —N(H)(R$_{12}$), and —CN; R$_1$ is C$_1$-C$_6$alkyl-N(R$_4$)(R$_5$), wherein the alkyl is optionally substituted with 1, 2, or 3 groups, each independently selected from C$_1$-C$_{12}$ alkyl or C$_0$-C$_{12}$alkyl (C$_6$-C$_{12}$ aryl); R$_2$ is H; R$_4$ is H; and R$_5$ is H or C$_1$-C$_6$alkyl, wherein R$_2$ and R$_5$ are taken together from the nitrogen atoms to which they are bound to form a heterocycle or spiro-heterocycle; n is 0; and m is 0.

In an embodiment, Z is —S(O)$_2$OR$_6$, and H, C$_1$-C$_{12}$alkyl or C$_6$-C$_{12}$ aryl, wherein alkyl and aryl are optionally substituted with 1, 2, or 3 groups, each independently selected from halo, —OH, C$_1$-C$_6$alkyl, C$_1$-C$_6$-haloalkyl, —O-C$_1$-C$_6$alkyl, —NO$_2$, —N(H)(R$_{12}$), and —CN; R$_1$ is —CH$_2$CH$_2$NH$_2$; R$_2$ is H; n is 0; and m is 0.

In an embodiment, R$_3$ is H.

In an embodiment, n is 0; and m is 0.

Also provided herein are compounds having the structure of Formula V:

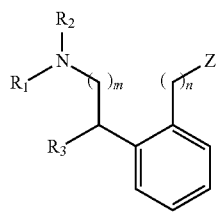

(V)

or a pharmaceutically acceptable salt or solvate thereof, wherein

R$_1$ is C$_1$-C$_6$alkyl-N(R$_4$)(R$_5$), wherein the alkyl is optionally substituted with 1, 2, or 3 groups, each independently selected from C$_1$-C$_{12}$ alkyl or C$_0$-C$_{12}$ alkyl(C$_6$-C$_{12}$ aryl);

R$_2$ is H or C$_1$-C$_6$alkyl;

R$_3$ is H or C$_6$-C$_{12}$ aryl;

R$_4$ is H or C$_1$-C$_6$alkyl;

R$_5$ is H or C$_1$-C$_6$alkyl, wherein R$_2$ and R$_5$ are taken together from the nitrogen atoms to which they are bound to form a heterocycle or spiro-heterocycle;

Z is —S(O)$_2$OR$_6$, —S(O)$_2$N(R$_7$)(R$_8$), —P(O)$_2$OR$_9$, —P(S)(OR$_{10}$)$_2$, or —S(O)$_2$R$_{11}$;

R$_6$ is C$_1$-C$_{12}$alkyl, C$_1$-C$_{12}$alkenyl, —C(O)C$_1$-C$_{12}$alkyl, —C(O)OC$_1$-C$_{12}$alkyl, —C(O)N(C$_1$-C$_{12}$alkyl)$_2$ or C$_6$-C$_{12}$ aryl, wherein alkyl, alkenyl, and aryl are optionally substituted with 1, 2, or 3 groups, each independently selected from halo, —OH, C$_1$-C$_6$alkyl, C$_1$-C$_6$-haloalkyl, —O-C$_1$-C$_6$alkyl, —NO$_2$, —N(H)(R$_{12}$), and —CN;

R$_7$ is H, C$_1$-C$_6$alkyl, or C$_1$-C$_6$alkenyl, wherein alkyl and alkenyl are optionally substituted with 1, 2, or 3 groups, each independently selected from halo, —OH, C$_1$-C$_6$alkyl, C$_1$-C$_6$-haloalkyl, —O—C$_1$-C$_6$alkyl, —NO$_2$, —N(H)(R$_{12}$), and —CN;

R$_8$ is H, C$_1$-C$_6$alkyl, or C$_1$-C$_6$alkenyl, wherein alkyl and alkenyl are optionally substituted with 1, 2, or 3 groups, each independently selected from halo, —OH, C$_1$-C$_6$alkyl, C$_1$-C$_6$-haloalkyl, —O—C$_1$-C$_6$alkyl, —NO$_2$, —N(H)(R$_{12}$), and —CN;

R$_9$ is H, C$_1$-C$_{12}$alkyl, or C$_1$-C$_{12}$alkenyl, —C(O)C$_1$-C$_{12}$alkyl, —C(O)OC$_1$C$_{12}$alkyl, —C(O)N(C$_1$-C$_{12}$alkyl)$_2$ or C$_6$-C$_{12}$ aryl, alkenyl, and aryl are optionally substituted with 1, 2, or 3 groups, each independently selected from halo, —OH, C$_1$-C$_6$alkyl, C$_1$-C$_6$-haloalkyl, —O—C$_1$-C$_6$alkyl, —NO$_2$, —N(H)(R$_{12}$), and —CN;

R$_{10}$ is H, C$_1$-C$_{12}$alkyl, or C$_1$-C$_{12}$alkenyl, —C(O)C$_1$-C$_{12}$alkyl, —C(O)OC$_1$C$_{12}$alkyl, —C(O)N(C$_1$-C$_{12}$alkyl)$_2$ or C$_6$-C$_{12}$ aryl, alkenyl, and aryl are optionally substituted with 1, 2, or 3 groups, each independently selected from halo, —OH, C$_1$-C$_6$alkyl, C$_1$-C$_6$-haloalkyl, —O—C$_1$-C$_6$alkyl, —NO$_2$, —N(H)(R$_{12}$), and —CN;

R$_{11}$ is C$_1$-C$_{12}$alkyl, or C$_1$-C$_{12}$alkenyl, —C(O)C$_1$-C$_{12}$alkyl, —C(O)OC$_1$C$_{12}$alkyl, —C(O)N(C$_1$-C$_{12}$alkyl)$_2$ or C$_6$-C$_{12}$ aryl, wherein alkyl, alkenyl, and aryl are optionally substituted with 1, 2, or 3 groups, each independently selected from halo, —OH, C$_1$-C$_6$alkyl, C$_1$-C$_6$-haloalkyl, —O—C$_1$-C$_6$alkyl, —NO$_2$, —N(H)(R$_{12}$), and —CN; wherein R$_{11}$ is optionally taken together with R$_1$ to form a covalent bond;

R$_{12}$ is a protecting group;

n is 0 or 1; and m is 0 or 1.

In an embodiment, Z is —S(O)$_2$OR$_6$, —S(O)$_2$N(R$_7$)(R$_8$), or —P(O)$_2$OR$_9$.

In another embodiment, Z is —S(O)$_2$OR$_6$.

In yet another embodiment, Z is —S(O)$_2$OR$_6$, and H, C$_1$-C$_{12}$alkyl or C$_6$-C$_{12}$ aryl, wherein alkyl and aryl are optionally substituted with 1, 2, or 3 groups, each independently selected from halo, —OH, C$_1$-C$_6$alkyl, C$_1$-C$_6$-haloalkyl, —O-C$_1$-C$_6$alkyl, —NO$_2$, —N(H)(R$_{12}$), and —CN;

In an embodiment, R$_1$ is C$_1$-C$_6$alkyl-N(R$_4$)(R$_5$), wherein the alkyl is optionally substituted with 1, 2, or 3 groups, each independently selected from C$_1$-C$_{12}$ alkyl or C$_0$-C$_{12}$ alkyl (C$_6$-C$_{12}$ aryl); R$_2$ is H; R$_4$ is H; and R$_5$ is H or C$_1$-C$_6$alkyl, wherein R$_2$ and R$_5$ are taken together from the nitrogen atoms to which they are bound to form a heterocycle or spiro-heterocycle;

In another embodiment, R$_1$ is C$_1$-C$_6$alkyl-N(R$_4$)(R$_5$); R$_2$ is H; R$_4$ is H; and R$_5$ is H.

In yet another embodiment, R$_1$ is —CH$_2$CH$_2$NH$_2$; and R$_2$ is H.

In a further embodiment, Z is —S(O)$_2$OR$_6$, and H, C$_1$-C$_{12}$alkyl or C$_6$-C$_{12}$ aryl, wherein alkyl and aryl are optionally substituted with 1, 2, or 3 groups, each independently selected from halo, —OH, C$_1$-C$_6$alkyl, C$_1$-C$_6$-haloalkyl, —O-C$_1$-C$_6$alkyl, —NO$_2$, —N(H)(R$_{12}$), and —CN; R$_1$ is C$_1$-C$_6$alkyl-N(R$_4$)(R$_5$), wherein the alkyl is optionally substituted with 1, 2, or 3 groups, each independently selected from C$_1$-C$_{12}$ alkyl or C$_0$-C$_{12}$alkyl (C$_6$-C$_{12}$ aryl); R$_2$ is H; R$_4$ is H; and R$_5$ is H or C$_1$-C$_6$alkyl, wherein R$_2$ and R$_5$ are taken together from the nitrogen atoms to which they are bound to form a heterocycle or spiro-heterocycle; n is 0; and m is 0.

In an embodiment, Z is —S(O)$_2$OR$_6$, and H, C$_1$-C$_{12}$alkyl or C$_6$-C$_{12}$ aryl, wherein alkyl and aryl are optionally substituted with 1, 2, or 3 groups, each independently selected from halo, —OH, C$_1$-C$_6$alkyl, C$_1$-C$_6$-haloalkyl, —O-C$_1$-C$_6$alkyl, —NO$_2$, —N(H)(R$_{12}$), and —CN; R$_1$ is —CH$_2$CH$_2$NH$_2$; R$_2$ is H; n is 0; and m is 0.

In an embodiment, the compound of any of claims 35-43, wherein Z is —S(O)$_2$OR$_6$;

R$_6$ is C$_1$-C$_{12}$alkyl or C$_6$-C$_{12}$ aryl, wherein alkyl and aryl are optionally substituted with 1, 2, or 3 groups, each independently selected from halo, —OH, C$_1$-C$_6$-alkyl, C$_1$-C$_6$-haloalkyl, —O-C$_1$-C$_6$-alkyl, —NO$_2$, —N(H)(R$_{12}$), and —CN; R$_1$ is —CH$_2$CH$_2$NH$_2$; R$_3$ is (C$_6$-C$_{12}$ aryl); n is 0; and m is 0.

In an embodiment, R$_3$ is H or C$_6$-C$_{12}$ aryl;

In an embodiment, n is 0; and m is 0.

Certain embodiments of Formulas I, II, III, IV, V, and 8-((2-aminoethyl)amino)naphthalene-1-sulfonic acid are shown below in Table 1.

TABLE 1
| SHIP1 inhibitors | |
|---|---|
| 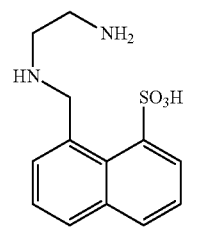 | 001 |
| 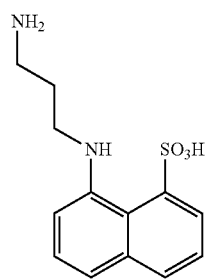 | 002 |
| 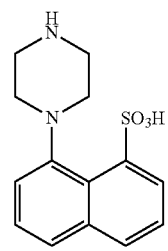 [SMILES: O=S(=O)(O)c1cccc2cccc(N3CCNCC3)c12] | 003 |
| 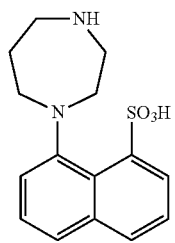 [SMILES: O=S(=O)(O)c1cccc2cccc(N3CCCNCC3)c12] | 004 |
| 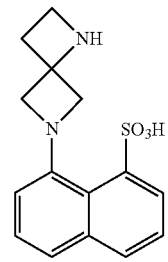 [SMILES: O=S(=O)(O)c1cccc2cccc(N3CC4(CCN4)C3)c12] | 005 |
| 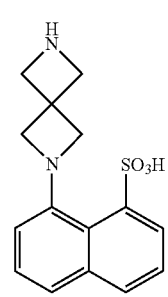 [SMILES: O=S(=O)(O)c1cccc2cccc(N3CC4(CNC4)C3)c12] | 006 |
TABLE 1-continued
| SHIP1 inhibitors | |
|---|---|
| 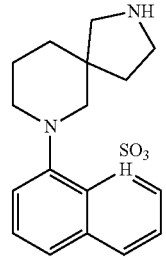 | 007 |
| 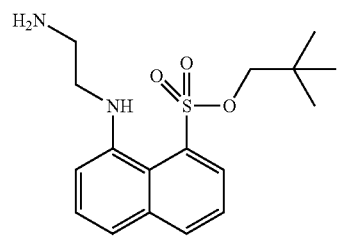 [SMILES: CC(C)(C)COS(=O)(=O)c1cccc2cccc(NCCN)c12] | 008 |
| 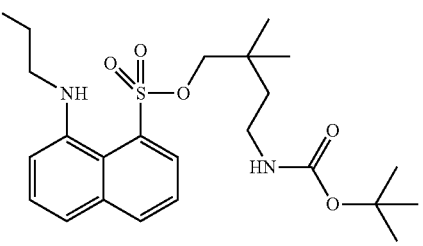 | 009 |
| 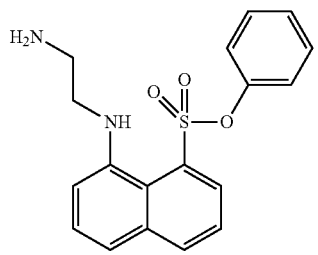 [SMILES: NCCNc1cccc2cccc(S(=O)(=O)Oc3ccccc3)c12] | 010 |
| 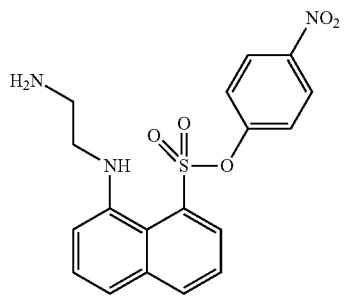 [SMILES: NCCNc1cccc2cccc(S(=O)(=O)Oc3ccc([N+](=O)[O-])cc3)c12] | 011 |
| 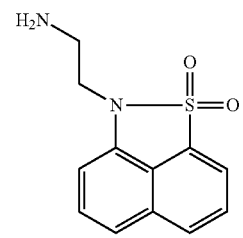 [SMILES: NCCN1c2cccc3cccc(c23)S1(=O)=O] | 012 |

TABLE 1-continued

SHIP1 inhibitors

| | |
|---|---|
| | 013 |

8-((2-aminoethyl)amino)naphthalene-1-sulfonic acid structure with NH₂, NH, and SO₃H groups on naphthalene In an embodiment, compounds of Formulas I, II, III, IV, V, and 8-((2-aminoethyl)amino)naphthalene-1-sulfonic acid are selected from:

| Compound ID | Compound Name |
|---|---|
| 001 | 8-(((2-aminoethyl)amino)methyl)naphthalene-1-sulfonic acid |
| 002 | 8-((3-aminopropyl)amino)naphthalene-1-sulfonic acid |
| 003 | 8-(piperazin-1-yl)naphthalene-1-sulfonic acid |
| 004 | 8-(1,4-diazepan-1-yl)naphthalene-1-sulfonic acid |
| 005 | 8-(1,6-diazaspiro[3.3]heptan-6-yl)naphthalene-1-sulfonic acid |
| 006 | 8-(2,6-diazaspiro[3.3]heptan-2-yl)naphthalene-1-sulfonic acid |
| 007 | 8-(2,7-diazaspiro[4.5]decan-7-yl)naphthalene-1-sulfonic acid |
| 008 | neopentyl 8-((2-aminoethyl)amino)naphthalene-1-sulfonate |
| 009 | 4-((tert-butoxycarbonyl)amino)-2,2-dimethylbutyl 8-((2-aminoethyl)amino)naphthalene-1-sulfonate |
| 010 | phenyl 8-((2-aminoethyl)amino)naphthalene-1-sulfonate |
| 011 | 4-nitrophenyl 8-((2-aminoethyl)amino)naphthalene-1-sulfonate |
| 012 | 2-(2-aminoethyl)-2H-naphtho[1,8-cd]isothiazole 1,1-dioxide |
| 013 | 8-((2-aminoethyl)amino)naphthalene-1-sulfonic acid | and pharmaceutically acceptable salts or solvates thereof.

The SHIP1 inhibitors may possess one or more stereocenters, and each stereocenter may exist independently in either the R or S configuration. In one embodiment, compounds described herein are present in optically active or racemic forms. It is to be understood that the compounds described herein encompass racemic, optically-active, regioisomeric and stereoisomeric forms, or combinations thereof that possess the therapeutically useful properties described herein.

Preparation of optically active forms is achieved in any suitable manner, including by way of non-limiting example, by resolution of the racemic form with recrystallization techniques, synthesis from optically-active starting materials, chiral synthesis, or chromatographic separation using a chiral stationary phase. In one embodiment, a mixture of one or more isomers is utilized as the SHIP1 inhibitor described herein. In another embodiment, compounds described herein contain one or more chiral centers. These compounds are prepared by any means, including stereoselective synthesis, enantioselective synthesis or separation of a mixture of enantiomers or diastereomers. Resolution of compounds and isomers thereof is achieved by any means including, by way of non-limiting example, chemical processes, enzymatic processes, fractional crystallization, distillation, and chromatography.

It is also to be understood that compounds that have the same molecular formula but differ in the nature or sequence of bonding of their atoms or the arrangement of their atoms in space are termed "isomers." Isomers that differ in the arrangement of their atoms in space are termed "stereoisomers," for example, diastereomers, enantiomers, and atropisomers.

Stereoisomers that are not mirror images of one another are termed "diastereomers" and those that are non-superimposable mirror images of each other are termed "enantiomers." When a compound has an asymmetric center, for example, it is bonded to four different groups, a pair of enantiomers is possible. An enantiomer can be characterized by the absolute configuration of its asymmetric center and is described by the R-and S-sequencing rules of Cahn and Prelog, or by the manner in which the molecule rotates the plane of polarized light and designated as dextrorotatory or levorotatory (i.e., as (+) or (-)-isomers respectively). A chiral compound can exist as either individual enantiomer or as a mixture thereof. A mixture containing equal proportions of the enantiomers is called a "racemic mixture."

Unless indicated otherwise, the description or naming of a particular compound in the specification and claims is intended to include both individual enantiomers and mixtures, racemic or otherwise, thereof. Within the present disclosure, any open valency appearing on a carbon, oxygen, or nitrogen atom in any structure described herein indicates the presence of a hydrogen atom. Where a chiral center exists in a structure, but no specific stereochemistry is shown for that center, both enantiomers, separately or as a mixture, are encompassed by that structure. The methods for the determination of stereochemistry and the separation of stereoisomers are well-known in the art.

In embodiments, the SHIP1 inhibitors may exist as tautomers. All tautomers are included within the scope of the compounds presented herein.

Compounds described herein also include isotopically-labeled compounds wherein one or more atoms is replaced by an atom having the same atomic number, but an atomic mass or mass number different from the atomic mass or mass number usually found in nature. Examples of isotopes suitable for inclusion in the compounds described herein include and are not limited to $^{2}H$, $^{3}H$, $^{11}C$, $^{13}C$, $^{14}C$, $^{36}Cl$, $^{18}F$, $^{123}I$, $^{125}I$, $^{13}N$, $^{15}N$, $^{15}O$, $^{17}O$, $^{18}O$, $^{32}P$, and $^{35}S$. In one embodiment, isotopically-labeled compounds are useful in drug or substrate tissue distribution studies. In another embodiment, substitution with heavier isotopes such as deuterium affords greater metabolic stability (for example, increased in vivo half-life or reduced dosage requirements).

In yet another embodiment, substitution with positron emitting isotopes, such as $^{11}C$, $^{18}F$, $^{15}O$ and $^{13}N$, is useful in Positron Emission Topography (PET) studies for examining substrate receptor occupancy. Isotopically-labeled compounds are prepared by any suitable method or by processes using an appropriate isotopically-labeled reagent in place of the non-labeled reagent otherwise employed.

In one embodiment, the compounds described herein are labeled by other means, including, but not limited to, the use of chromophores or fluorescent moieties, bioluminescent labels, or chemiluminescent labels.

The compounds described herein, and other related compounds having different substituents are synthesized using techniques and materials described herein and as described, for example, in Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), Larock's Comprehensive Organic Transformations (VCH Publishers Inc., 1989), March, Advanced Organic Chemistry $4^{th}$ Ed., (Wiley 1992); Carey and Sundberg, Advanced Organic Chemistry 4th Ed., Vols. A and B (Plenum 2000, 2001), and Green and Wuts, Protective Groups in Organic Synthesis 3rd Ed., (Wiley 1999) (all of which are incorporated by reference for such disclosure). General methods for the preparation of compound as described herein are modified by the use of appropriate reagents and conditions, for the introduction of the various moieties found in the formula as provided herein.

Compounds described herein are synthesized using any suitable procedures starting from compounds that are available from commercial sources, or are prepared using procedures described herein.

Use of SHIP1 Inhibitors to Treat Graft-Versus-Host Disease (GvHD)

SHIP1 inhibitors have therapeutic potential in treating Graft-versus-Host Disease (GvHD) (see Wang et al., Influence of SHIP on the NK repertoire and allogeneic bone marrow transplantation. Science. 2002; 295:2094-2097; Ghansah et al., Expansion of myeloid suppressor cells in SHIP-deficient mice represses allogeneic T cell responses. J Immunol. 2004; 173:7324-7330; Paraiso et al. Induced SHIP deficiency expands myeloid regulatory cells and abrogates graft-versus-host disease. J Immunol. 2007; 178:2893-2900). GvHD is an autoimmune reaction by the body to a transplanted organ or tissue, such as bone marrow used to treat cancers and genetic disorders. GvHD is the leading cause of treatment related mortality in bone marrow transplant recipients and is mediated by donor T cells that attack host tissue. SHIP1 expression by the host is necessary for efficient rejection of allogeneic bone marrow and cardiac grafts and the GvHD that compromises posttransplant survival (see Wahle et al., Inappropriate recruitment and activity by the Src Homology Region 2 Domain-Containing Phosphatase 1 (SHP1) is responsible for receptor dominance in the SHIP-deficient NK cell, J Immunol, (2007);179:8009-8015; Wang et al., Influence of SHIP on the NK repertoire and allogeneic bone marrow transplantation, Science, (2002); 295:2094-2097; Wahle et al., Cutting edge: dominance by an MHC-independent inhibitory receptor compromises NK killing of complex targets, J Immunol, (2006); 176:7165-7169; Collazo et al. SHIP limits immunoregulatory capacity in the T-cell compartment, Blood, (2009); 113:2934-2944). SHIP1 knockout mice show a 10- to 20-fold expansion of MDSC cells, thought to be a mediator of immune suppression, which protects them from GvHD during T cell replete allogeneic bone marrow transplantation. (Ghansah et al., Expansion of myeloid suppressor cells in SHIP-deficient mice represses allogeneic T cell responses, J Immunol, (2004); 173:7324-7330; Paraiso et al. Induced SHIP deficiency expands myeloid regulatory cells and abrogates graft-versus-host disease, J Immunol, (2007); 178: 2893-2900; Bronte et al. Apoptotic death of CD8+ T lymphocytes after immunization: induction of a suppressive population of Mac-1+/Gr-1+cells, J Immunol, (1998); 161: 5313-5320).

SHIP1 inhibition may also limit GvHD due to upregulation of T regulatory (Treg) cells, which limit harmful allogeneic T cell responses that cause GvHD. Treg cells can also promote engraftment of allogeneic bone marrow cells (Hoffmann et al. Donor-type CD4(+)CD25(+) regulatory T cells suppress lethal acute graft-versus-host disease after allogeneic bone marrow transplantation. J Exp Med. (2002); 196:389-399; Edinger et al. CD4+CD25+ regulatory T cells preserve graft-versus-tumor activity while inhibiting graft-versus-host disease after bone marrow transplantation. Nat Med. (2003); 9:1144-1150; Ermann et al. Only the CD62L+ subpopulation of CD4+ CD25+ regulatory T cells protects from lethal acute GVHD. Blood. (2005); 105:2220-2226; Taylor et al. L-Selectin(hi) but not the L-selectin(lo) CD4+ 25+ T-regulatory cells are potent inhibitors of GVHD and BM graft rejection. Blood. (2004); 104:3804-3812). Treg cells have been shown to reduce GvHD without reducing the beneficial effects of donor T cell-mediated graft-versus-tumor effects post-transplant. SHIP1 not only limits intrinsic signaling that leads to the development and formation of Treg cells in the periphery, but also limits the extrinsic effects of myeloid cells that promote Treg formation (Collazo et al. SHIP limits immunoregulatory capacity in the T-cell compartment. Blood. (2009); 113:2934-2944; Collazo et al. Lineage extrinsic and intrinsic control of immunoregulatory cell numbers by SHIP. Eur J Immunol. (2012); 42:1785-1795). Thus, inhibition of SHIP1 can increase the production of Treg cells.

Use of SHIP1 Inhibitors to Treat Anemia, Thrombocytopenia, Neutropenia

Provided herein is a method for treating anemia, thrombocytopenia, or neutropenia, including administering an effective amount of a SHIP1 inhibitor. Anemia, thrombocytopenia, and/or neutropenia may be caused by cancer chemotherapy treatment, by accidental radiation poisoning, or bone marrow disease (e.g. infection, leukemia, lymphoma, tumors, autoimmune disorders, etc.). All three types of blood disorder may be acquired, meaning induced by an outside factor (e.g. chemotherapy, radiation, infection, bone marrow disease), or may be congenital inherited genetic disorder (e.g. hereditary spherocytosis).

Anemia is a decrease in the total number of red blood cells (RBCs) or hemoglobin in the blood, resulting in symptoms such as tiredness, weakness, and even loss of consciousness. In some embodiments, compounds, salts, and solvates disclosed herein are used to treat subjects with an acquired anemia. Exemplary acquired anemias include pure red cell aplasia (PRCA), aplastic anemia, renal failure anemia, pernicious anemia, anemia of prematurity, iron deficiency anemia, vitamin deficiency anemia (e.g. from lack of folic acid or vitamin B12), chronic anemia, anemia associated with bone marrow disease (e.g. myeloproliferative disease, leukemia, lymphoma, metastatic carcinoma, myeloma, etc.), myelodysplastic syndrome, anemia of chronic inflammation, and acquired hemolytic anemia (e.g. from infection, autoimmune disease, chronic liver disease, hypersplenism, etc.). In some embodiments, compounds, salts, and solvates disclosed herein are used to treat subjects with anemia from a genetic disorder, such as hereditary spherocytosis, hereditary elliptocytosis, abetalipoproteinemia, enzyme deficiencies (e.g. pyruvate kinase, hexokinase, glucose-6-phosphate dyhydrogenase, or glutathione synthetase), hemoglobinopathies, or sickle cell anemia.

Thrombocytopenia is blood disorder in which the blood has abnormally low levels of thrombocytes (platelets). Decreased platelet production or increased platelet destruction may be caused by dehydration, vitamin deficiency (e.g. vitamin B12 or folic acid), leukemia, myelodysplastic syndrome, aplastic anemia, liver failure, sepsis from systemic infection (viral or bacterial), leptospirosis, medication-induced thrombocytopenia (e.g. from direct myelosuppression from valproic acid, methotrexate, carboplatin, interferon, isotretinoin, panobinostat, histamine blockers, or proton-pump blockers), or immune or autoimmune conditions (e.g.

idiopathic thrombocytopenic purpura, thrombotic thrombocytopenic purpura, hemolytic-uremic syndrome, disseminated intravascular coagulation, aroxysmal nocturnal hemoglobinuria, Antiphospholipid syndrome, systemic lupus erythematosus, post-transfusion purpura, neonatal alloimmune thrombocytopenia, hypersplenism, Dengue fever, Gaucher's disease, or Zika virus).

Neutropenia is a blood disorder in which the blood has abnormal levels of neutrophils. Chronic neutropenia may be caused by aplastic anemia, glycogen storage disease, vitamin deficiency, or a genetic disorder (e.g. congenital immunologic disorders, Cohen syndrome, Barth syndrome, Pearson syndrome, or Pudlak syndrome). Transient neutropenia may be caused by infections (e.g. typhoid, tuberculosis, cytomegalovirus), or induced by medication (e.g. propylthiouracil, levamisole, penicillamine, trimethoprim, clozapine, or valproate). In an embodiment, a subject receiving compounds, salts, and solvates described herein may have an acquired neutropenia.

Inhibition of SHIP1 in healthy cells leads to an increase in PI(3,4,5)P3, resulting in an increase in the amount of cell division and/or survival specific to blood cells and other cells of the hematopoietic lineage. Studies with a selective SHIP1 inhibitor recently showed that RBC counts were preserved and neutrophil and platelet counts rebounded faster in myeloablated mice treated with the SHIP1 inhibitor as compared to vehicle controls (Brooks et al. SHIP1 Inhibition Increases Immunoregulatory Capacity and Triggers Apoptosis of Hematopoietic Cancer Cells. J Immunol. (2010); 184:3582-3589). SHIP inhibition in the setting of myeloablation promotes faster rebound of lymphocytes and white blood cells. The enhanced recovery mediated by SHIP1 inhibition is pan-hematolymphoid suggesting there may be effects of SHIP inhibition directly on the hematopoietic stem cell (HSC) compartment and/or on the niche cells that sustain HSC. SHIP1 as well as a stem cell specific isoform of SHIP1 (s-SHIP) are expressed by HSC (Tu et al. Embryonic and hematopoietic stem cells express a novel SH2-containing inositol 5'-phosphatase isoform that partners with the Grb2 adapter protein. Blood. (2001); 98:2028-2038). In addition, mesenchymal stem cells and osteoblasts that support HSC also express SHIP1 (Iyer et al. Role of SHIP1 in bone biology. Ann N Y Acad Sci. (2013); 1280: 11-14; Hazen et al. SHIP is required for a functional hematopoietic stem cell niche. Blood. (2009); 113:2924-2933).

Use of SHIP1 Inhibitors to Treat Infections and Cancer

Provided herein is a method for inhibiting a SH2-containing inositol 5'-phosphatase (SHIP) in a subject, including administering a safe and effective amount of a SHIP1 inhibitor, wherein the subject has an illness or condition for which NK cells and/or T cells provide a host defense. The illness or condition of the subject may be cancer or an infection, such as a viral or bacterial infection.

Cancers are classified by the cell type from which they are derived. Hematologic or hematopoietic cancers are derived from bone marrow cells and include lymphomas derived from abnormal B or T cells that localize in lymph nodes, and leukemias derived from abnormal B and T cells in the bone marrow and blood. Carcinomas are derived from epithelial cells, which includes cancers of the breast, prostate, lung, pancreas and colon. Sarcomas are derived from mesenchymal cells of connective tissue such as bone, cartilage, fat, and nerve cells. Germ cell cancers are derived from pluripotent cells often from the testicle or ovary. Blastomas are derived from immature precursor cells or embryonic tissue that is not completely differentiated.

In an embodiment, a subject may have a non-hematologic cancer, such as a carcinoma, a sarcoma, a germ cell cancer or a blastoma. The cancer may be a carcinoma.

In an embodiment, the illness or condition for which NK cells and/or T cells provide a host defense is a hematologic cancer. The hematologic cancer is selected from the group consisting of leukemia, acute lymphoblastic leukemia (ALL), acute myelogenous leukemia (AML), chronic lymphocytic leukemia (CLL), small lymphocytic lymphoma (SLL), chronic myelogenous leukemia (CML), acute monocytic leukemia (AMoL), Hodgkin's lymphoma, non-Hodgkin's lymphoma, and multiple myeloma.

As used herein, the term "leukemia" refers to a malignant progressive disease in which the bone marrow and other blood-forming organs produce increased numbers of immature or abnormal leukocytes that suppress the production of normal blood cells, leading to anemia and other symptoms. Whether leukemia is acute or chronic depends on whether most of the abnormal cells are immature (and are more like stem cells) or mature (more like normal white blood cells). In chronic leukemia, the cells can mature partly but not completely. Types of leukemia include, but are not limited to, acute lymphoblastic leukemia (ALL), acute myeloid leukemia (AML), chronic lymphocytic leukemia (CLL), small lymphocytic lymphoma (SLL), chronic myeloid leukemia (CML), and acute monocytic leukemia (AMoL).

Acute lymphocytic leukemia (ALL), also called acute lymphoblastic leukemia, is a myeloid cancer of bone marrow that causes growth of cancerous, immature lymphocytes. Acute myeloid leukemia (AML) is a myeloid cancer that produces abnormal myeloblasts, red blood cells, or platelets. AML starts in the bone marrow, but in most cases, it quickly moves into the blood. It can sometimes spread to other parts of the body including the lymph nodes, liver, spleen, central nervous system (brain and spinal cord), and testicles. Acute monocytic leukemia (AMoL) is a distinct subtype of AML in which monocytes or monoblasts are the predominant cancerous lineage. Chronic lymphocytic leukemia (CLL) refers to a typically slow-growing cancer which begins in B-cell lymphocytes of the bone marrow and extends into the blood. CLL is considered a stage of small lymphocytic lymphoma (SLL) in which B-cells accumulate in the lymph nodes. Chronic myeloid leukemia (CML), also known as chronic myelogenous leukemia, is a type of cancer that starts in certain blood-forming cells of the bone marrow. In CML, mutations to the gene BCR-ABL occur in immature myeloid cells, leading to proliferation of mature granulocytes and their precursors. CML is an initially slow-growing leukemia, but it can eventually become fast-growing acute leukemia that is difficult to treat. Multiple myeloma is a cancer formed by malignant B-cells after leaving the lymph nodes Non-Hodgkin's lymphoma refers to a diverse class of cancers in both B cells and T cells that are classified by the type of lymphocyte, its morphology, chromosomal features of the cancerous lymphocyte, and cell surface markers. Non-Hodgkin B cell lymphomas include diffuse large B-cell lymphoma (DLBCL), follicular lymphoma, hronic lymphocytic leukemia (CLL /small lymphocytic lymphoma (SLL), mantle cell lymphoma (MCL), marginal zone lymphomas, Burkitt lymphoma, lymphoplasmacytic lymphoma (Waldenstrom macroglobulinemia), and hairy cell leukemia.

Hodgkin's lymphoma is primarily a B cell lymphoma accumulating in the lymph nodes and causing swelling. Classical Hodgkin's lymphoma is classified into four pathologic subtypes according to B cell morphology (Reed-Sternberg cells) and the cell infiltrate in the affected lymph node (including nodular sclerosing HL, mixed-celularity subtype, lymphocyte rich, and lymphocyte depleted.

Administration/Dosage/Formulations

In another aspect, provided herein is a pharmaceutical composition comprising at least one SHIP1 inhibitor, or a pharmaceutically acceptable salt or solvate thereof.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

In particular, the selected dosage level will depend upon a variety of factors including the activity of the particular compound employed, the time of administration, the rate of excretion of the compound, the duration of the treatment, other drugs, compounds or materials used in combination with the compound, the age, sex, weight, condition, general health and prior medical history of the patient being treated, and like factors well, known in the medical arts.

A medical doctor, e.g., physician or veterinarian, having ordinary skill in the art may readily determine and prescribe the effective amount of the pharmaceutical composition required. For example, the physician or veterinarian could begin administration of the pharmaceutical composition to dose the SHIP1 inhibitor at levels lower than that required in order to achieve the desired therapeutic effect and gradually increase the dosage until the desired effect is achieved.

In some embodiments, the compounds and salts disclosed herein may be administered as a solvate in a continuous manner. For example, a single dose may be administered to a subject as a solvate (e.g. intravenously or a delayed release capsule) for an administration period of 1, 2, 3, 4, 5, 6, 7, 8, 9, 10, 15, 30, 45, or 60 minutes. In some embodiments, a single dose may be administered to a subject as a solvate for an administration period of 1-5, 5-10, 10-15, 15-30, 30-45, or 45-60 minutes. In some embodiments, a single dose may be administered to a subject as a solvate for an administration period of 1-60 minutes. In some embodiments a single dose may be administered to a subject for an administration period of 1, 2, 3, 4, 5, 6, 7, 8, 9, 10, 11, 12, 24, 36, 48, 60, or 72 hours. In some embodiments a single dose may be administered to a subject for an administration period of 1-6, 6-12, 12-24, 24-48, 48-60, 60-72 hours. In some embodiments a single dose may be administered to a subject for an administration period of 1-72 hours.

In some embodiments, multiple doses of the compounds and salts described herein may be administered to a subject in a pulsatile or intermittent manner. As used herein the term "pulsatile dose regimen" or "intermittent dose regimen" refers to a dose administration regimen which includes at least two dosing cycles. Each subsequent dosing cycle is separated by a rest period from the preceding dosing cycle.

As used herein in reference to a pulsatile dose regimen, the term "dosing cycle" refers to a single cycle of dose administration that can be repeated, with each dosing cycle consisting of one or more dose administrations of the compound, salt or solvate at a set dosage for a set administration period at set time intervals during a defined period of time (e.g., 50 mg/kg of compound administered for 1 hour every 8 hours over a period of two days). The dosage and administration period of each dose administration of a dosing cycle, and of different dosing cycles in a pulsatile dose regimen, can be the same or can differ. The time intervals between the dose administrations of a dosing cycle can be the same or can differ (e.g., the first two of three dose administrations can be 8 hours apart and the third dose administration can be 24 hours later). The duration of each dosing cycle in a pulsatile dose regimen can be the same or can differ (e.g., the first dosing cycle of three can have a duration of three days, the second dosing cycle can have a duration of two days and the third dosing cycle can have a duration of one day). Example dosages that can be delivered in each dose administration, dosing cycle and pulsatile dose regimen are described below. In some embodiments, the administration period of any dose administration of a dosing cycle has a duration of about 1/10, 1/6, 1/4, 1/2, 1, 2, 3, 4, 5, 6, 7, 8, 9, 10, 11, 12, 15, 18, 21, 24, 36 or 48 hours, or any time period in between. In some embodiments, the time interval between two dose administrations of a dosing cycle is about 1, 2, 3, 4, 5, 6, 7, 8, 9, 10, 11, 12, 15, 18, 21, 24, 36, or 48 hours, or any time period in between. In various embodiments, the time interval can be defined as an interval of time between the start time of successive dose administrations or between the end of one dose administration and the start of the next. In some embodiments, the time intervals between dose administrations of a dosing cycle may be expressed in terms of the number of dose administrations per day, and include administration of a dose 2, 3, 4, 5, 6, 7, 8, 9, 10, 11, 12, 18 or 24 times a day. In some embodiments, the time intervals for dose administrations of a dosing cycle may be expressed as a specified number of administrations at specified times of the day, such as, for example, four dose administrations per day given at 8:00 am, 12:00 pm, 4:00 pm, and 8:00 pm, or three dose administrations two hours after each of three meals. In some embodiments, a dosing cycle includes time intervals between dose administrations of 1-3 hours, 3-6 hours, 6-9 hours, 9-12 hours, 12-15 hours, 15-18 hours, 18-21 hours, or 21-24 hours. In some embodiments, the defined period of time during which the dose administrations of a dosing cycle are made (i.e., the length of a dosing cycle) is 1, 2, 3, 4, 5, 6, 7, 8, 9, 10, 11, 12, 15, 18, 21, 24, or 28 days. In some embodiments, the dosage of the dose administrations during a dosing cycle may vary due to the different lengths of the administration periods. For example, a first administration period of a solvate may be 3 hours, while a second administration period of the solvate may be 1 hour, resulting in a lower dosage of the solvate being administered. In some embodiments, each of the one or more dose administrations during a dosing cycle may deliver the same or a different dosage of the compound, salt or solvate, or use the same or a different concentration.

As used herein when referring to a pulsatile dose regimen, the term "rest period" refers to a period of time during which no doses of the compound, salt, or solvate thereof are administered. During a pulsatile dose regimen, each succeeding dosing cycle is separated from the immediately preceding dosing cycle by a rest period. For example, if the pulsatile dose regimen consists of three dosing cycles, there is a rest period between the first dosing cycle and second dosing cycle and between the second dosing cycle and the third dosing cycle. In some embodiments, the rest period is 1, 2, 3, 4, 5, 6, 7, 8, 9, 10, 11, 12, 15, 18, 21, 24, or 28 days, or 5, 6, 7, 8, 9, 10, 11 or 12 weeks. In some embodiments, one or more of the rest periods in a pulsatile dose regime differ in their length of time. For example, a first rest period of a pulsatile dose regimen may be three days and subsequent rest periods may be 5 days.

In particular embodiments, it is especially advantageous to formulate the compound in dosage unit form for ease of administration and uniformity of dosage. "Dosage unit form" as used herein refers to physically discrete units suited as unitary dosages for the patients to be treated; each unit containing a predetermined quantity of the SHIP1 inhibitor calculated to produce the desired therapeutic effect in association with the required pharmaceutical vehicle. The dosage unit forms of the invention are dictated by and directly dependent on (a) the unique characteristics of the SHIP1 inhibitor and the particular therapeutic effect to be achieved, and (b) the limitations inherent in the art of compounding/formulating such a SHIP1 inhibitor for the inhibition of SHIP in a patient.

In one embodiment, the compounds of the invention are formulated using one or more pharmaceutically acceptable excipients or carriers. In one embodiment, the pharmaceutical compositions of the invention comprise a therapeutically effective amount of a SHIP1 inhibitor and a pharmaceutically acceptable carrier.

In some embodiments, the dose of a SHIP1 inhibitor is from about 0.05 mg/kg to about 150 mg/kg and particularly in a dosing range of from about 0.1 mg/kg to about 100 mg/kg. More particularly, the dosing range can be from 0.08 mg/kg to 140 mg/kg, from 0.1 mg/kg to 130 mg/kg, from 0.1 mg/kg to 120 mg/kg, from 0.1 mg/kg to 110 mg/kg, from 0.1 mg/kg to 110 mg/kg, from 0.5 mg/kg to 100 mg/kg, from 1 mg/kg to 100 mg/kg, from 10 mg/kg to 80 mg/kg, from 20 mg/kg to 70 mg/kg, from 20 mg/kg to 60 mg/kg, from 20 mg/kg to 50 mg/kg, from 20 mg/kg to 40 mg/kg, and from 20 mg/kg to 30 mg/kg.

Different dosage regimens may be used to inhibit SHIP1. In one embodiment, the compounds of the invention are administered at a dose from 0.05 mg/kg to 150 mg/kg or more particularly at a dose from 0.1 mg/kg to 100 mg/kg once a day, every other day, three times a week, twice a week, once a week, etc. In another embodiment, the compounds of the invention are administered at a dose from 0.08 mg/kg to 140 mg/kg, from 0.1 mg/kg to 130 mg/kg, from 0.1 mg/kg to 120 mg/kg, from 0.1 mg/kg to 110 mg/kg, from 0.1 mg/kg to 110 mg/kg, from 0.5 mg/kg to 100 mg/kg, from 1 mg/kg to 100 mg/kg, from 10 mg/kg to 80 mg/kg, from 20 mg/kg to 70 mg/kg, from 20 mg/kg to 60 mg/kg, from 20 mg/kg to 50 mg/kg, from 20 mg/kg to 40 mg/kg, and from 20 mg/kg to 30 mg/kg once a day, every other day, three times a week, twice a week, once a week, etc. In one embodiment, the present invention is directed to a packaged pharmaceutical composition comprising a container holding a therapeutically effective amount of a SHIP1 inhibitor, alone or in combination with a second pharmaceutical agent; and instructions for using the compound to inhibit SHIP in a patient.

Routes of administration of any of the compositions of the invention include oral, nasal, rectal, intravaginal, parenteral, buccal, sublingual or topical. The compounds for use in the invention may be formulated for administration by any suitable route, such as for oral or parenteral, for example, transdermal, transmucosal (e.g., sublingual, lingual, (trans) buccal, (trans)urethral, vaginal (e.g., trans- and perivaginally), (intra)nasal and (trans)rectal), intravesical, intrapulmonary, intraduodenal, intragastrical, intrathecal, subcutaneous, intramuscular, intradermal, intra-arterial, intravenous, intrabronchial, inhalation, and topical administration.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

For oral application, particularly suitable are tablets, dragees, liquids, drops, suppositories, or capsules, caplets and gelcaps. The compositions intended for oral use may be prepared according to any method known in the art and such compositions may contain one or more agents selected from the group consisting of inert, non-toxic pharmaceutically excipients that are suitable for the manufacture of tablets. Such excipients include, for example an inert diluent such as lactose; granulating and disintegrating agents such as cornstarch; binding agents such as starch; and lubricating agents such as magnesium stearate. The tablets may be uncoated or they may be coated by known techniques for elegance or to delay the release of the active ingredients. Formulations for oral use may also be presented as hard gelatin capsules wherein the active ingredient is mixed with an inert diluent.

For parenteral administration, the SHIP1 inhibitors may be formulated for injection or infusion, for example, intravenous, intramuscular or subcutaneous injection or infusion, or for administration in a bolus dose or continuous infusion. Suspensions, solutions or emulsions in an oily or aqueous vehicle, optionally containing other formulatory agents such as suspending, stabilizing or dispersing agents may be used.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The following examples further illustrate aspects of the present invention. However, they are in no way a limitation of the teachings or disclosure of the present invention as set forth herein.

EXAMPLES

Exemplary compounds useful in methods of the invention will now be described by reference to the illustrative synthetic schemes for their general preparation below and the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Unless otherwise specified, the variables are as defined above in reference to Formula (I). Reactions may be performed between the melting point and the reflux temperature of the solvent, and preferably between 0° C. and the reflux temperature of the solvent. Reactions may be heated employing conventional heating or microwave heating. Reactions may also be conducted in sealed pressure vessels above the normal reflux temperature of the solvent.

Abbreviations and acronyms used herein include the following:

TABLE 2

| Term | Acronym |
|---|---|
| Acetonitrile | ACN or MeCN |
| Aqueous | aq |
| Atmosphere | atm |
| tert-Butylcarbamoyl | Boc |
| Boron-dipyrromethene | BODIPY |
| Benzyl | Bn |
| Broad | br |
| Capside assembly | CA |
| Carboxybenzyl | CBz |
| Diatomaceous Earth | CELITE |
| 1,1'-Carbonyldiimidazole | CDI |
| Doublet of doublets | dd |
| Diethylaminosulfur trifluoride | DAST |
| Di-tert-butyl azodicarboxylate | DBAD |
| 1,8-Diazabicyclo[5.4.0]undec-7-ene | DBU |
| Dichloroethane | DCE |
| Dichloromethane | DCM |
| Bis(2-methoxyethyl)aminosulfur trifluoride | DEOXO-FLUOR |
| Diethyl azodicarboxylate | DEAD |
| Diisopropyl azodicarboxylate | DIAD |
| Diisopropylethylamine | DIPEA, DIEA, or Hunig's base |
| 4-Dimethylaminopyridine | DMAP |
| 1,2-Dimethoxyethane | DME |
| N,N-Dimethylformamide | DMF |
| Dimethyl sulfide | DMS |
| Dimethylsulfoxide | DMSO |
| Deoxyribonucleic Acid | DNA |
| 1-Ethyl-3-(3-dimethylaminopropyl)carbodiimide | EDCI, EDAC, or EDC |
| Diethyl ether | Ether, Et$_2$O |
| Ethyl Acetate | EtOAc, or EA |
| Ethanol | EtOH |
| Electrospray ionization | ESI |
| Normal-phase silica gel chromatography | FCC |
| Grams | g |
| Hours | h or hr |
| (1-[Bis(dimethylamino)methylene]-1H-1,2,3-triazolo[4,5-b]pyridinium 3-oxid hexafluorophosphate) | HATU |
| Acetic acid | HOAc |
| 1-Hydroxy-7-azabenzotriazole | HOAt |
| Hydroxybenzotriazole | HOBt |
| High-pressure liquid chromatography | HPLC |
| Hertz | Hz |
| Isopropyl alcohol | iPrOH, IPA |
| Potassium tert-butoxide | KOtBu |
| Lithium aluminum hydride | LAH |
| Liquid chromatography and mass spectrometry | LCMS |
| Lithium diisopropylamide | LDA |
| Lithium bis(trimethylsilyl)amide | LHMDS |
| Molar | M |
| multiplet | m |
| Mass to charge ratio | m/z |
| meta-Chloroperoxybenzoic acid | mCPBA |
| Methyl Iodide | MeI |
| Methanol | MeOH |
| Milligrams | mg |
| Megahertz | MHz |
| Minute | min |
| Milliliter | mL |
| Microliter | μL |
| Millimole | mmol |
| Micromole | μmol |
| Mass spectrometry | MS |
| Mesityl chloride | MsCl |
| Normal | N |
| Sodium acetate | NaOAc |

TABLE 2-continued

| Term | Acronym |
|---|---|
| Sodium tert-butoxide | NaOt-Bu |
| N-Methylmorpholine N-oxide | NMO |
| Nuclear magnetic resonance | NMR |
| CF$_3$SO$_3$— or triflate | OTf |
| Polymerase chain reaction | PCR |
| Petroleum ether | PE |
| Palladium (II) acetate | Pd(OAc)$_2$ |
| Palladium(II)bis(triphenylphosphine) dichloride | Pd(PPh$_3$)$_2$Cl$_2$ |
| Tetrakis(triphenylphosphine)palladium(0) | Pd(PPh$_3$)$_4$ |
| [1,1'-Bis(di-tert-butylphosphino)ferrocene]dichloropalladium(II) | PdCl$_2$(dtbpf) or Pd(dtbpf)$_2$Cl$_2$ |
| [1,1'-Bis(diphenylphosphino)ferrocene]dichloro-palladium(II) | PdCl$_2$(dppf) or Pd(dppf)$_2$Cl$_2$ |
| 9-(2-Phosphonyl-methoxypropyly)adenine | PMPA |
| Parts per million | ppm |
| Precipitate | ppt |
| Polytetrafluoroethylene | PTFE |
| Pyridine | Py |
| Benzotriazol-1-yl-oxytripyrrolidinophosphonium hexafluorophosphate | PyBOP |
| Retention time | R$_t$ |
| Ribonucleic Acid | RNA |
| Room temperature | rt |
| singlet | s |
| Saturated | sat |
| 1-Chloromethyl-4-fluoro-1,4-diazoniabicyclo[2.2.2]octane bis(tetrafluoroborate) | SELECTFLUOR |
| [2-(Trimethylsilyl)ethoxy]methyl acetal | SEM |
| Supercritical Fluid Chromatography | SFC |
| Temperature | T |
| triplet | t |
| Propylphosphonic anhydride | T$_3$P |
| Tert-Butyl alcohol | tBuOH, t-BuOH |
| Tetra-n-butylammonium fluoride | TBAF |
| Tetra-n-butylammonium iodide | TBAI |
| Tert-butyldiphenylsilyl chloride | TBDPSCl |
| Triethylamine | TEA |
| Trifluoroacetic acid | TFA |
| Tetrahydrofuran | THF |
| Thin layer chromatography | TLC |
| Toll-like receptor | TLR |
| Tumor necrosis factor | TNF |
| Volume in milliliters of solvent per gram of substrate | V, or volumes |
| (Diethylamino)difluorosulfonium tetrafluoroborate | XTALFLUOR |

Example 2

Identification of Novel Selective SHIP1 Inhibitor

Figure 1B:
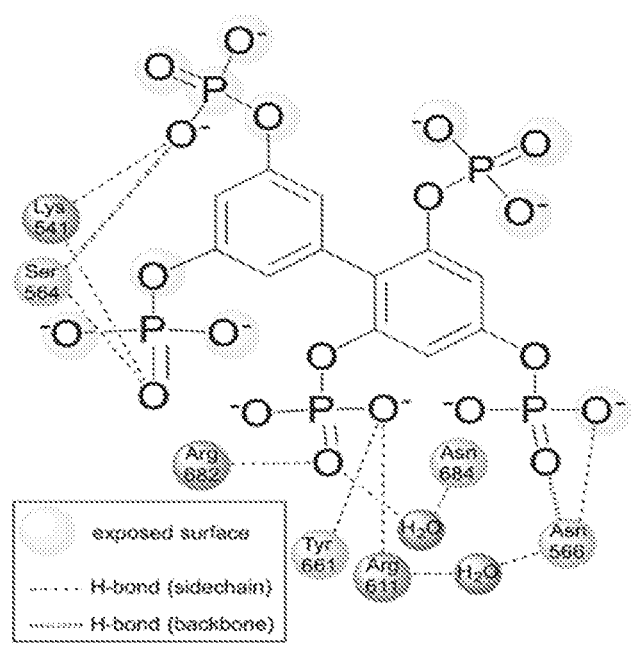
Figure 1C:
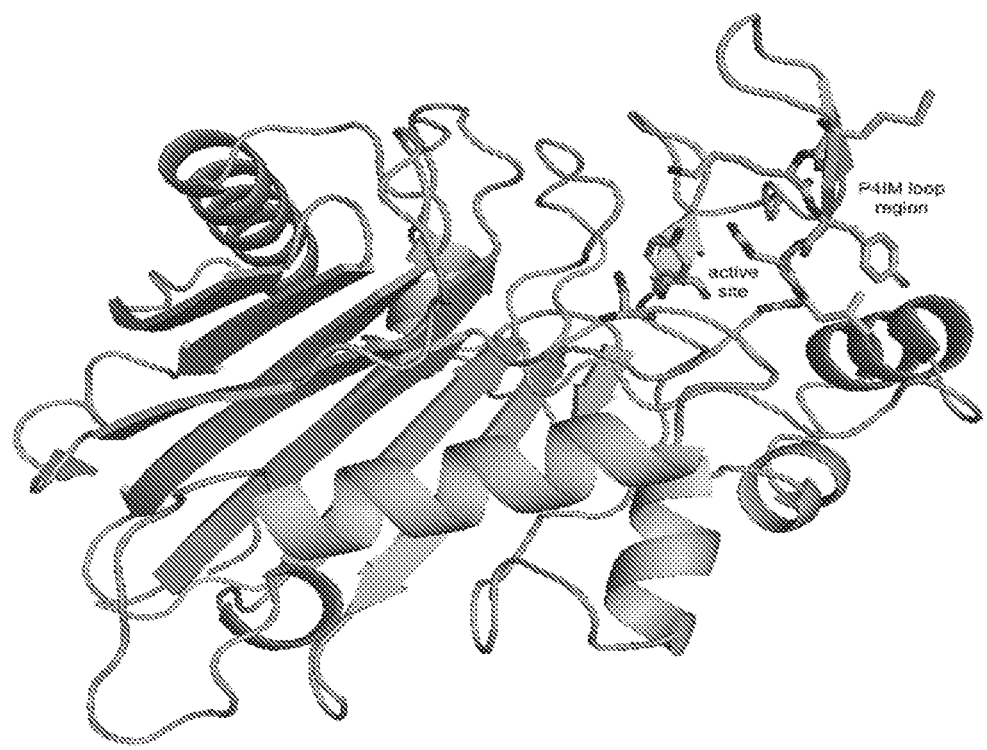

To identify and facilitate the development of improved selective inhibitors of SHIP, a rational design approach utilizing in silico docking was initiated using the available x-ray structure of a section of SHIP2 (the paralog of SHIP1) with a bound inhibitor (BiPh(2,3',4,5',6) P5) in the active site (FIGS. 1A and 1B). The SHIP2 structure was modified to have the same sequence as SHIP1, generating a model of the SHIP1 active site (FIG. 1C). The model of the SHIP1 active site also allowed virtual screening to identify selective SHIP1 inhibitors. A library of 200 compounds that were predicted to bind to the active site of SHIP1 was provided based on the virtual screen with the Zinc library of drug like compounds (Irwin, J. J. and B. K. Shoichet, ZINC—A Free Database of Commercially Available Compounds for Virtual Screening. J. Chem. Inf. Comput. Sci. (2005); 45: 177-182; Irwin, J. J.; Sterling et al., ZINC: A Free Tool to Discover Chemistry for Biology. J. Chem. Inf. Model. (2012); 52: 1757-1768 (~3.7 million compounds) and DOCK Blaster (Irwin, J. J. et al., Automated Docking Screens: A Feasibility Study. J. Med. Chem. (2009); 52: 5712-5720.

Figure 2A:
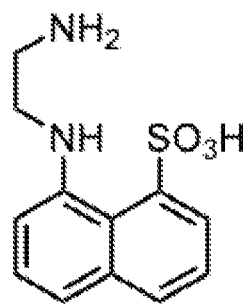
FIGS. 2A-2C show the results of a SHIP1 malachite phosphatase assay. The structure of K223, identified from a virtual screen is shown in FIG. 2A. K223 showed potent and selective inhibition of SHIP1 at 1 nm and 500 μM in the Malachite Green phosphatase assay (FIG. 2B).
Figure 2B:
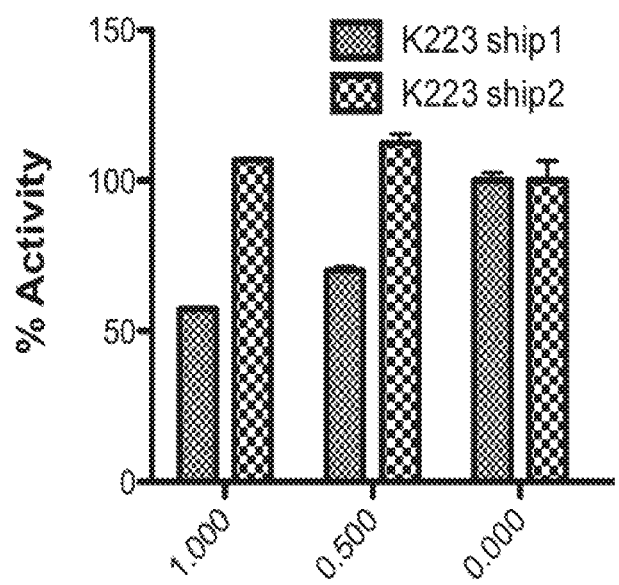
Figure 2C:
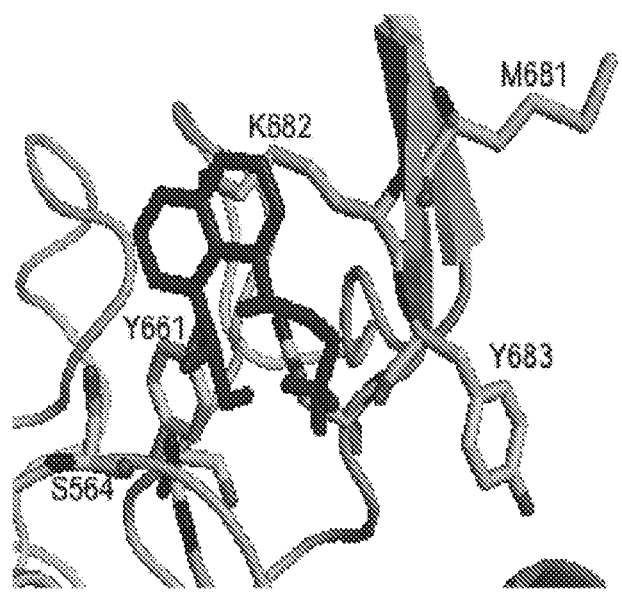

One of these structures from the virtual screening, K223 (FIG. 2A), displayed potent and selective inhibition of SHIP1 in the Malachite Green phosphatase assay (Brooks, R. et al., SHIP1 inhibition increases immunoregulatory capacity and triggers apoptosis of hematopoietic cancer cells. J. Immunol. (2010); 184: 3582-3589), attesting to the validity of utilizing docking to find SHIP inhibitors. K223 is an analog of EDANS, with the corresponding sulfonyl chloride of K223 being used as a donor for developing FRET-based nucleic acid probes and protease substrates. The docking pose of K223 with the model of the SHIP1 active site predicted that the sulfonic acid acts as a phosphate mimic, binding in the active site where the 5'-phosphate of PIP3 binds (FIG. 2B). The origin of the SHIP1 selectivity for K223 was not clear, however the nonpolar naphthalene core rests near K682 in the model of SHIP1, and this residue is a more polar arginine in SHIP2. This difference may have resulted in the observed SHIP1 selectivity.

Example 3

Figure 3A:
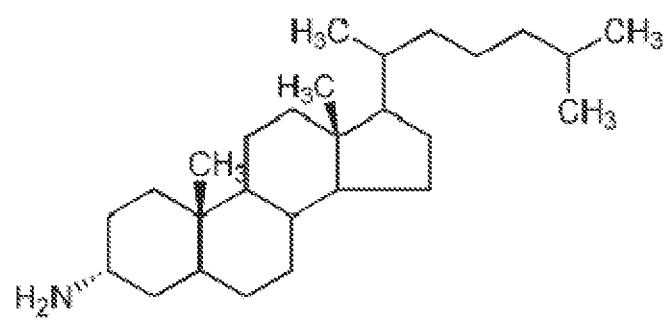
FIG. 3A shows the chemical structure of 3-α-aminocholestane (3AC).
Figure 3B:
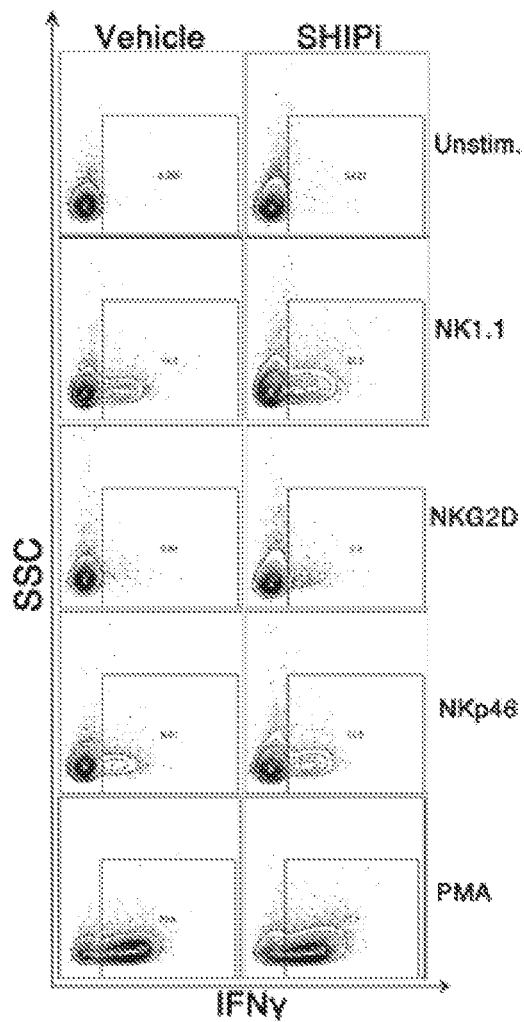
FIGS. 3B-3E show activation of NK cells and T cells following exposure to the SHIP1 inhibitor 3AC in vivo. NK cells from two-day 3AC- or vehicle-treated mice were stimulated by incubation on uncoated plates, on plates coated with anti-NK1.1, anti-NKp46, or anti-NKG2D antibody, or on uncoated plates but in the presence of PMA and ionomycin. Representative flow plots (FIG. 3B) and box and whisker plots (FIG. 3C) show the frequency of NK cell production of IFNγ determined by intracellular flow cytometry.
Figure 3C:
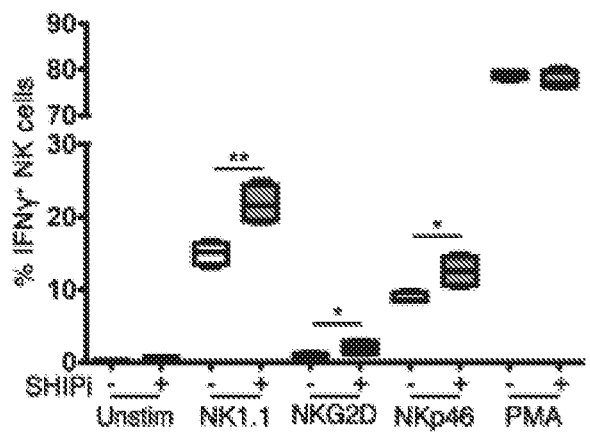

Short-Term Inhibition of SHIP1 in Vivo Promotes Increased Responsiveness of T Cells and NK Cells SHIP1 is recruited directly to the T cell receptor (TcR), as well as to the scaffolding protein Dok1 that limits T cell activation by the TcR (Reginald, K., Revisiting the timing of action of the PAG adaptor using quantitative proteomics analysis of primary T cells. J Immunol. (2015); 195: 5472-5481; Waterman, P. M. et al., The inositol 5phosphatase SHIP-1 and adaptors Dok-1 and 2 play central roles in CD4-mediated inhibitory signaling. Immunol Lett. (2012); 143: 122-130; Freeburn, R. W. et al., Evidence that SHIP-1 contributes to phosphatidylinositol 3,4,5-trisphosphate metabolism in T lymphocytes and can regulate novel phosphoinositide 3-kinase effectors. J Immunol. (2002); 169: 5441-5450; Dong, S. et al., T cell receptor for antigen induces linker for activation of T cell-dependent activation of a negative signaling complex involving Dok-2, SHIP-1 and Grb-2. J Exp Med. (2006); 203: 2509-2518; Tarasenko, T. et al., T cell-specific deletion of the inositol phosphatase SHIP reveals its role in regulating Th1/Th2 and cytotoxic responses. Proc Natl Acad Sci. USA. (2007); 104: 11382-11387. SHIP1 also opposes activation of the PI3K/Akt/mTOR signaling pathway in NK cells (Gumbleton, M. et al., SHIP1 intrinsically regulates NK cell signaling and education, resulting in tolerance of an MHC class I-mismatched bone marrow graft in mice. J Immunol, (2015); Wang, J. W. et al., Influence of SHIP on the NK repertoire and allogeneic bone marrow transplantation. Science. (2002); 295: 2094-2097). Accordingly, mice with extended duration of SHIP1 deficiency either from genetic ablation or from long-term treatment with SHIP1 inhibitors have increased activation of the PI3K signaling pathway. Interestingly however, NK cells from these mice had decreased capacity to perform effector functions (Gumbleton, M. et al., SHIP1 intrinsically regulates NK cell signaling and education, resulting in tolerance of an MHC class I-mismatched bone marrow graft in mice. J Immunol, (2015); Fernandes, S. et al., SHIPi enhances autologous and allogeneic hematopoietic stem cell transplantation. E Bio Medicine. (2015)). SHIP1 deficiency might initially result in increased PI3K signaling with resultant hyper-responsiveness, but continuous PI3K activation for an extended duration induces the hyporesponsive phenotype described previously. The small-molecule SHIP1 selective inhibitor 3-a-aminocholestane (3AC; see FIG. 3A) was used to inducibly ablate SHIP1 signaling. Specifically, hosts were treated for two consecutive days with either 3AC or vehicle control and then used in intracellular flow cytometry to measure NK cell IFN$\gamma$ production following cross-linking of three major NK cell activating receptors. NK cells from 3AC-treated hosts had significantly increased IFN$\gamma$ production following stimulation of each activating receptor relative to NK cells from vehicle controls (FIGS. 3B-3C). Consistent with SHIP1's proximal role in limiting receptor signaling, NK cells stimulated with PMA and ionomycin showed no difference between 3AC and vehicle controls. This indicated that SHIP1 was indeed playing a role in limiting NK cell receptor responsiveness and that short-term inhibition of SHIP1 function resulted in NK cell hyperresponsiveness that is not sufficient to disarm the NK cell compartment.

Figure 3D:
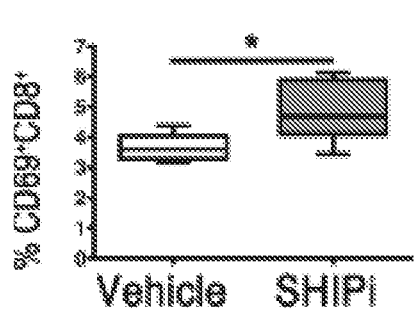
Figure 3E:
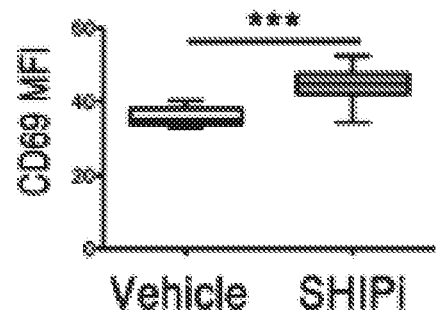
Figure 3F:
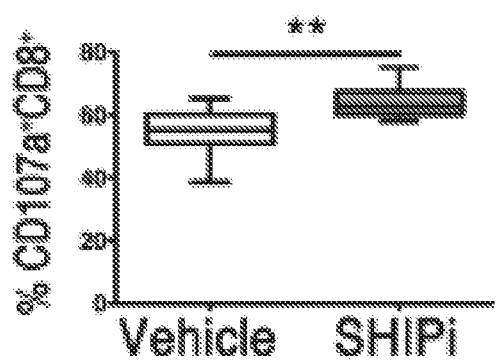
FIG. 3F shows a box and whisker plot of CD107a+/CD8+ T cells from two-day 3AC- or vehicle-treated mice, stimulated by overnight incubation on plates coated with anti-CD3 and anti-CD28 antibodies. Anti-CD107a (LAMP-1) PE antibody was added for the final 5 hours of incubation. Degranulation of CD8+ T cells was determined by analysis of CD107a expression by flow cytometry. NK cells are defined as NK1.1+CD3ε− and CD8+ T cells as NK1.1-CD3ε+CD8+CD4−. Graphs are representative of at least two independent experiments with at least four 3AC- and vehicle-treated mice per group (FIGS. 3B-3C) or pooled data from two independent experiments is shown (FIGS. 3D-3F).

To determine if SHIP inhibitors are also capable of activating the other major type of cytotoxic lymphocyte the responsiveness of CD8 T cells following the same, short-term, 3AC treatment was examined. As above, T cells from 3AC-treated mice also exhibited increased responsiveness compared to vehicle treated controls (FIGS. 3D and 3E). 3AC treatment significantly increased not only the percentage of activated CD8 T cells in vivo as determined by acquisition of CD69 expression, but also increased the surface expression of CD69 amongst CD8 T cells (FIGS. 3D and 3E). Splenic CD8 T cells harvested from 3ACtreated mice have enhanced cytolytic capacity with increased frequency of LAMP-1 (CD107a) expression, a marker of cellular degranulation, following crosslinking of their TcR and the costimulatory molecule CD28 (FIG. 3F). Thus, 3AC treatment increased the responsiveness of both T and NK cells in vivo to stimulation via major activating receptors.

Example 4

SHIP Inhibitor Acts as an Immunotherapeutic

Figure 4A:
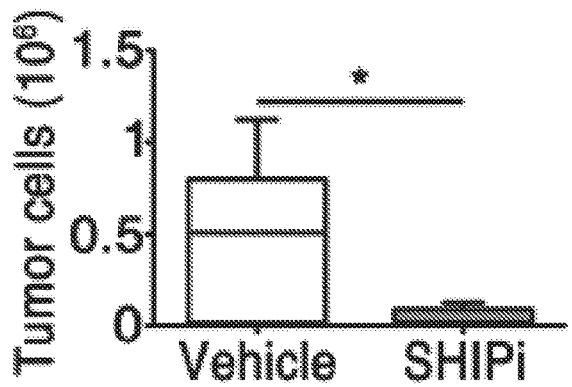
FIGS. 4A-4D show the effects of SHIP1 inhibition using 3AC in mice. $5 \times 10^5$ GFP-expressing RMA-Rael cells were injected into C57BL/6 (FIG. 4A), RAG1−/− (FIG. 4B), or into C57BL/6 hosts (FIG. 4C-4D) with antibody depleted (NK) or intact (Iso) NK cell compartment. Mice were treated with either SHIP inhibitor or vehicle for two days. Tumor burden was determined by flow cytometric analysis of peritoneal cavity contents recovered by peritoneal lavage performed on the third day. Graphs represent pooled data from two independent experiments using at least 4 SHIP inhibitor-treated mice and 4 vehicle-treated mice in each experiment.
Figure 4B:
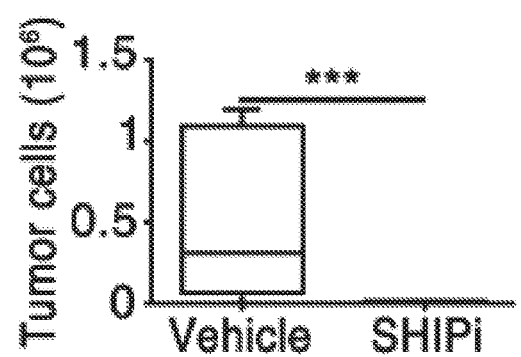
Figure 4C:
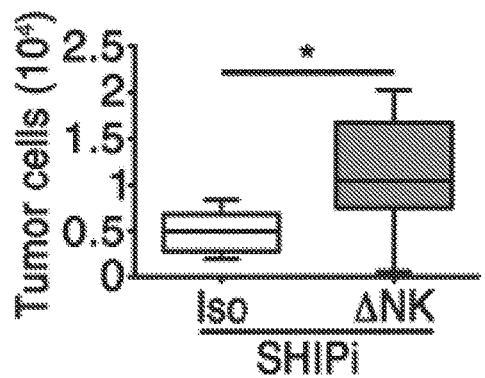
Figure 4D:
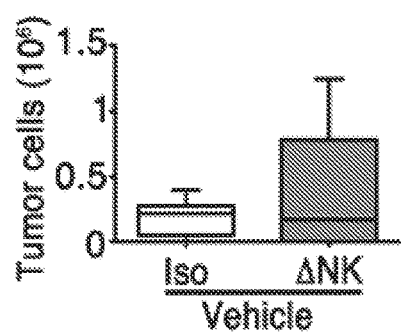

To determine if acute SHIP inhibitor treatment promoted in vivo clearance of tumor cells expressing a ligand for such receptors, the ability of SHIP inhibitor treatment to increase host rejection of tumor targets in vivo using the C57BL/6-derived H2b T cell lymphoma, RMA-Rael was analyzed. NK cell mediated rejection of RMA- Rael cells requires perforin expression and is independent of IFN$\gamma$ production, and thus this assay allows for interrogation of a different NK cell effector function than that analyzed in FIG. 3 (Hayakawa, Y. et al., Cutting edge: tumor rejection mediated by NKG2D receptor-ligand interaction is dependent upon perforin. J Immunol. (2002); 169: 5377-538). Mice were challenged with syngeneic tumor cells followed by treatment with 3AC or vehicle for 2 consecutive days. On the third day peritoneal lavage was performed to evaluate tumor burden. A dramatic reduction in lymphoma burden following 3AC treatment was observed in C57BL/6 hosts having a fully functional adaptive immune system. A similar reduction was also observed in RAG1$^{-/-}$ hosts that lack B and T cells, and thus acute rejection was not attributable in this assay to increased anti-tumor activity by B or T lymphocytes (FIG. 4B). To assess whether NK cells contributed to acute tumor rejection the same experiment using NK cell depleted C57BL/6 hosts (DNK) was performed. 3AC-treated hosts with an intact NK cell compartment had significantly greater tumor rejection compared to 3AC hosts depleted of NK cells prior to tumor challenge (FIG. 4C). This increase in tumor burden was not seen in vehicle treated mice that were also depleted of NK cells (FIG. 4D). Interestingly, regardless of whether mice were depleted of NK cells prior to tumor challenge, 3AC-treated mice had a profound reduction of tumor burden as compared to vehicle-treated controls (FIG.

4C and D). These results indicated that NK cells are required for 3AC-induced acute tumor rejection, but that there may be multiple mechanisms through which 3AC mediates hosts protection from malignancy.

Example 5

Figure 5A:
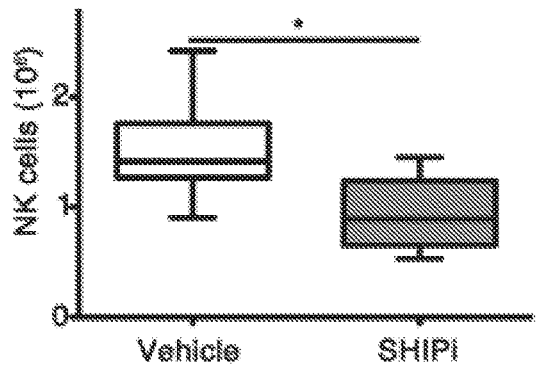
FIGS. 5A-5I show the effects of SHIP1 inhibitor as a chemotherapeutic.
Figure 5B:
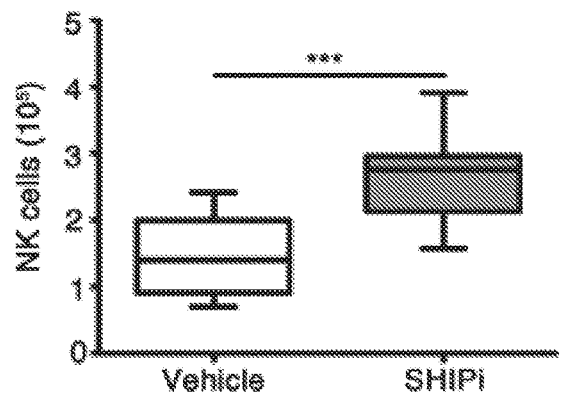
Figure 5C:
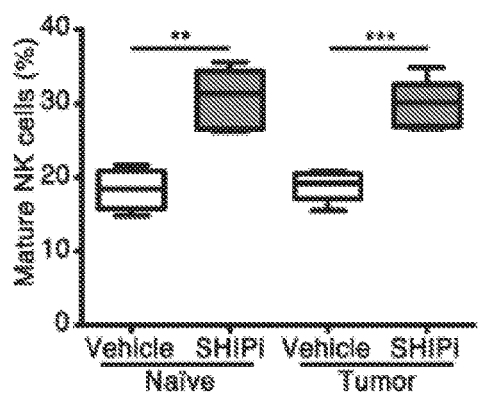

3AC increases NK Cell Numbers and Maturation at the Tumor Site and Enhances FasL-Fas Mediated Killing of Lymphoma Cells Similar to mice with NK cell specific deletion of SHIP1 that have NK cell lymphocytopenia (Gumbleton, M. et al., SHIP1 intrinsically regulates NK cell signaling and education, resulting in tolerance of an MHC class I-mismatched bone marrow graft in mice. J Immunol, (2015)), 3AC-treated mice also have decreased numbers of splenic NK cells (FIG. 5A). However, short-term inhibition of SHIP1 signaling with 3AC significantly increased the number of NK cells present at the tumor site in the peritoneal cavity (FIG. 5B) and also significantly increased the terminal maturation of the peripheral NK cell compartment as assayed in the spleen (FIG. 5C). This terminally differentiated NK cell subset possesses increased cytolytic potential and thus their increased numbers in 3AC-treated hosts is consistent with the increased tumor eradication observed after 3AC treatment (Hayakawa, Y. and M. J. Smyth, CD27 dissects mature NK cells into two subsets with distinct responsiveness and migratory capacity. J Immunol., (2002); 176: 1517-1524.

Figure 5D:
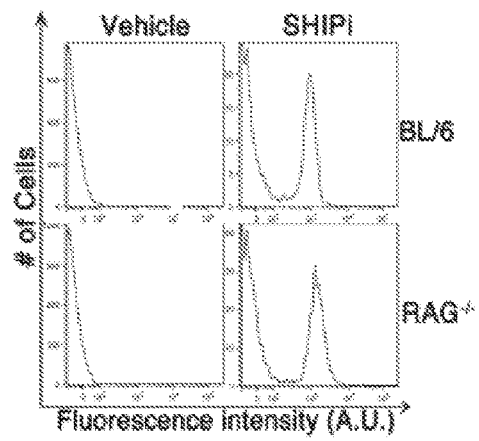
Figure 5E:
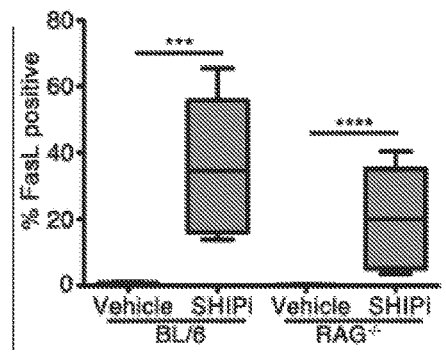
Figure 5F:
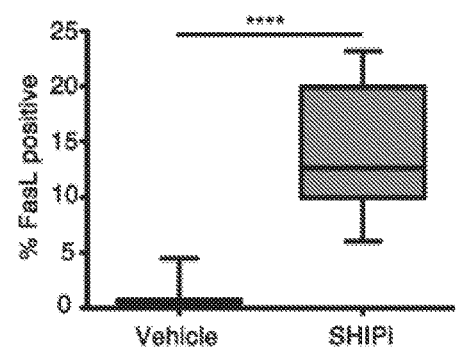
Figure 5G:
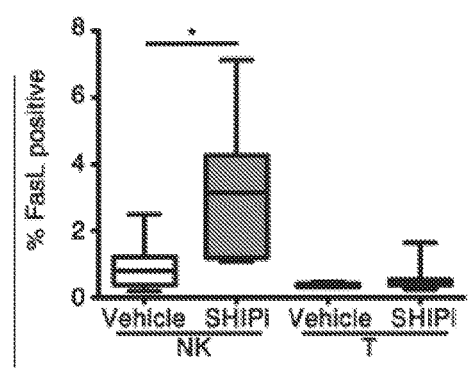
Figure 5H:
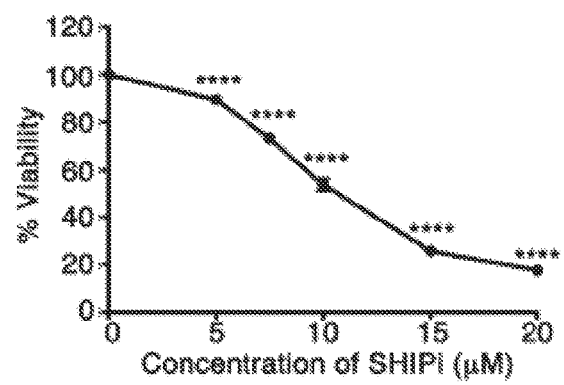
Figure 5I:
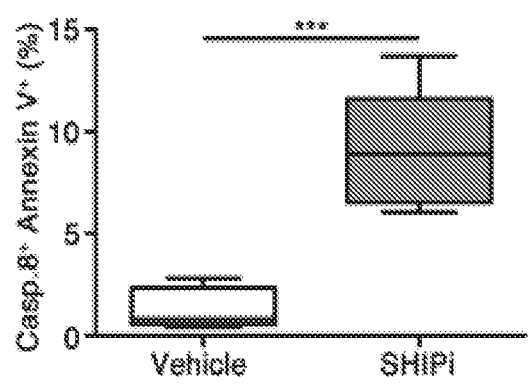

NK cells are able to directly kill target cells through several different mechanisms including both production of perforin and granzymes and induction of apoptosis via Fas-FasL signaling (Arase, H. et al., Fas-mediated cytotoxicity by freshly isolated natural killer cells. J Exp Med. (1995); 181: 1235-1238; Zamai, L. et al., Natural killer (NK) cell-mediated cytotoxicity: differential use of TRAIL and Fas ligand by immature and mature primary human NK cells. J Exp Med. (1998); 188: 2375-2380). 3AC-treated RMA cells express increased frequency of the death receptor CD95/Fas that initiates apoptosis via induction of Caspase 8 following ligation by FasL/CD95L. SHIP1 was recently shown to be recruited to CD95/Fas to set a threshold for induction of Caspase 8, and thereby, a threshold for induction of apoptosis (Park, M. Y. et al., Impaired T-cell survival promotes mucosal inflammatory disease in SHIP1-deficient mice. Mucosal Immunol. (2014); 7: 1429-1439). This pathway might contribute to 3AC-mediated killing of lymphoma cells in a host-extrinsic fashion and, possibly, even to NK cell mediated clearance of tumor in vivo. To explore this possibility, whether 3AC induces FasL, the death ligand, on cytotoxic host cells present in the tumor site was examined. A profound acquisition of FasL amongst both host NK cells as well as T cells at the tumor site in 3AC-treated mice that was not seen in vehicle-treated, tumor-challenged control mice (FIG. 5D to 5F) was observed. Interestingly, a small, but significantly increased frequency of splenic NK cells, but not T cells, also acquired FasL expression following 3AC treatment (FIG. 5G). As shown above in FIG. 4, NK cells are required for maximal reduction of tumor burden; however, there was also a large reduction in tumor burden amongst NK cell deficient hosts treated with 3AC indicating a possible direct chemotherapeutic effect of 3AC on the T cell lymphoma. This is consistent with what has been previously reported with multiple myeloma, myeloid leukemias and T cell leukemia, and that others have recently reported in preB ALL (Park, M. Y. et al., Impaired T-cell survival promotes mucosal inflammatory disease in SHIP1-deficient mice. Mucosal Immunol. (2014); 7: 1429-1439; Brooks, R. et al., SHIP1 inhibition increases immunoregulatory capacity and triggers apoptosis of hematopoietic cancer cells. J Immunol. (2010); 184: 3582-3589; Fuhler, G. M. et al., Therapeutic potential of SH2 domain-containing inositol-5'-phosphatase 1 (SHIP1) and SHIP2 inhibition in cancer. Mol Med. (2012); 18: 65-75; Chen, Z. et al, Signalling thresholds and negative B-cell selection in acute lymphoblastic leukaemia. Nature. (2015)) . 3AC was capable of directly killing RMA-Rael cells (FIG. 5H). There was also a significant induction of apoptosis in 3AC-treated RMA cells and increased activation of Caspase 8 consistent with 3AC lowering the threshold for Fas signaling (FIG. 5I) as has been previously shown in a human T cell leukemia (Park, M. Y. et al., Impaired T-cell survival promotes mucosal inflammatory disease in SHIP1-deficient mice. Mucosal Immunol. (2014)). Therefore, the improved tumor clearance and survival following acute 3AC treatment in vivo may result from both a chemotherapeutic effect and enhanced immune control.

Example 6

3AC Increases Survival of Tumor Bearing Mice

Figure 6A:
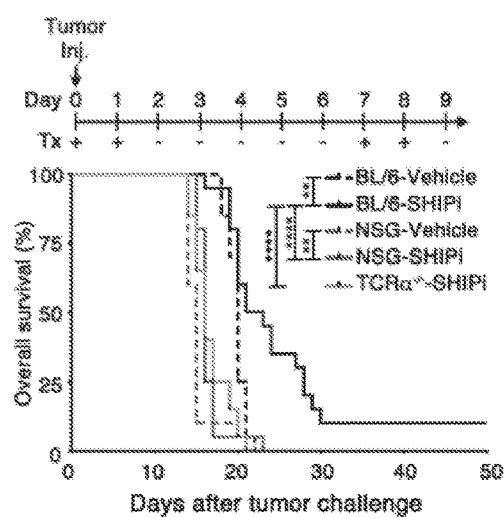

The most clinically relevant endpoint in any cancer therapy study is not a measured decrease in tumor burden, but instead, a significant increase in survival promoted by the treatment. To determine if the increased killing of tumor cells by hyper-activated NK and T cells, as well as increased apoptosis of tumor cells induced by 3AC, resulted in increased survival of tumor challenged hosts RMA-Rael tumor bearing C57BL/6 hosts were treated with either 3AC or vehicle for two consecutive days each week followed by a five-day cessation of treatment and then monitored survival (FIG. 6A). This pulsatile dosing strategy was chosen to avoid NK cell disarming and T cell exhaustion due to unattenuated activation as seen in mice with genetic or prolonged pharmacological ablation of SHIP signaling (Gumbleton, M. et al., SHIP1 intrinsically regulates NK cell signaling and education, resulting in tolerance of an MHC class I-mismatched bone marrow graft in mice. J Immunol. (2015); Fernandes, S. et al., SHIPi enhances autologous and allogeneic hematopoietic stem cell transplantation. E Bio Medicine. (2015)). 3AC treated hosts had significantly increased survival compared to vehicle treated controls (FIG. 6A). Importantly, this tumor burden was uniformly lethal in vehicle treated mice while a subpopulation of 3AC treated mice had durable, long term survival without any evidence of tumor burden (FIG. 6A) indicating that 3AC can even be curative in a subset of tumor-challenged hosts.

In order to further define 3AC's capacity to control malignancy through immunomodulatory effects the capacity of 3AC to promote resistance of NSG, TcRa$^{-/-}$ and NK cell depleted hosts to RMA-Rael tumor challenge was examined. As before, mice received treatment with 3AC or vehicle for two consecutive days each week followed by a five-day cessation of treatment to prevent disarming and/or exhaustion. This treatment strategy was continued indefinitely and survival was monitored (FIG. 6A). To confirm that, in addition to the chemotherapeutic effect documented in FIG. 5, 3AC-induced enhanced-NK and -T cell activity is important for the survival benefit following tumor challenge, NSG mice (mice deficient of all lymphocyte lineages) were challenged. Only a very modest increase in median survival in 3AC-treated NSG mice compared to vehicle-treated NSG controls, consistent with the direct-killing of tumor cells by 3AC and confirming that an intact host immune system is indeed required for maximal resistance to malignancy (FIG. 6A) were observed.

Figure 6B:
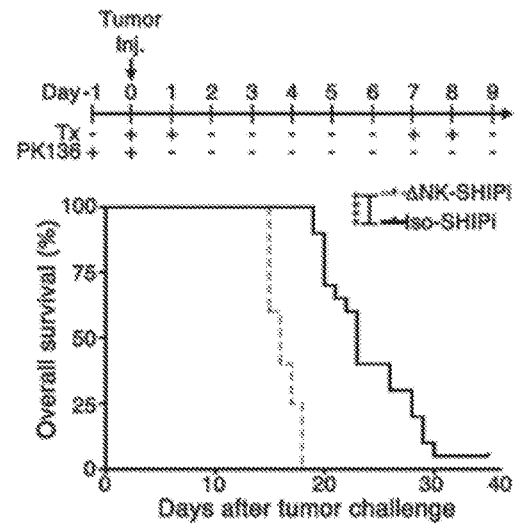

To determine if T cells are required for the 3AC-mediated survival benefit, the same expirement using TcRa$^{-/-}$ hosts that lack a TcR-ab$^+$ T cell compartment was repeated. Indeed, 3AC treatment of TcRa$^{-/-}$ hosts did not prolong survival following tumor challenge when compared to 3AC treatment of C57BL/6 hosts with an intact T cell compartment. These results indicated maximal and sustained protection from tumor promoted by 3AC requires the presence of an intact lymphocyte compartment that includes TcRa expressing T cells (FIG. 6A). 3AC-treated TcRa$^{-/-}$ hosts did not exhibit significantly increased survival after tumor challenge despite an intact NK cell compartment suggesting that while NK cells are required for maximal acute rejection of tumor (FIG. 4), NK cells may not contribute to the 3AC-mediated increase in overall survival. To directly test the requirement for an intact NK cell compartment for 3AC-mediated increased survival after tumor challenge, the experiment as described in FIG. 6A were repeated challenging C57BL/6 hosts that were first depleted of NK cells. Here, prior to tumor challenge, hosts were injected with either NK cell depleting anti-NK1.1 antibody (C57BL/6-DNK) or with antibody isotype control (C57BL/6-iso) (FIG. 6B). NK cell depletion significantly compromised survival of 3AC-treated hosts relative to 3AC-treated hosts pretreated with antibody isotype control (FIG. 6B). These findings demonstrate that an intact NK cell compartment is indeed required for 3AC to extend survival after tumor challenge.

Figure 6C:
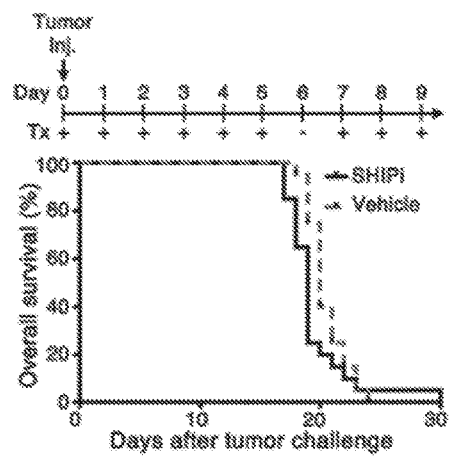
Figure 6D:
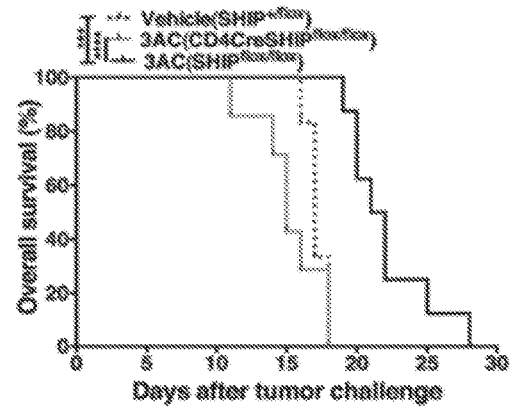

Mice receiving uninterrupted, extended-duration 3AC (treatment for six days each week) have a disabled NK cell compartment as indicated by their inability to acutely reject an MHC-I mismatched BM graft (Fernandes, S. et al., SHIPi enhances autologous and allogeneic hematopoietic stem cell transplantation. E Bio Medicine. (2015)) a unique in vivo effector function of NK cells (Murphy, W. J. et al., Rejection of bone marrow allografts by mice with severe combined immune deficiency (SCID). Evidence that natural killer cells can mediate the specificity of marrow graft rejection. Immunity. (1996); 4:67-76). To further explore whether NK cells contribute to 3AC mediated enhanced survival after tumor challenge, resistance to tumor challenge in hosts that received the same, extended-duration 3AC treatment, which has previously been shown to disarm the NK cell compartment (Fernandes, S. et al., SHIPi enhances autologous and allogeneic hematopoietic stem cell transplantation. E Bio Medicine. (2015)) was examined. Increased survival of tumor challenged C57BL/6 hosts receiving extended-duration 3AC compared to vehicle treated controls (FIG. 6C) was not observed. Thus, consistent with the hypothesis that SHIP1 opposes NK cell activation to prevent disarming, sustained treatment with 3AC disarms the NK cell compartment and effectively compromises extended survival following tumor challenge as opposed to the transient and pulsatile 3AC treatment strategy that induces NK cell activation and tumor rejection. The SHIP1 inhibitor 3AC was then tested in a genetic model in which the molecular target, SHIP1, was absent in a key target population of T cells, which are required for protection in the RMA-Rael lymphoma challenge model. Mice that selectively lack SHIP1 in T cells (CD4CreSHIP$^{flox/flox}$ mice) treated with 3AC following RMA-Rael challenge demonstrated comparable survival to vehicle-treated SHIP$^{+/flox}$ mice that have SHIP1 competent T cells (FIG. 6D). Thus, 3AC and a SHIP1-deficient T cell compartment did not compromise baseline host resistance to RMA-Rael challenge. However, lymphoma-challenged SHIP$^{flox/flox}$ mice treated with 3AC demonstrateden-hanced survival vs. both the SHIP1-deficient T cell, 3AC-treated hosts (CD4CreSHIP$^{flox/flox}$) and the SHIP1-competent T cell, vehicle-treated hosts (SHIP$^{+/flox}$) (FIG. 6D). Thus, SHIP inhibitor protection after tumor challenge is lost when the T cell compartment lacks the molecular target (SHIP1) in T cells. This further supported the finding that T cells are required for 3AC-promoted increased resistance to tumor growth, and demonstrated that targeting of SHIP1 in T cells was essential for this effect. Taken together, the above findings demonstrate that 3AC enhances both NK and T cell function to promote host resistance to cancer and does so by targeting SHIP1.

Example 7

Selective SHIP1 Inhibition is Required to Promote Improved Tumor Survival

Figure 6E:
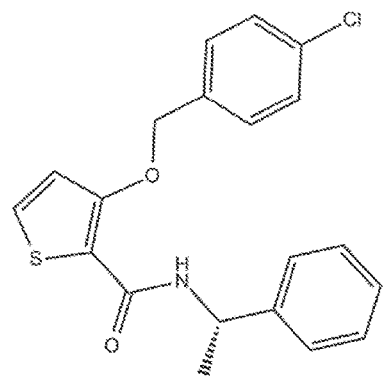
Figure 6F:
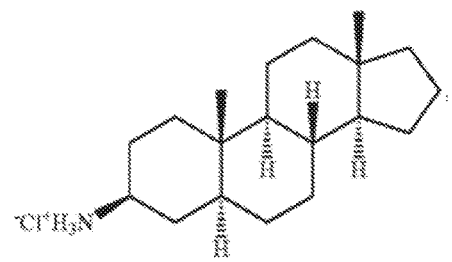

There are two paralogs of SHIP: SHIP1 which is expressed in a limited range of tissues including hematopoietic cells, and SHIP2 which is expressed by a wide array of cell types. To determine if SHIP2 may also play a role in host defense against malignancy as described above tumor bearing mice were treated with small-molecule inhibitors against SHIP2 as well. The small molecules shown to inhibit the SHIP 1 and 2 paralogs included those with a high degree of selectivity for either SHIP1 (e.g. 3AC (Brooks, R. et al., SHIP1 inhibition increases immunoregulatory capacity and triggers apoptosis of hematopoietic cancer cells. J Immunol. (2010); 184: 3582-3589) or SHIP2 (e.g., AS1949490; 3-[(4-ChlorophenyOmethoxy]-N-[(1S)-1-phenylethyl]thiophene-2-carboxamide (Suwa, A. et al., Discovery and functional characterization of a novel small molecule inhibitor of the intracellular phosphatase, SHIP2. Br J Pharmacol. (2009) 158: 879-887)) or those that exhibit pan-SHIP1/2 inhibitory activity, such as K118 (3β-amino-5α-androstane hydrochloride) and K149 (2-[1-(4-chlorobenzyl)-2-methyl-5-(methylmercapto)-1H-3-yl] ethanaminium chloride) (see FIGS. 6E-6G for chemical structures) (Brooks, R. et al., Coordinate expansion of murine hematopoietic and mesenchymal stem cell compartments by SHIPi. Stem Cells. (2015); 33: 848-858; Hoekstra, E. et al., Lipid phosphatase SHIP2 functions as oncogene in colorectal cancer by regulating PKB activation. Oncotarget. (2016) 7: 73525-73540). Like 3AC, pan-SHIP1/2 inhibitors such as K118 are also cytotoxic for RMA-Rael cells in vitro. The pan SHIP1/2 inhibitory compounds K118 and K149 were compared to the SHIP1 selective compound 3AC. Despite their ability to target SHIP1, there was no protection afforded by either pan-SHIP1/2 inhibitory compound (FIG. 6H), whereas selective SHIP1 inhibitor 3AC again extended survival in the RMA-Rael lymphoma model as before, including providing long-term survival in a subset of hosts.

Simultaneous inhibition of both SHIP1 and SHIP2 may be deleterious to the immune response promoted by 3AC. To test this, a similar study where RMA-Rael lymphoma challenged mice were treated with the highly selective SHIP2 inhibitory AS1949490 was performed. In the study, the SHIP1 selective inhibitor 3AC that provides for protection after RMA-Rael challenge was simulataneously co-administered. Treatment with AS1949490 offered no protection and, in agreement with the hypothesis, co-inhibition of SHIP2 by AS1949490 completely abrogated the protective effect of 3AC administration (FIG. 6I).

These results further confirmed that the SHIP1-selective inhibitor 3AC has potent anti-tumor properties, but importantly they demonstrated that the beneficial effects of SHIP1 inhibition required paralog-selective inhibition.

Example 8

Immunological Memory to Tumor is Present in Long-Term Surviving Hosts

Figure 6G:
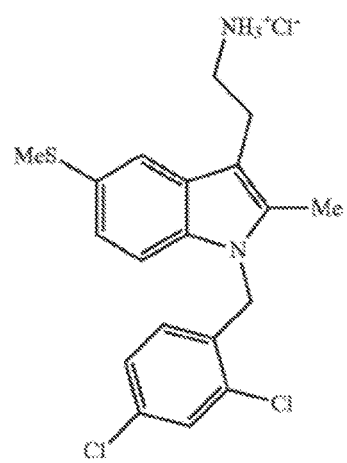

Given that SHIP inhibitor induced long-term survival amongst a subset of tumor challenged mice, SHIP inhibitors may also induce formation of immunological memory capable of sustained and protective response to tumor that prevents relapse. To test for continued presence of such immunity, hematolymphoid cells were adoptively transferred from either a nave donor or from a tumor challenged, 3AC treated, long-term surviving (primed) donor into nave C57BL/6 hosts. These hosts (nave to both treatment and tumor) were then challenged with tumor, but did not receive 3AC treatment. Recipients of primed hematolymphoid cells had significantly increased survival compared to recipients of nave hematolymphoid cells following tumor challenge (FIG. 6G). This indicated that long-term survivors of tumor challenge treated with 3AC had immune cells capable of a protective and sustained response to the tumor cells, even after adoptive transfer.

Example 9

SHIP1 Inhibitor 3AC Limits Tumor Growth in Non-Hematologic Malignancies

Figure 7A:
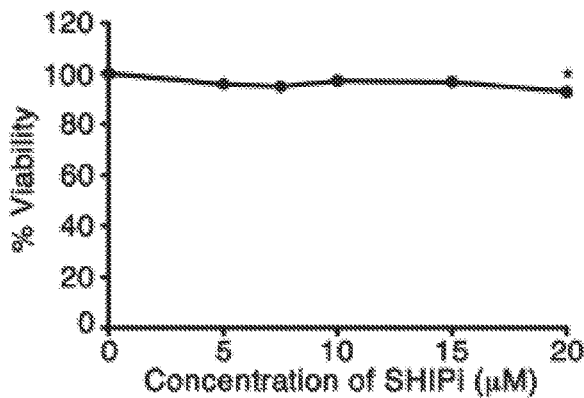
FIGS. 7A-7H shows the reduction of non-hematopoietic tumor progression with SHIP inhibitor 3AC.
Figure 7B:
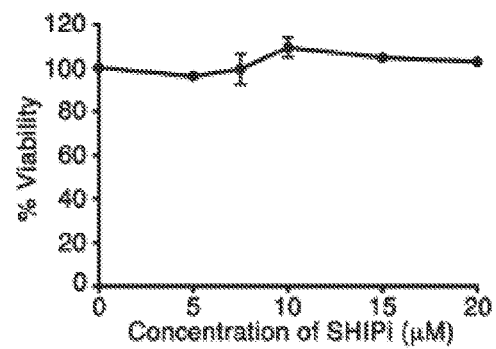
Figure 7C:
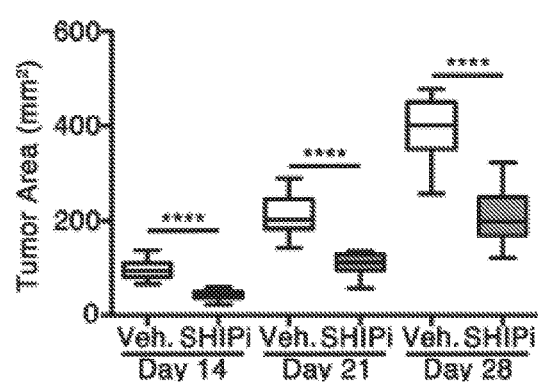
Figure 7D:
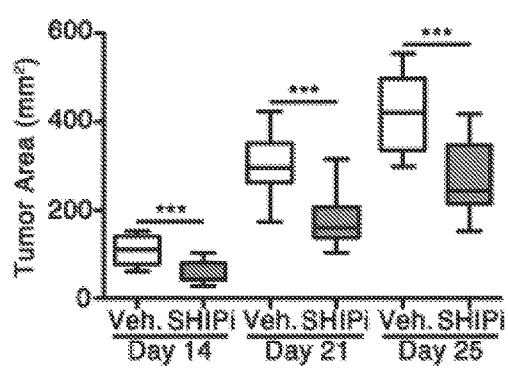
Figure 7E:
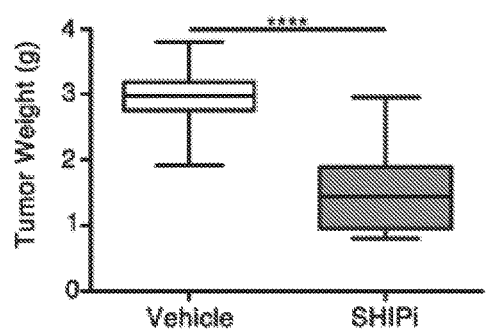
Figure 7F:
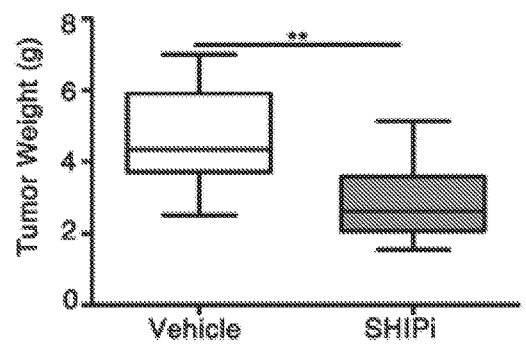
Figure 7G:
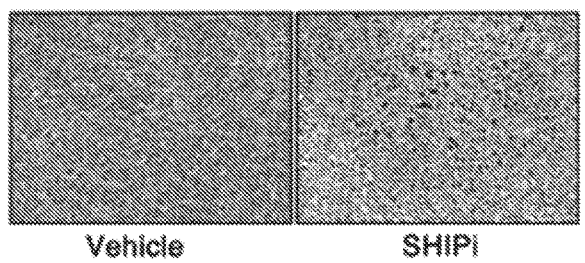
Figure 7H:
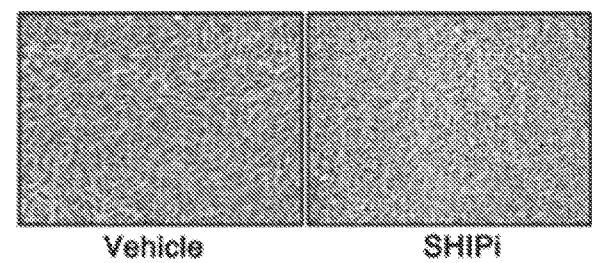

Colorectal cancer is the second leading cause of cancer mortality in the United States (Siegel, R. L. et al., Colorectal cancer statistics, 2017. CA Cancer J Clin. (2017)). To determine if 3AC is able to potentiate host rejection of solid tumors in addition to liquid malignancy, mice with CT26 and MC-38, were challenged. CT26 is a spontaneous colon carcinoma that arose in BALB/c mice. MC-38 is a carcinogen-induced colon carcinoma identified in a C57BL/6 host. These are two prominent tumor models that are regularly featured in murine studies of immunotherapy. The growth of both tumors has previously been shown to be subject to immune control models with T cells responses being a predominant mediator of immune control, but with NK cells also contributing to reduced tumor growth (Salagianni, M. et al., NK cell adoptive transfer combined with Ontak-mediated regulatory T cell elimination induces effective adaptive antitumor immune responses. J Immunol. (2011) 186: 3327-3335; Sakuishi, K. et al., Targeting Tim-3 and PD-1 pathways to reverse T cell exhaustion and restore anti-tumor immunity. J Exp Med. (2010); 207: 2187-2194; Hodge, J. W. et al., Vaccine therapy of established tumors in the absence of autoimmunity. Clin Cancer Res. (2003); 9: 1837-1849; Nagasaki, E. et al., Combined treatment with dendritic cells and 5-fluorouracil elicits augmented NK cell-mediated antitumor activity through the tumor necrosis factor-alpha pathway. J Immunother. (2010); 33: 467-474; Haynes, N. M. et al., CD11c+ dendritic cells and B cells contribute to the tumoricidal activity of anti-DR5 antibody therapy in established tumors. Immunol. (2010); 185: 532-541). Unlike RMA-Rael, these tumors do not express SHIP1 and thus are resistant to direct killing by the SHIP1 selective inhibitor 3AC (FIGS. 7A and B). Mice were challenged with subcutaneous injection of CT26 or MC-38 tumor cells into the right flank and then received either 3AC or vehicle control for two consecutive days each week. We observed a significant reduction in tumor size and weight in both CT26 (FIG. 7C and 7E) and MC-38 (FIGS. 7D and 7F) tumor models amongst the 3AC-treated mice as compared to vehicle-treated controls. Histological analysis of both tumors showed prominent zones of tumor cell death only in the tumors harvested from 3AC-treated hosts (FIGS. 7G and 7H) consistent with significantly reduced tumor growth relative to vehicle controls. These results showed that 3AC can also promote reduced growth of non-hematolymphoid tumor types that lack SHIP1 expression.

Example 10

Intermittent Dosing of Patients with Selective SHIP1 Inhibitors

An effective dose of a selective SHIP1 inhibitor (e.g. K223) is administered by any appropriate means (e.g., orally, intravenously, intraperitoneally) to a patient for short administration periods separated by rest periods during which no SHIP1 inhibitor is administered. This cycle of selective SHIP1 inhibitor administration and rest periods can be repeated multiples (e.g., 2, 3, 4, 5, 7, 10, etc.). The short administration periods can be 1, 2, 3 or more days, with the selective SHIP1 inhibitor administered approximately daily or more than daily (e.g. twice a day or three times a day). The rest periods can be longer or shorter than the administration periods, and can be 2, 3, 4, 5, 6, 7, 8, 9, 10, 12, 15 days or longer. One administration protocol is to administer the selective SHIP1 inhibitor daily for 2 days followed by a 5-day rest period, with the cycle repeated multiple times.

Example 11

Continous Dosing of Patients with Selective SHIP1 Inhibitors

An effective dose of selective SHIP1 inhibitor (e.g. K223) is administered by any appropriate means (e.g., orally, intravenously, intraperitoneally) to a patient for administration periods of 3, 4, 5, 6, 7 or more days. This results in hyporesponsiveness in the activated T and NK cells.

The disclosures of each and every patent, patent application, and publication cited herein are hereby incorporated herein by reference in their entirety.

While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

The invention claimed is:

1. A method for inhibiting a SH2-containing inositol 5'-phosphatase 1 (SHIP 1) in a subject comprising administering to the subject an effective amount of 8-((2-aminoethyl)amino)naphthalene-1-sulfonic acid, or a pharmaceutically acceptable salt.

2. The method of claim 1, wherein the subject has an illness or condition for which NK cells and/or T cells provide a host defense.

3. The method of claim 2, wherein the illness or condition is a viral infection, a bacterial infection, or cancer.

* * * * *